(12) United States Patent
Hwang et al.

(10) Patent No.: US 7,846,559 B2
(45) Date of Patent: Dec. 7, 2010

(54) HETEROCYCLIC COMPOUND AND AN ORGANIC LIGHT EMITTING DEVICE COMPRISING THE SAME

(75) Inventors: Seok-Hwan Hwang, Suwon-si (KR); Young-Kook Kim, Suwon-si (KR); Yoon-Hyun Kwak, Suwon-si (KR); Chang-Ho Lee, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 77 days.

(21) Appl. No.: 12/180,015

(22) Filed: Jul. 25, 2008

(65) Prior Publication Data

US 2009/0128013 A1 May 21, 2009

(30) Foreign Application Priority Data

Nov. 16, 2007 (KR) .................. 10-2007-0117369

(51) Int. Cl.
*H01L 51/52* (2006.01)
*C07D 487/14* (2006.01)
*C07D 401/14* (2006.01)

(52) U.S. Cl. ............... 428/690; 313/504; 548/433; 427/58; 427/66

(58) Field of Classification Search ............. 428/690
See application file for complete search history.

(56) References Cited

U.S. PATENT DOCUMENTS 4,874,756 A   10/1989   Mertens et al.

FOREIGN PATENT DOCUMENTS

| EP | 0 673 979 | 3/1995 |
| JP | 2-196865 | 8/1990 |
| JP | 62-51686 | 5/1994 |
| JP | 2004-231709 | 8/2004 |
| JP | 2007088222 A | * 4/2007 |
| WO | WO 2006/122630 | 11/2006 |

OTHER PUBLICATIONS

Kinsley, D. A.; Plant, S. P. G. Journal of the Chemical Society, 1958, pp. 1-7.*
Sanji, T.; Shiraishi, K.; Kashiwabara, T.; Tanaka, M. Organic Letters, 2008, vol. 10 (13), pp. 2689-2692.*
Machine English translation of JP 2007088222 A. Feb. 26, 2010.*

(Continued)

*Primary Examiner*—D. Lawrence Tarazano
*Assistant Examiner*—J. L. Yang
(74) *Attorney, Agent, or Firm*—Stein McEwen, LLP

(57) ABSTRACT

A heterocyclic compound represented by Formula 1 below:

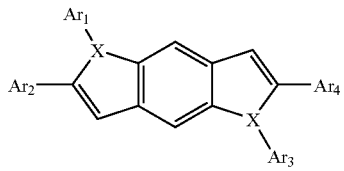

Formula 1

X is selected from the group consisting of nitrogen, boron, and phosphorous; and $Ar_1$, $Ar_2$, $Ar_3$ and $Ar_4$ are each independently selected from the group consisting of a C6-C30 substituted or unsubstituted aryl group, a C6-C30 substituted or unsubstituted aryloxy group, a C4-C20 substituted or unsubstituted heterocyclic group, and a C6-C20 fused polycyclic group.

The heterocyclic compound can be included in emission layers of top emission and bottom emission organic light emitting devices.

13 Claims, 2 Drawing Sheets

OTHER PUBLICATIONS

Sanji, Takanobu, et al. "Base-Mediated Cyclization Reaction of 2-Alkynylphenylphosphine Oxides: Synthesis and Photophysical Properties of Benzo[b]phosphole Oxides." *Organic Letters*. vol. 10, No. 13. 2008. pp. 2689-2692.

European Search Report issued by the European Patent Office on Mar. 19, 2009.

Korean Registration Determination Certificate dated Feb. 22, 2010, issued in corresponding Korean Patent Application No. 10-2007-0117369.

Abstract of EP 0216165.

* cited by examiner

HETEROCYCLIC COMPOUND AND AN ORGANIC LIGHT EMITTING DEVICE COMPRISING THE SAME

CROSS-REFERENCE TO RELATED APPLICATION

This application claims the benefit of Korean Patent Application No. 2007-117369, filed Nov. 16, 2007, in the Korean Intellectual Property Office, the disclosure of which is incorporated herein by reference.

BACKGROUND OF THE INVENTION

1. Field of the Invention

Aspects of the present invention relate to a heterocyclic compound, and an organic light emitting device including the same, and more particularly, to a heterocyclic compound with high color purity and excellent electrical stability.

2. Description of the Related Art

Electroluminescent emitting devices, which are self-emitting devices, have wide viewing angles, excellent contrast, and quick response times, and thus, have drawn a large amount of public attention. Electroluminescent light emitting devices can be classified into two types, inorganic light emitting devices, which include an inorganic emission layer, and organic light emitting devices (OLED), which include an organic emission layer. An OLED has a higher brightness, a lower operating voltage, a quicker response time, and can realize more colors, as compared to an inorganic light emitting device.

Typically, an OLED has an organic emission layer disposed between an anode and a cathode. An OLED can also have various other structures, such as a sequential stack of an anode, a hole transport layer, an organic emission layer, and a cathode, or sequential stack of an anode, a hole transport layer, an organic emission layer, an electron transport layer, and a cathode structure.

The National Television System Committee (NTSC) has set a color reproduction standard, which is defined by color coordinates R(0.67, 0.33), G(0.21, 0.71), B(0.14, 0.08). The area defined by these color coordinates is 0.158. Accordingly, a blue light emitting material, with a color purity close to the color coordinates of (0.14, 0.08) of NTSC standard, is needed, in order to realize natural picture quality, by improving the color gamut of displays. Since liquid crystal displays (LCDs) use a color filter, in conjunction with a light emitting diode (LED) backlight, a blue color with high color purity can be simply realized. However, since organic light emitting devices are self-emitting devices, fluorescent or phosphorescent materials that emit a high purity blue color, are needed.

However, only a sky blue color can be realized using known phosphorescent materials, and only a blue color with color coordinates of (0.15, 0.15) can be produced using current fluorescent materials. A top emission-type organic light emitting device has been developed, which is capable of realizing a high purity blue color, and a high efficiency, by using a sky blue fluorescent material, by incorporating a micro-cavity structure. However, in order to apply a micro-cavity structure to an organic light emitting device, optical length requirements need to be satisfied, and the thickness of the entire organic layer needs to be uniformly controlled. Thus, it is almost impossible to realize a large-scale organic light emitting device that can produce an acceptable color gamut. Therefore, in order to develop a large-scale organic light emitting device having a bottom emission structure, there is a need for a fluorescent light-emitting material that can emit a high color purity blue light.

SUMMARY OF THE INVENTION

Aspects of the present invention provide a blue light emitting material, having a high electrical stability, and a high color purity.

Aspects of the present invention also provide an organic light emitting device having excellent color reproduction, using the blue light-emitting material.

According to an aspect of the present invention, there is provided a heterocyclic compound represented by Formula 1:

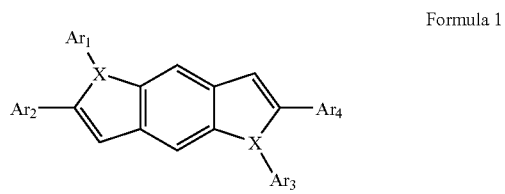

Formula 1

X is selected from the group consisting of nitrogen, boron and phosphorous. $Ar_1$, $Ar_2$, $Ar_3$, and $Ar_4$ are each independently selected from the group consisting of a C6-C30 substituted or unsubstituted aryl group, a C6-C30 substituted or unsubstituted aryloxy group, a C4-C20 substituted or unsubstituted heterocyclic group, and a C6-C20 fused polycyclic group.

According to another aspect of the present invention, there is provided an organic light emitting device including: a first electrode; a second electrode; and an organic layer interposed between the first electrode and the second electrode. The organic layer includes the heterocyclic compound.

The heterocyclic compound, according to aspects of the present invention, can effectively emit a blue light that has high color purity, and has a high electrical stability. Thus, an organic light emitting device having characteristics, such as a high efficiency, a low driving voltage, a high brightness, and a long lifetime can be prepared using the heterocyclic compound.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent, and more readily appreciated from, the following description of the exemplary embodiments, taken in conjunction with the accompanying drawings, of which.

DETAILED DESCRIPTION OF THE EMBODIMENTS

Figure 1:
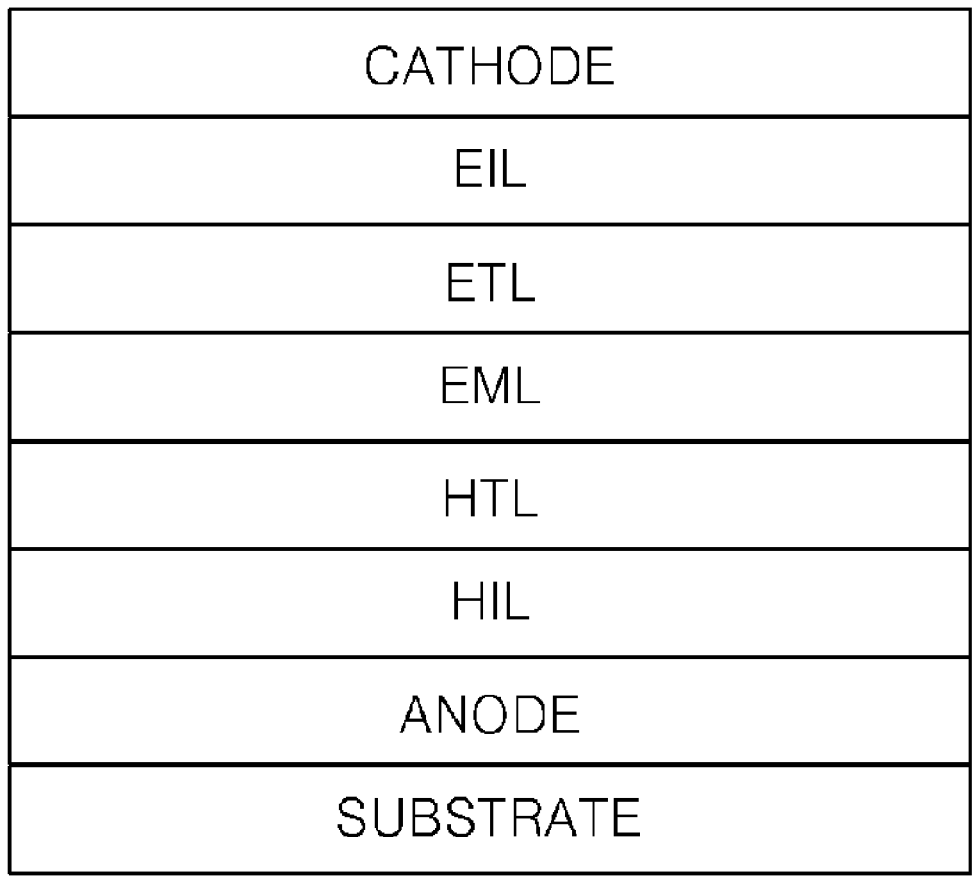
FIG. 1 shows the structure of an organic light emitting device, according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Aspects of the present invention provide an organic light emitting device that includes a heterocyclic compound, as a material used to form an organic layer. The heterocyclic compound has heterocyclic groups that are condensed into a single benzene ring. The heterocyclic compound is represented by the following Formula 1:

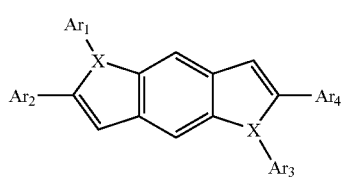

Formula 1

X is selected from the group consisting of nitrogen, boron, and phosphorous, which are trivalent substituents. X may be nitrogen for ease of preparation and color purity. $Ar_1$, $Ar_2$, $Ar_3$, and $Ar_4$ are each independently selected from a C6-C30 substituted or unsubstituted aryl group, a C6-C30 substituted or unsubstituted aryloxy group, a C4-C20 substituted or unsubstituted heterocyclic group, and a C6-C20 condensed polycyclic group.

An unsubstituted aryl group, applied to the compound of Formula 1, may be used alone or in combination. The aryl group indicates an aromatic carbocyclic system having 6-20 carbon atoms, and one or more rings. The rings may be bonded together in a pendent manner, or may be fused. Examples of the unsubstituted aryl group include a phenyl group, a naphthyl group, a biphenyl group, a terphenyl group, and a pentaphenyl group. At least one of the hydrogen atoms of the aryl group may be substituted with a C1-C5 alkyl group, a C1-C5 alkoxy group, a C6-C14 aryl group, a C6-C20 aryloxy group, a halogen atom, an amino group, or a cyano group. More particular examples of the aryl group are a phenyl group, an ethylphenyl group, a propylphenyl group, a butylphenyl group, a tert-butylnyl group, an o-, m- and p-fluorophenyl group, a difluorophenyl group, a trifluorophenyl group, a cyanophenyl group, a methoxyphenyl group, a phenoxyphenyl group, an o-, m-, and p-tolyl group, a (α,α-dimethylbenzene)phenyl group, a (N,N'-dimethyl)aminophenyl group, a (N,N'-diphenyl)aminophenyl group, a biphenyl group, a terphenyl group, a 3,5-diphenylphenyl group, a quarterphenyl group, and a pentaphenyl group, but are not limited thereto.

Examples of the unsubstituted heteroaryl group, applied to the compound of Formula 1, are a furanyl group, a pyridinyl group, and a thiophenyl group. At least one of the hydrogen atoms of the heteroaryl group may be substituted with a C1-C5 alkyl group, or the like.

Examples of the unsubstituted fused polycyclic group, applied to the compound of Formula 1, are a pentalenyl group, a naphthyl group, an azulenyl group, a heptalenyl group, an acenaphtyl group, an anthryl group, a phenanthryl group, a quinolyl group, an anthraquinolyl group, a fluorenyl group, and a carbazolyl group. At least one of the hydrogen atoms of the fused polycyclic group may be substituted with a C1-C5 alkyl group, a C1-C5 alkoxy group, a C6-C14 aryl group, a C6-C20 aryloxy group, a halogen atom, an amino group, or a cyano group. More particular examples of the unsubstituted fused polycyclic group are a pentalenyl group, a naphthyl group, a methylnaphthyl group, an anthracenyl group, an azulenyl group, a heptalenyl group, an acenaphthylenyl group, a fluorenyl group, a 9,9-dimethylfluorenyl group, a 9,9-diphenylfluorenyl group, an anthraquinolyl group, a penanthryl group, a triphenylene group, a carbazolyl group, and a 9-phenylcarbazolyl group, but are not limited thereto.

Examples of the unsubstituted aryloxy group, applied to the compound of Formula 1, are a phenyloxy group, a naphthyloxy group, an anthryloxy group, and a penanthryloxy group. At least one of the hydrogen atoms of the aryloxy group may be substituted with a C1-C5 alkyl group, a C1-C5 alkoxy group, a C6-C14 aryl group, a C6-C20 aryloxy group, a halogen atom, an amino group, or a cyano group.

$Ar_1$, $Ar_2$, $Ar_3$, and $Ar_4$ may be each independently selected from a phenyl group, a naphthyl group, a biphenyl group, a terphenyl group, a fluorenyl group, a carbazolyl group, a pyridyl group, and a quinolyl group (at least one of the hydrogen atoms of which may be substituted with a C1-C5 short-chain alkyl group), a C1-C5 short-chain alkoxy group, a cyano group, an amine group, a phenoxy group, a phenyl group, or a halogen atom. More specifically, $Ar_1$, $Ar_2$, $Ar_3$, and $Ar_4$ may each be a phenyl group, a phenyl group substituted with a C1-C5 alkyl group, a phenyl group substituted with a C1-C5 alkoxy group, a cyanophenyl group, a halophenyl group, a phenoxyphenyl group, a phenyl group substituted with a fluorenyl group, a naphthyl group, a naphthyl group substituted with a C1-C5 alkyl group, a naphthyl group substituted with a C1-C5 alkoxy group, a cyanonaphthyl group, a halonaphthyl group, a biphenyl group, a biphenyl group substituted with a C1-C5 alkyl group, a biphenyl group substituted with a C1-C5 alkoxy group, a diphenylphenyl group, a terphenyl group, a pyridyl group, a fluorenyl group, a fluorenyl group substituted with a C1-C5 alkyl group, a diphenyl fluorenyl group, or a quinolyl group. More particularly, $Ar_1$, $Ar_2$, $Ar_3$, and $Ar_4$ may be a phenyl group, an ethylphenyl group, a propylphenyl group, a butylphenyl group, a tert-butylphenyl group, an o-, m- and p-fluorophenyl group, a difluorophenyl group, a trifluorophenyl group, a cyanophenyl group, a methoxyphenyl group, a phenoxyphenyl group, an o-, m-, and p-tolyl group, a (α,α-dimethylbenzene)phenyl group, a (N,N'-dimethyl)aminophenyl group, a (N,N'-diphenyl)aminophenyl group, a biphenyl group, a terphenyl group, a 3,5-diphenylphenyl group, a quarterphenyl group, a pentaphenyl group, an anthryl group, fluorenyl group, a 9,9-dimethylfluorenyl group, a 9,9-diphenylfluorenyl group, a carbazolyl group, or a 9-phenylcarbazolyl group.

In the compound of Formula 1, $Ar_1$ and $Ar_3$ may be identical, and the $Ar_2$ may be $Ar_4$ may be identical, for ease of preparation. The heterocyclic compound may be represented by Formula 2 below:

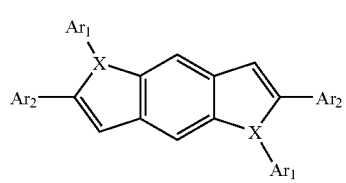

Formula 2

X, $Ar_1$, and $Ar_2$ are the same as described above.

Since the heterocyclic compound of Formula 1 includes a strong 3-ring structure, the glass transition temperature (Tg), and/or the melting point of the compound, is increased. Accordingly, the organic light-emitting device has an increased thermal resistance against heat generated in the organic layer, between the organic layers, and between the organic layer and the metal electrode. The organic light emitting device is stable in hot environments. Thus, the organic light emitting device has a high durability during storage and operation. The compound represented by Formula 1 can be a hole injecting material, a hole transporting material, and/or an emitting material.

Examples of the heterocyclic compound represented by Formula 1, may be the compounds represented by Formulae 1 to 105, shown below, but are not limited thereto.

1

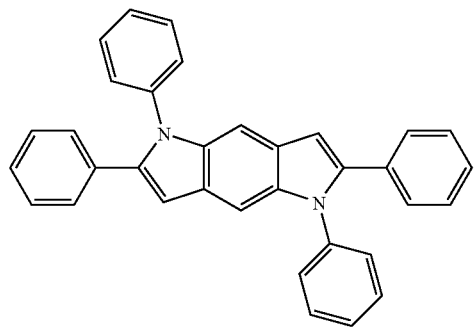

2

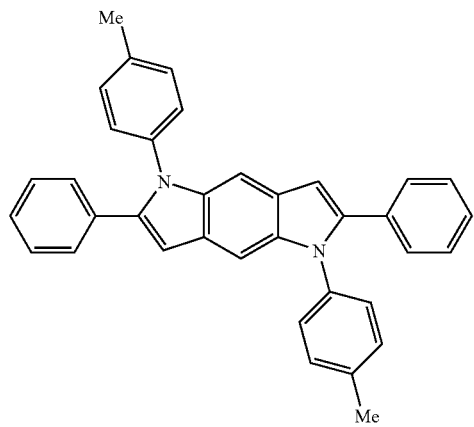

3

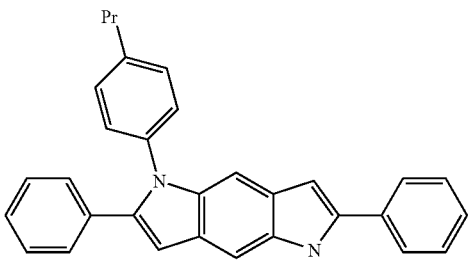

-continued

4

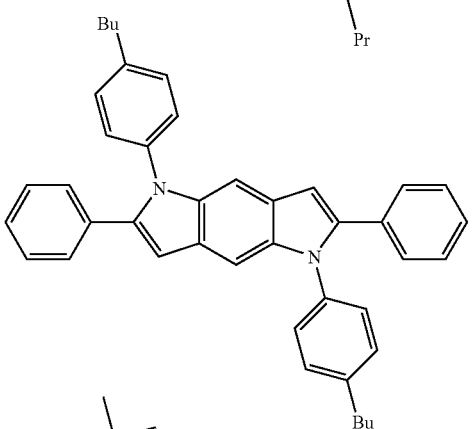

5

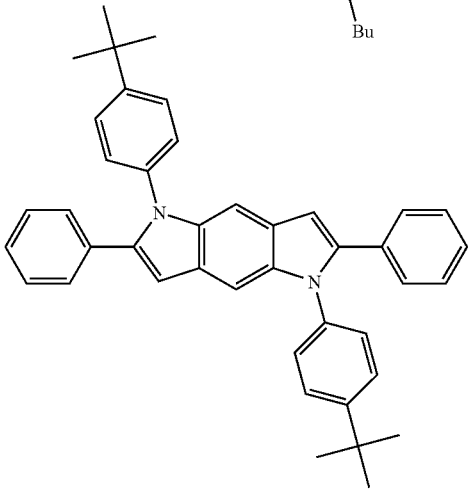

6

7

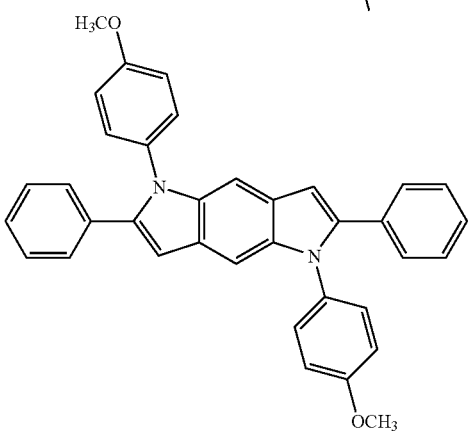

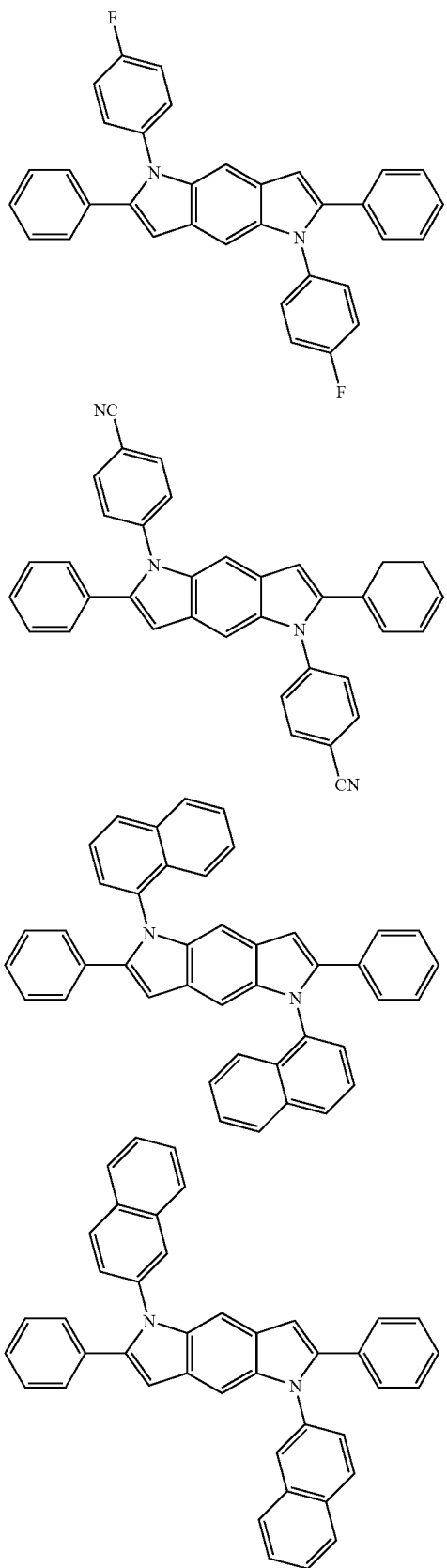
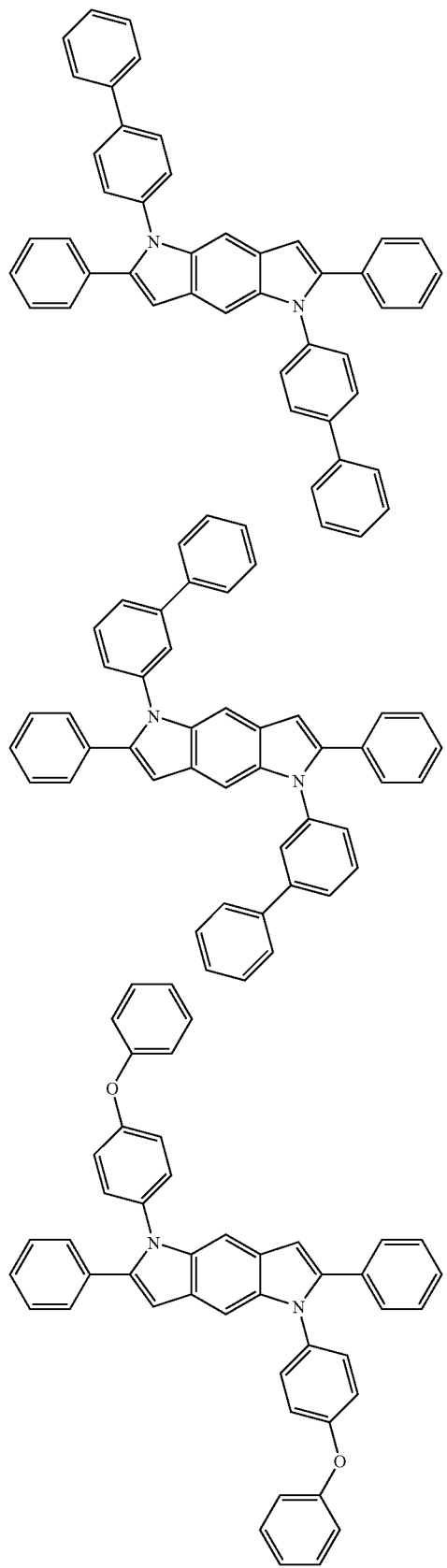

-continued
15
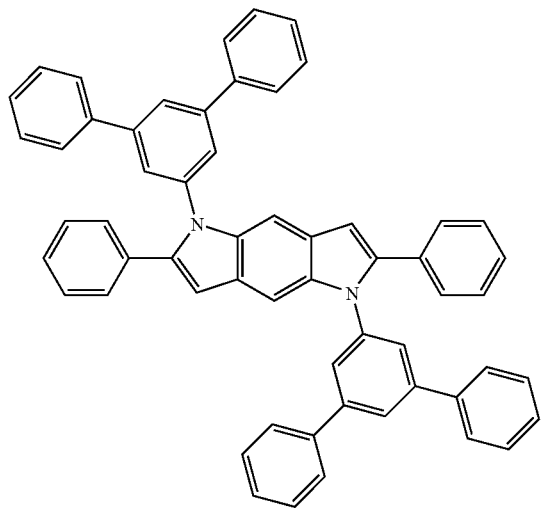
16
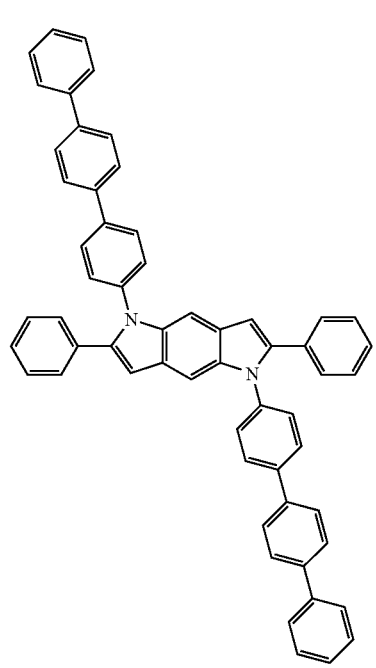
-continued
17
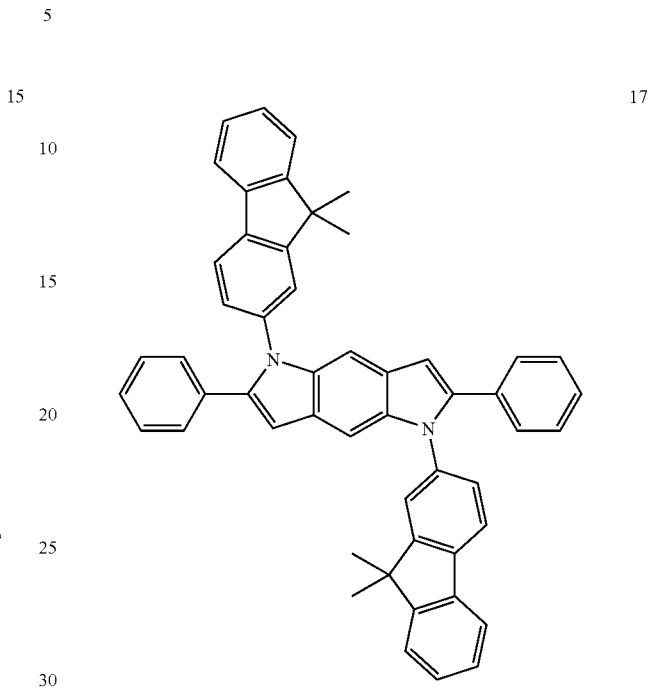
18
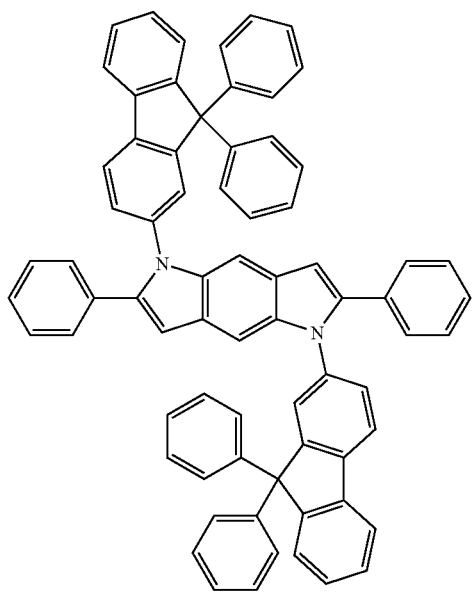

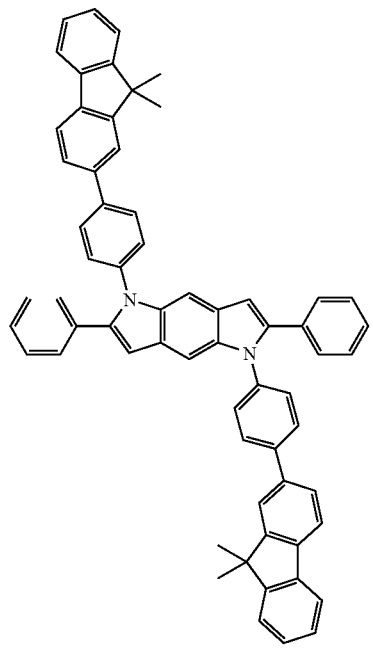
5
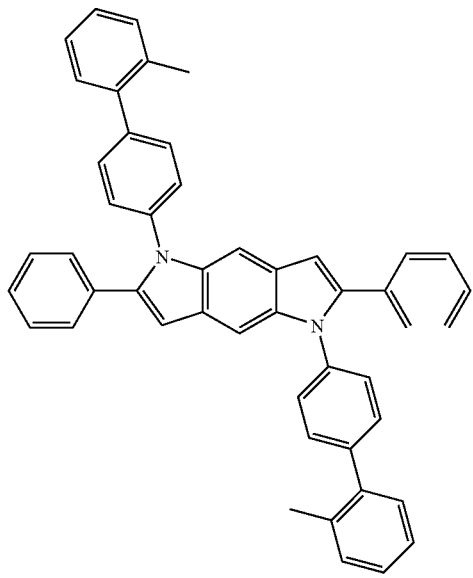
19
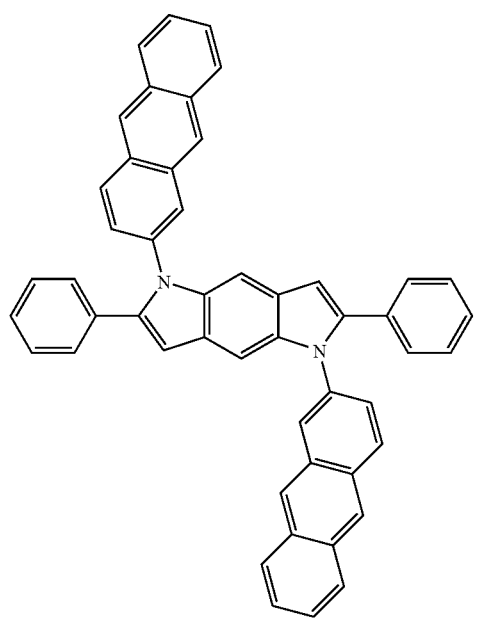
20
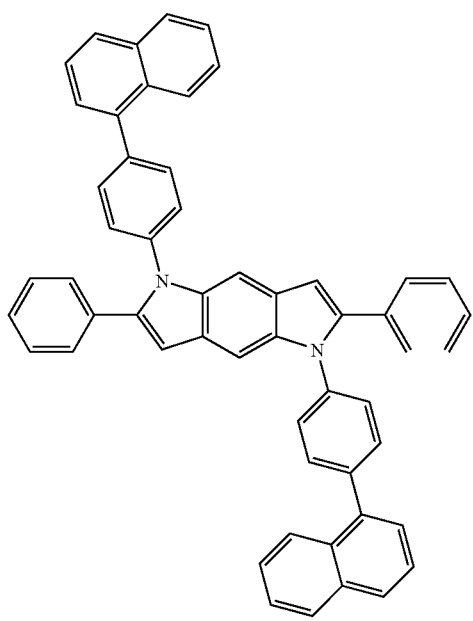
21
22

23
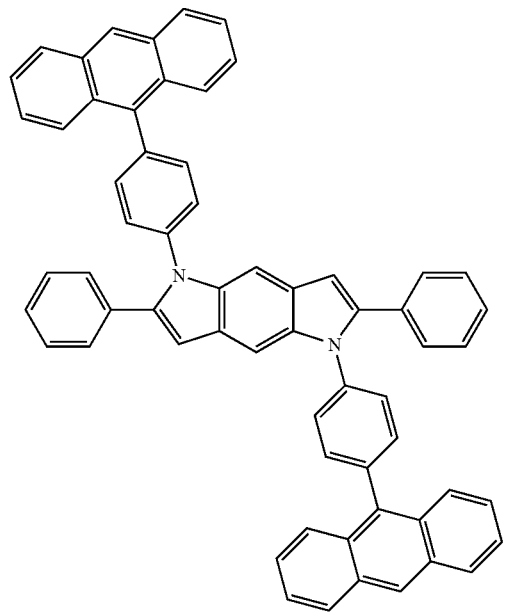
24
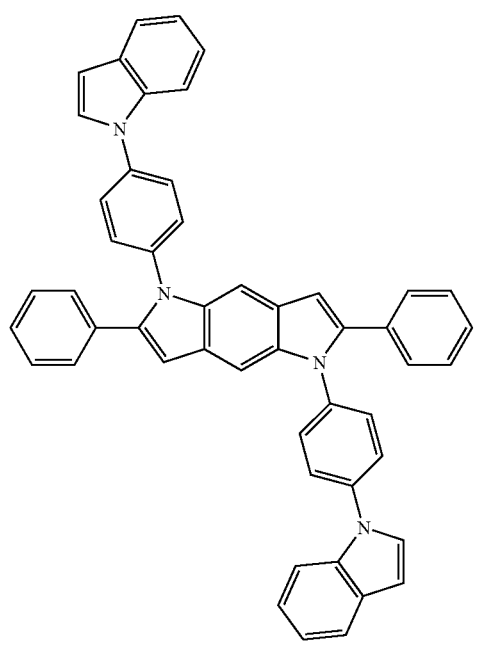
25
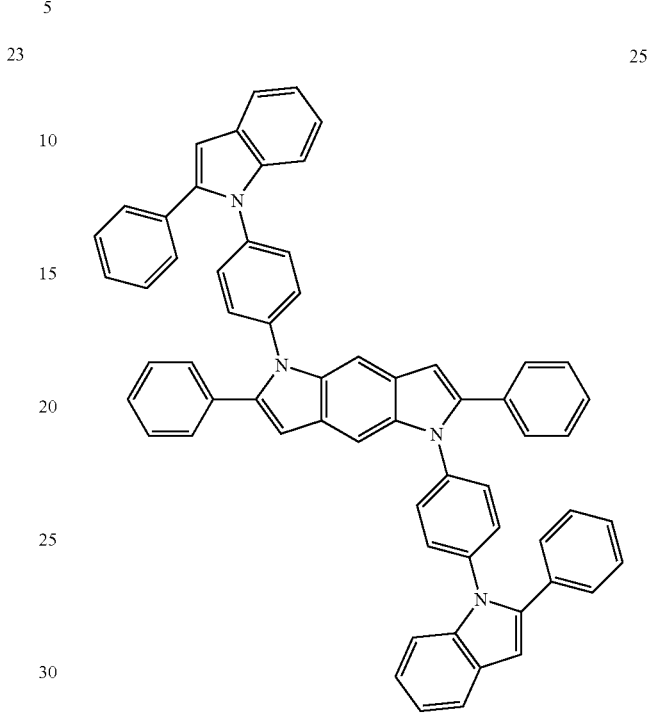
26
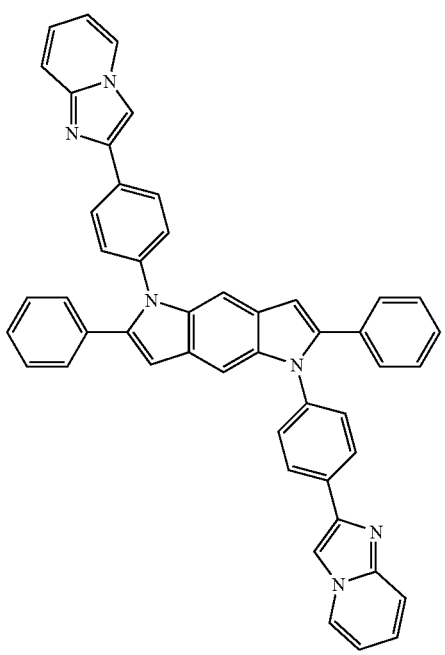

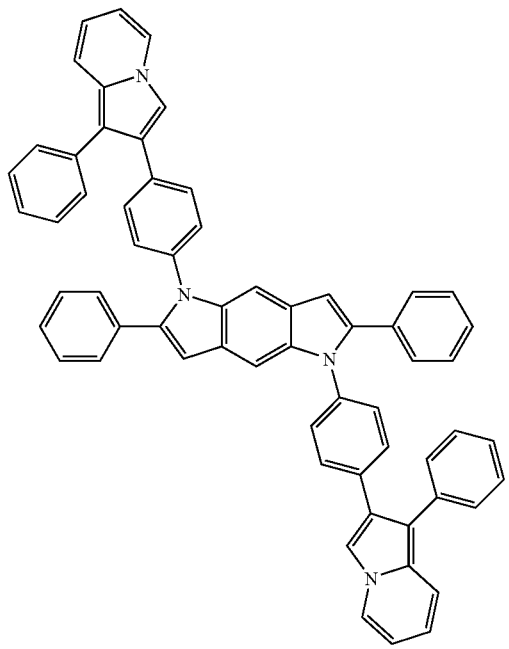
27
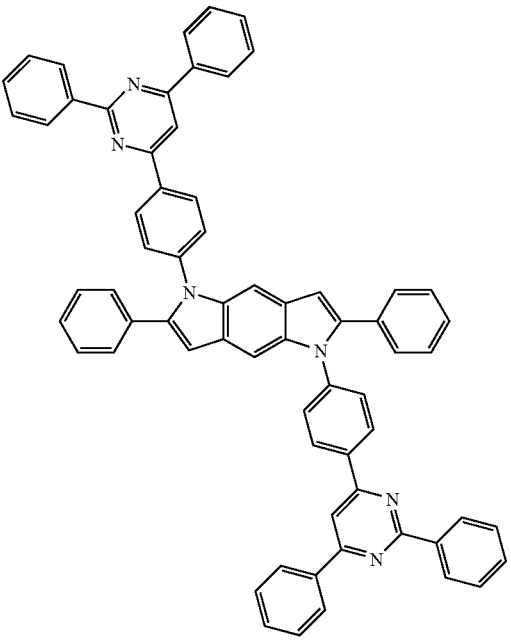
29
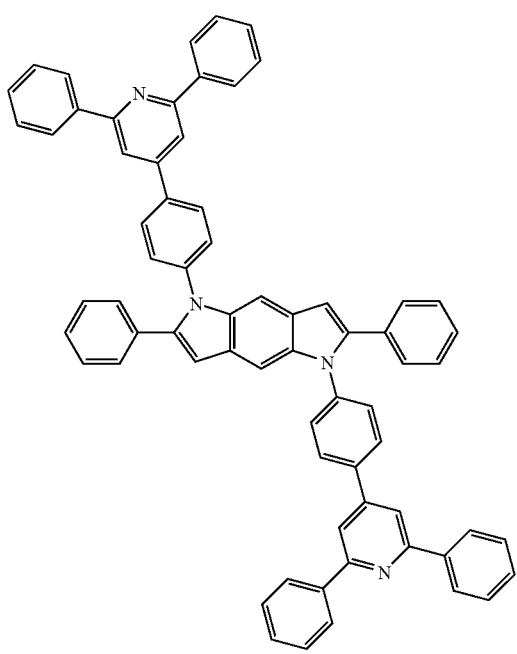
28
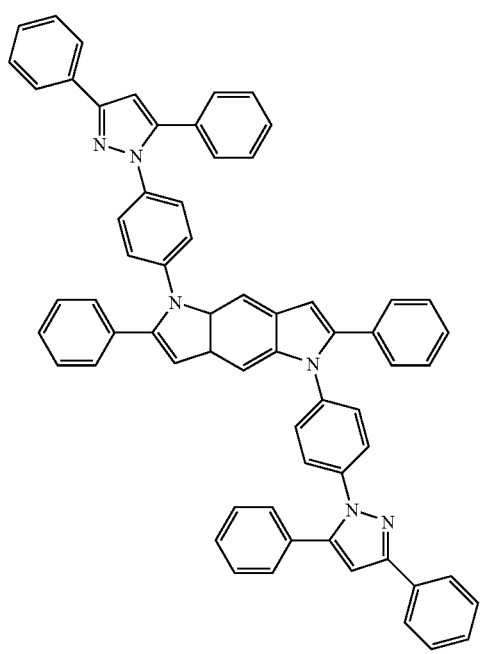
30

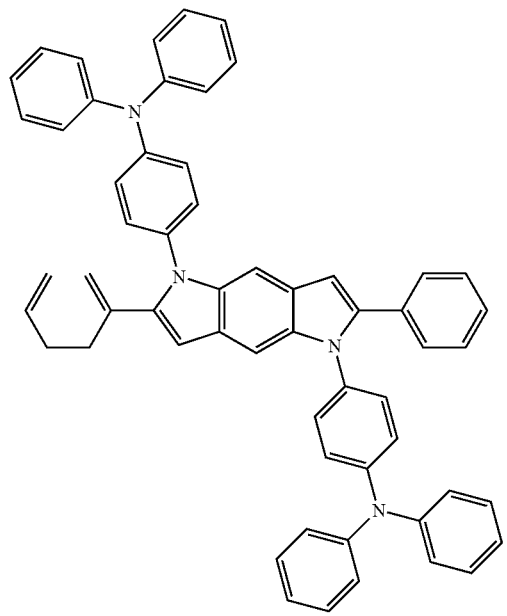
31
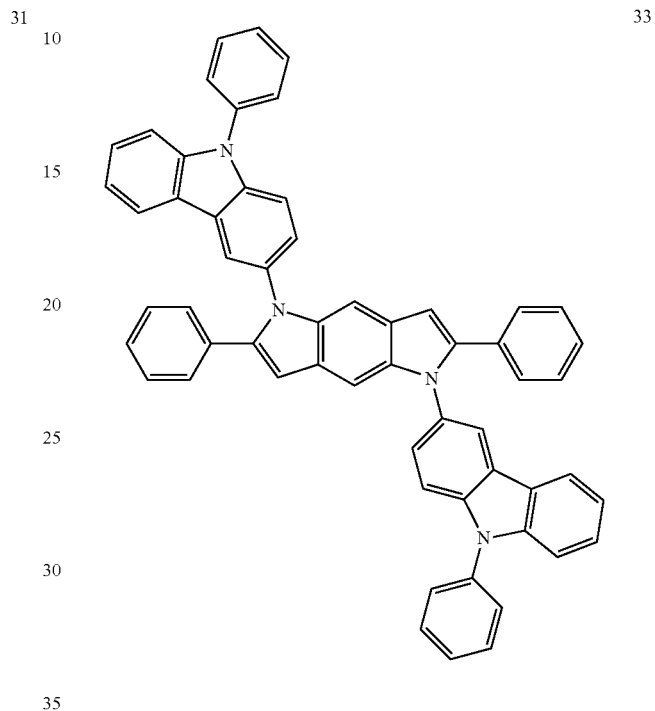
33
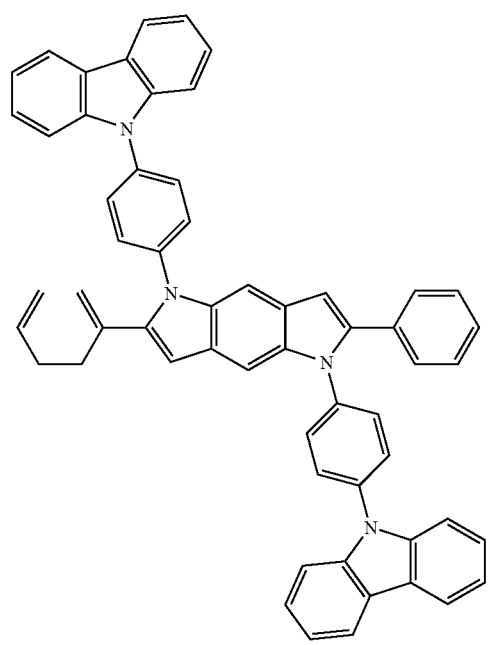
32
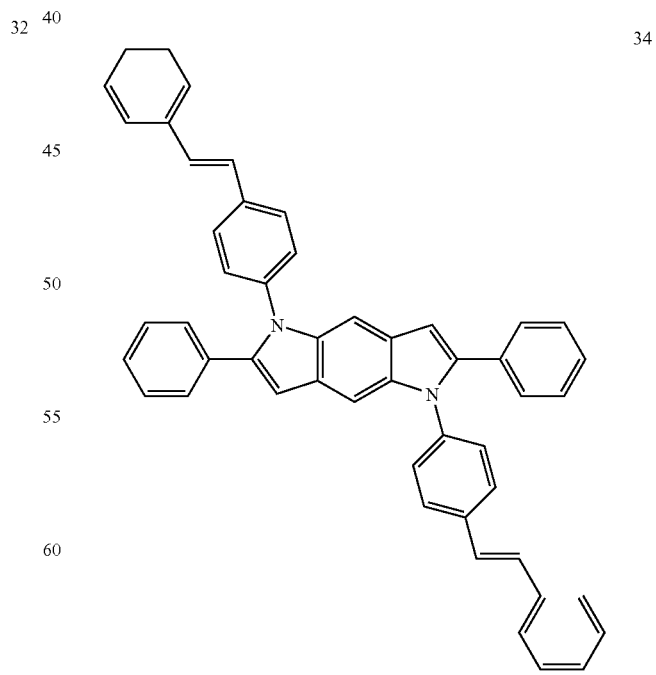
34

-continued
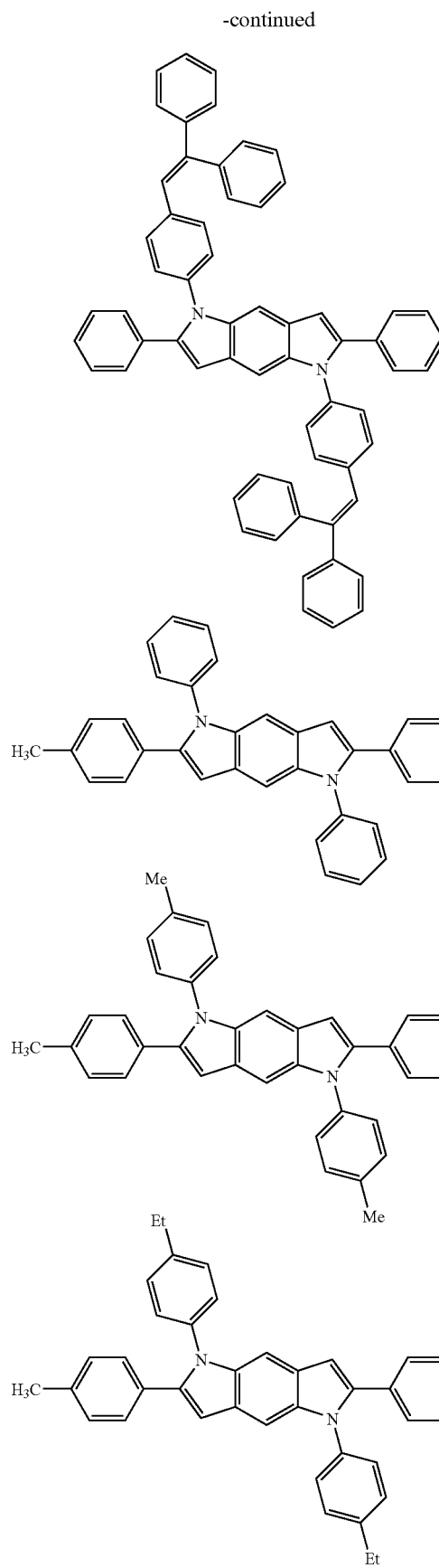
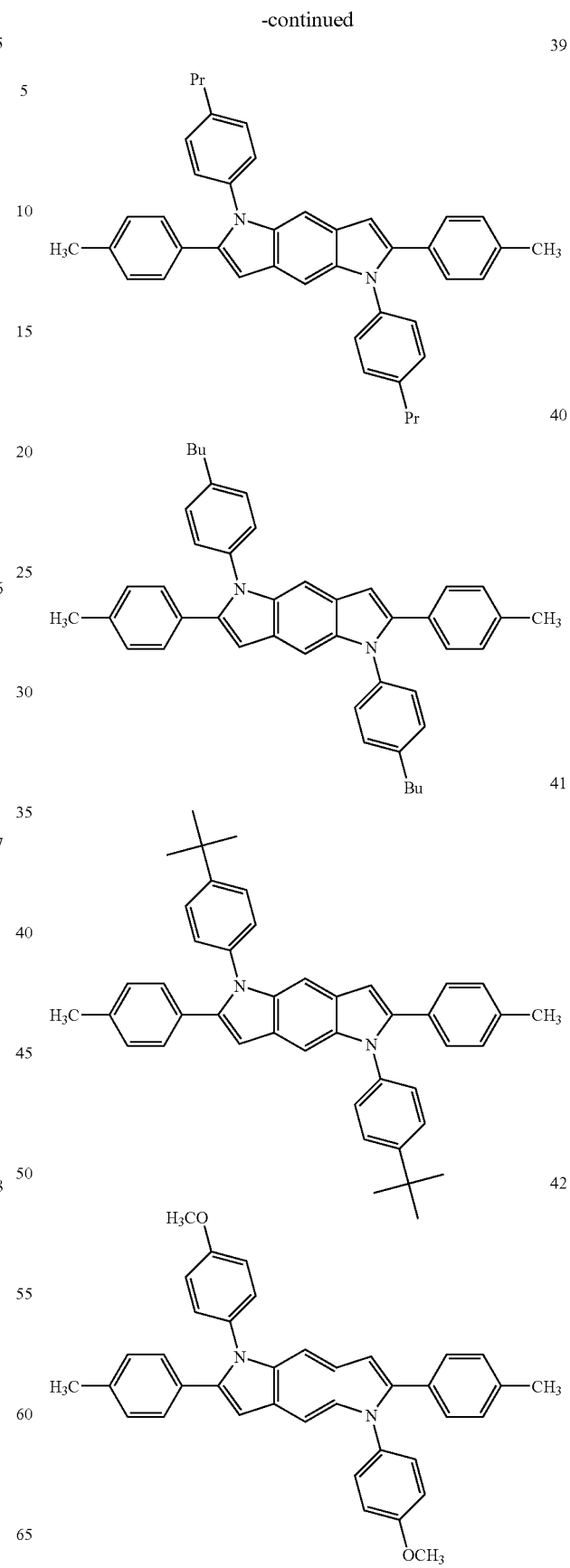

43
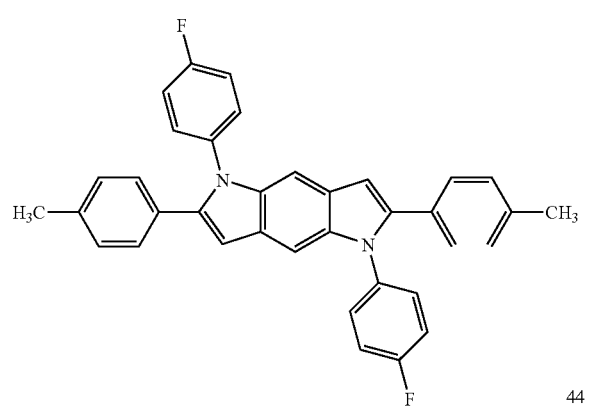
44
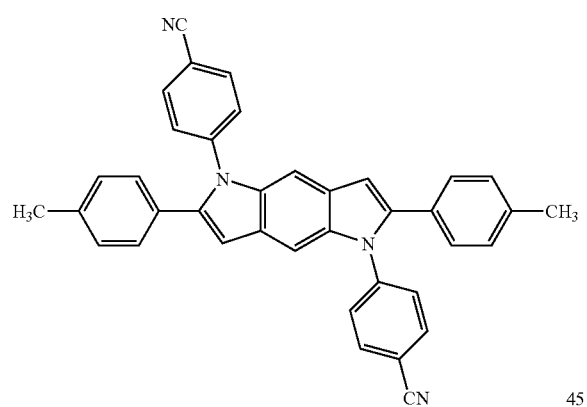
45
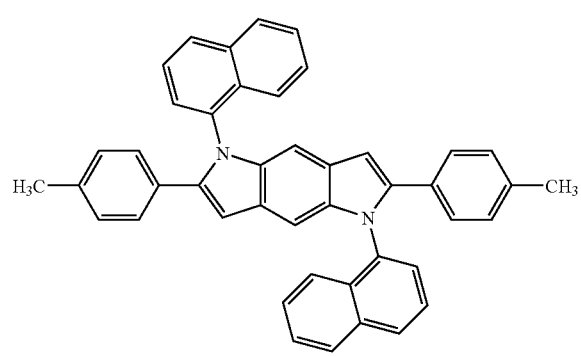
46
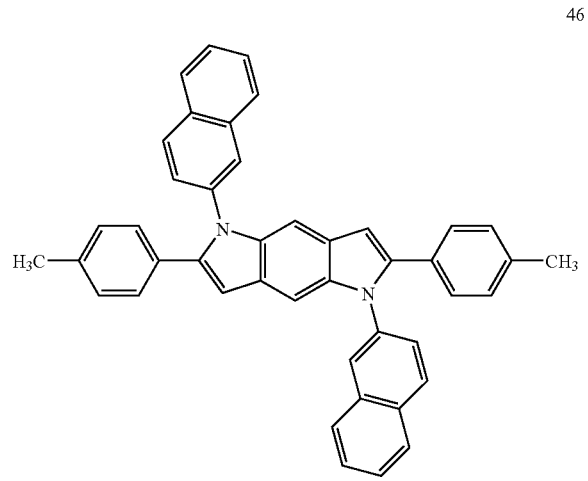
47
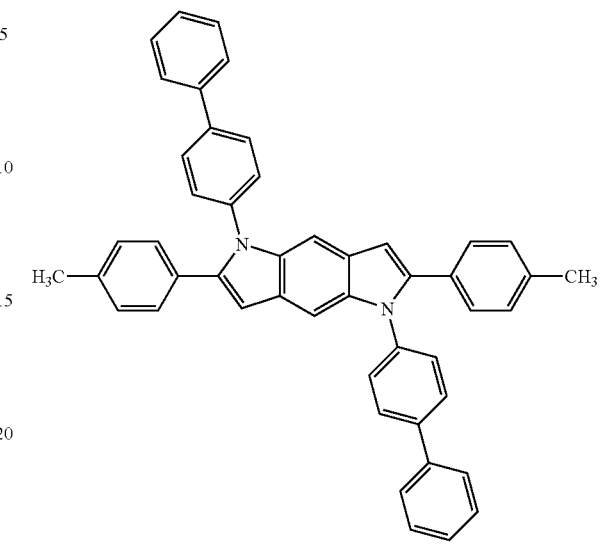
48
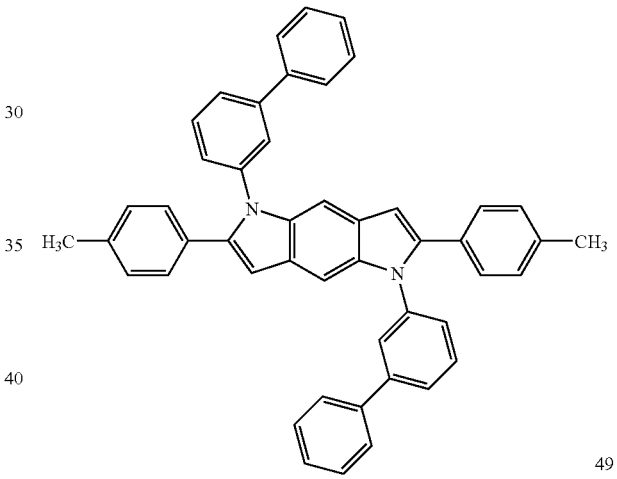
49
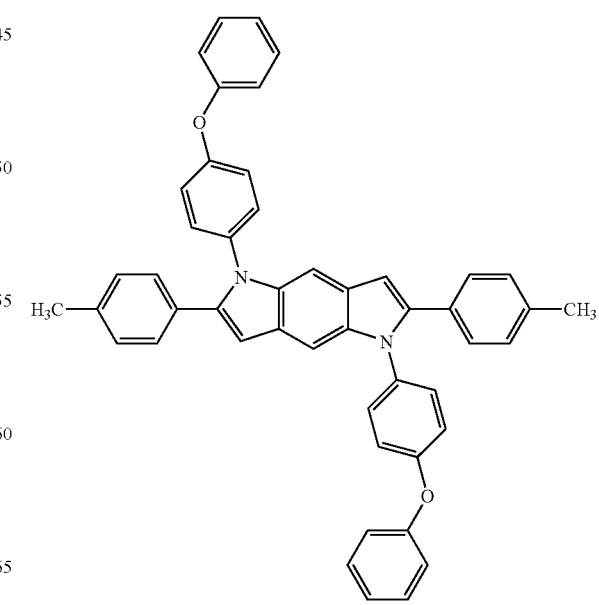

23
-continued
50
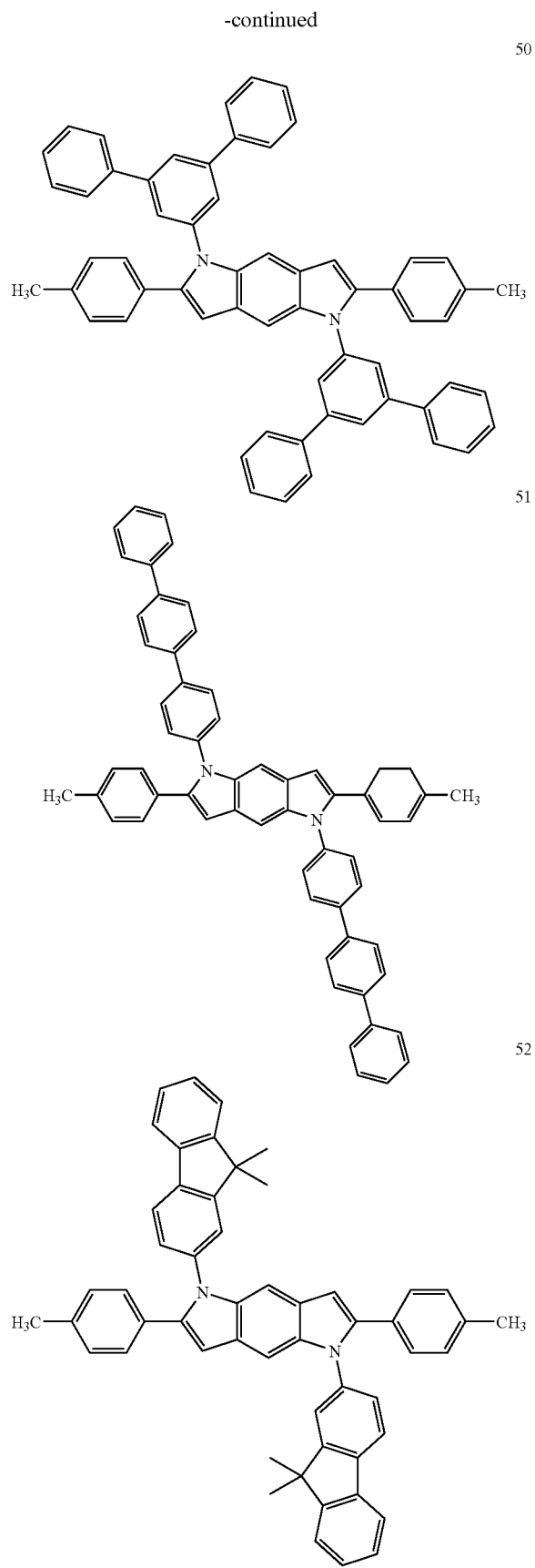
51
52
24
-continued
53
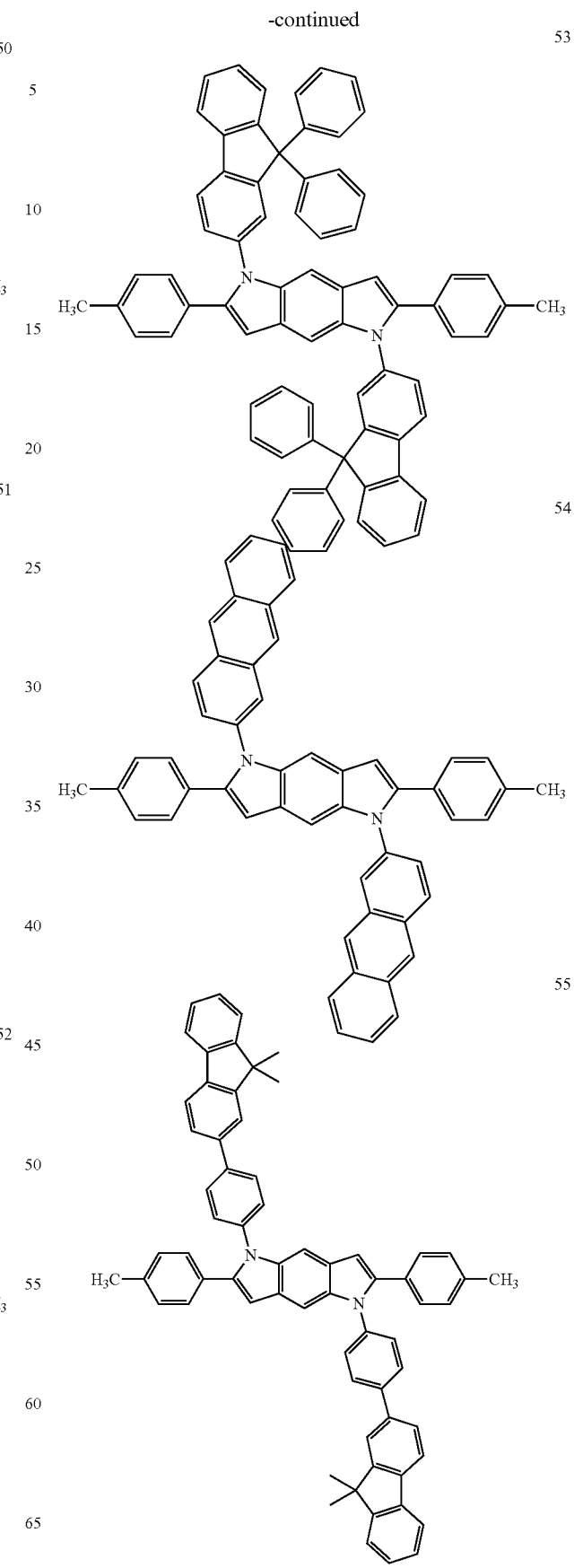
54
55

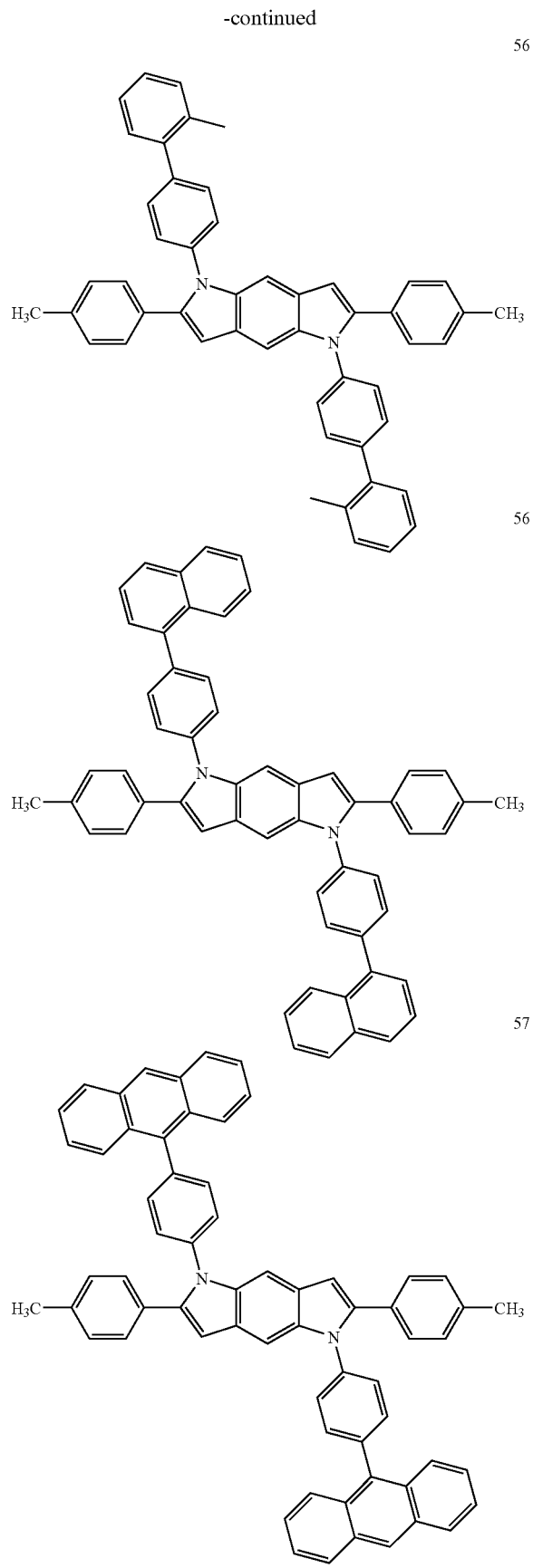
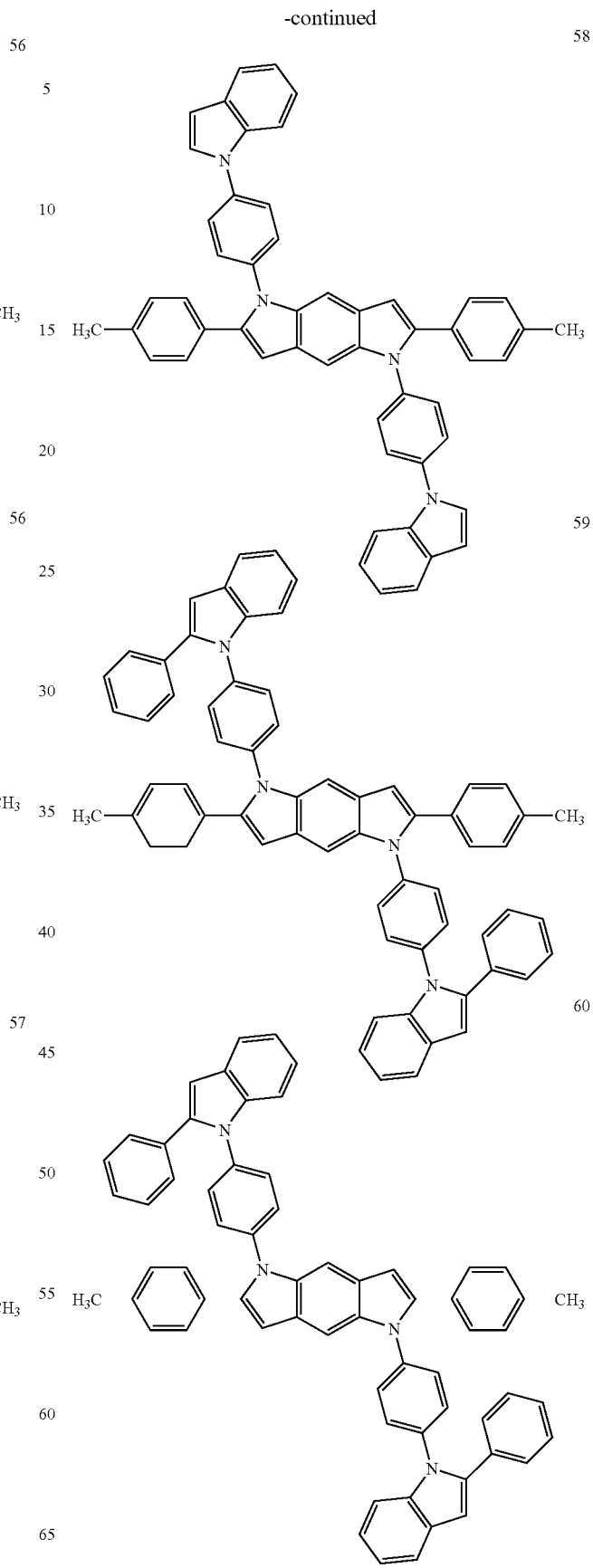

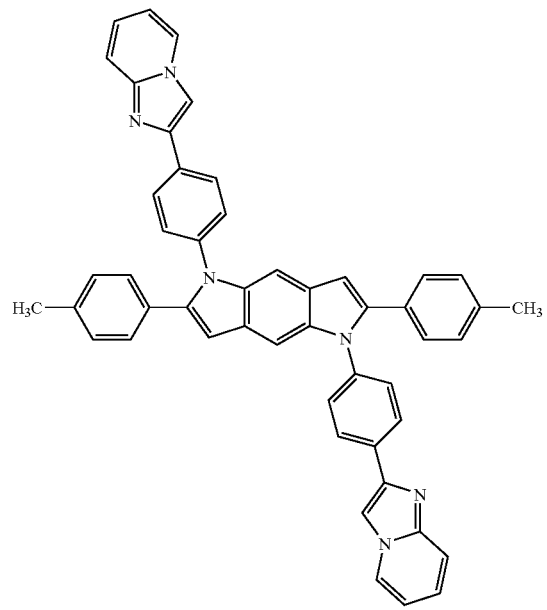
61
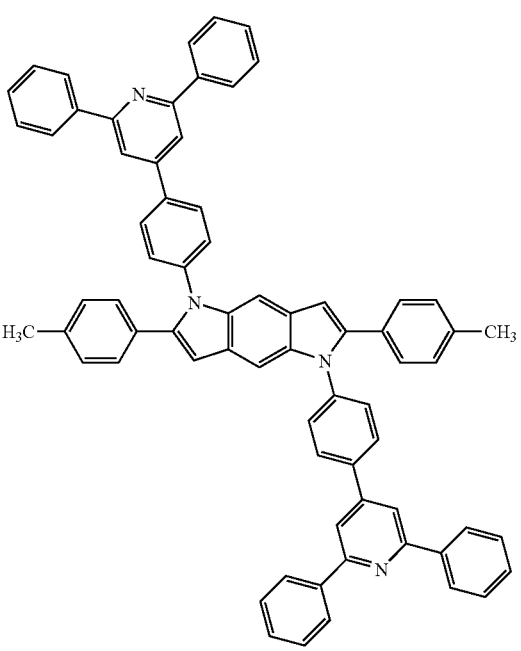
63
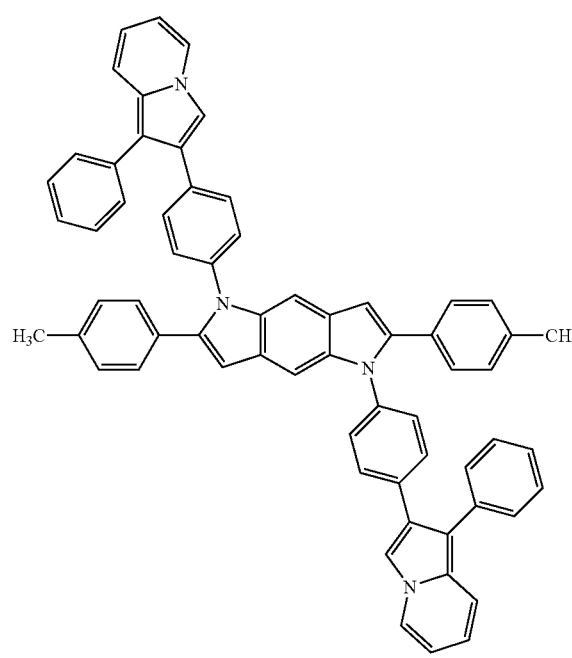
62
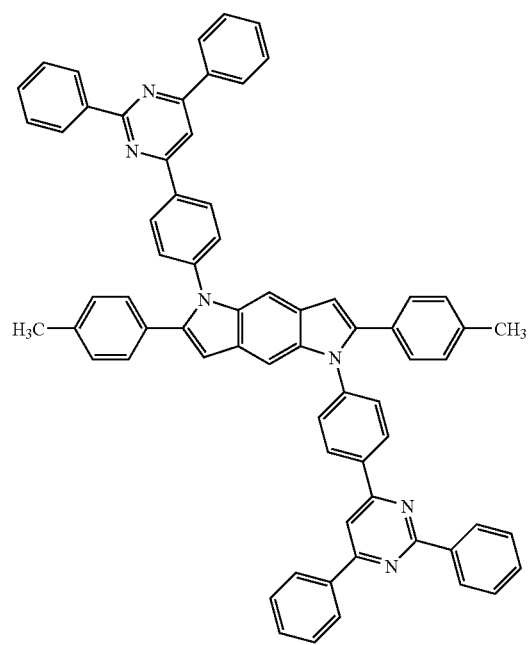
64

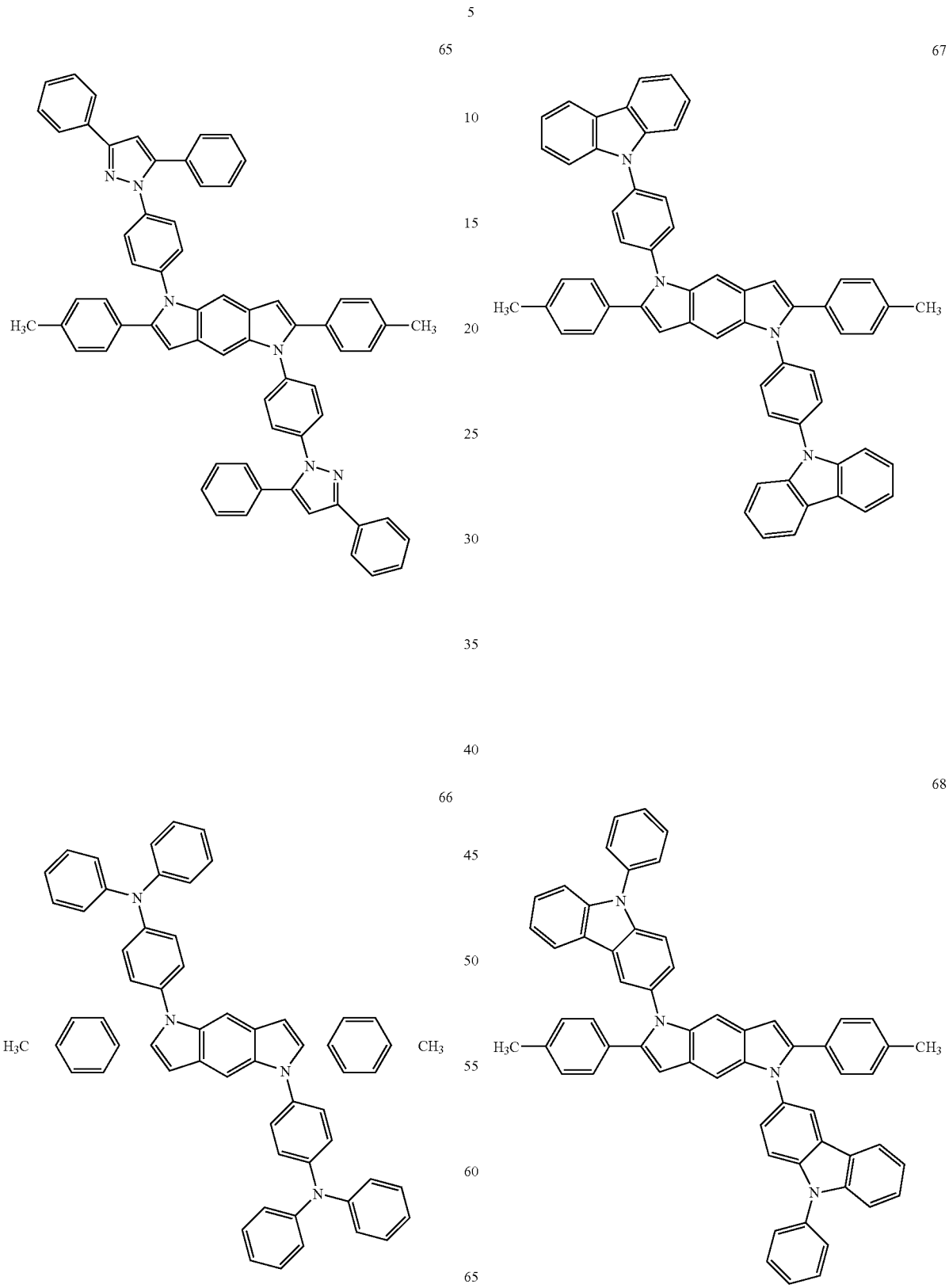

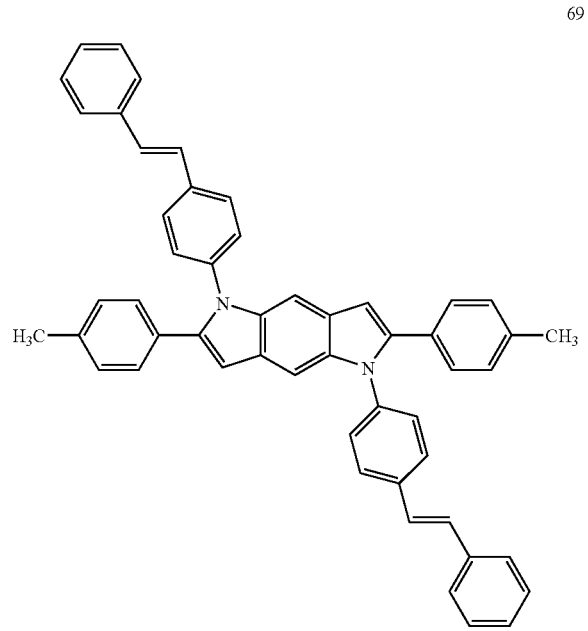
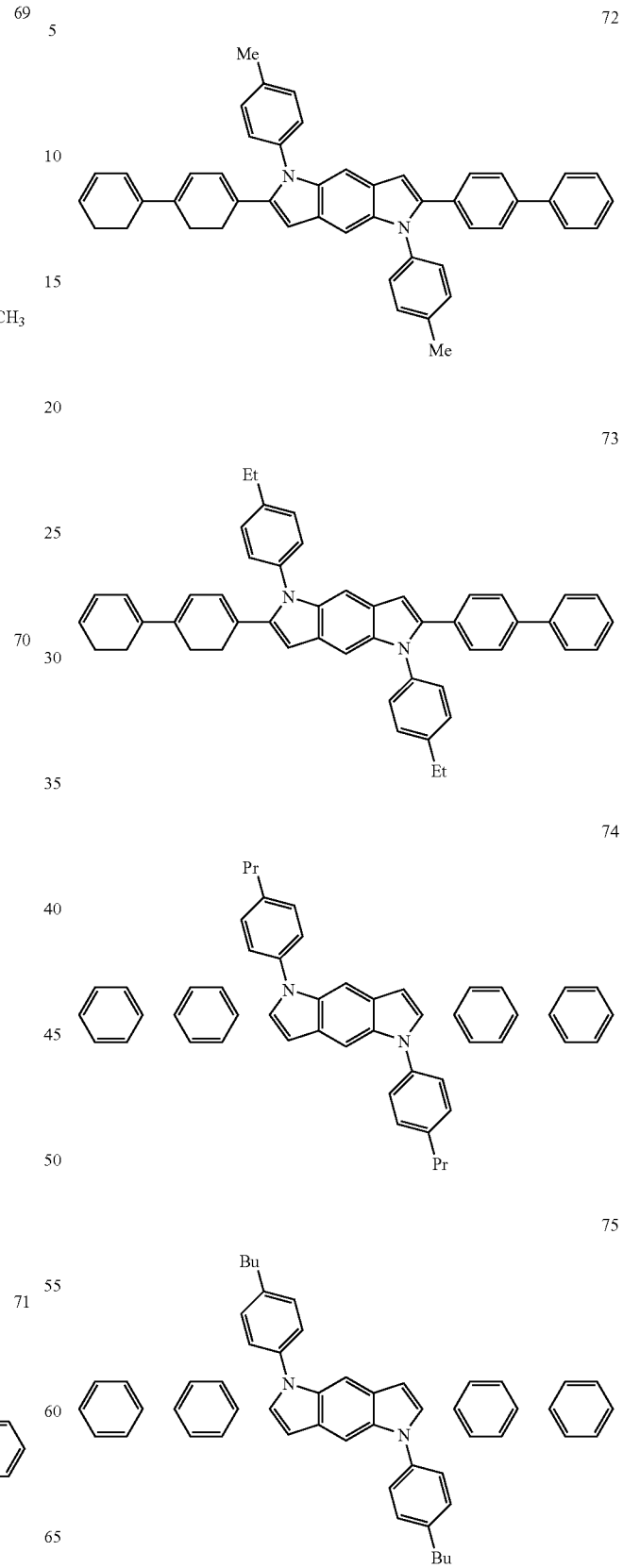

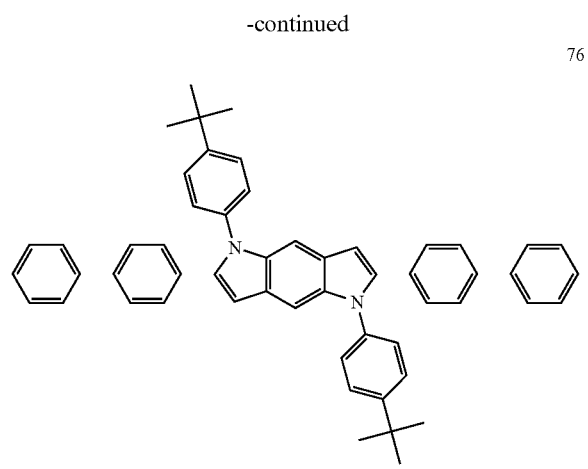
76
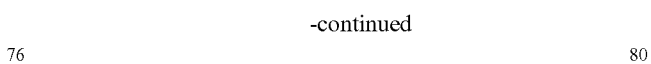
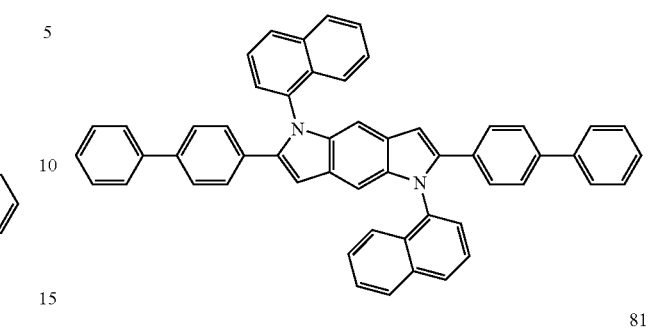
80
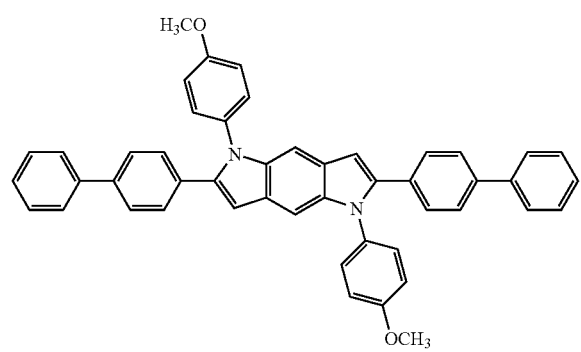
77
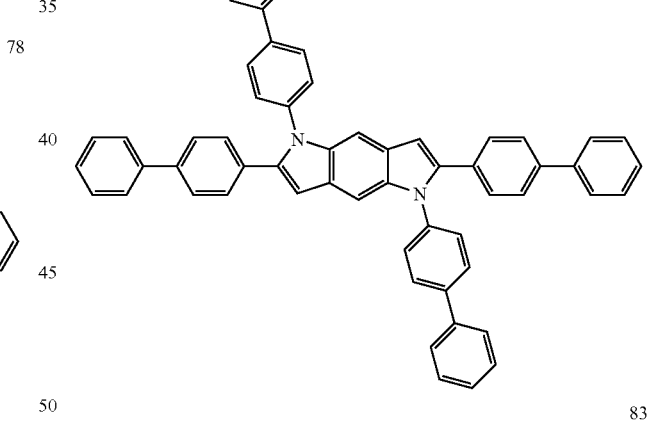
81
82
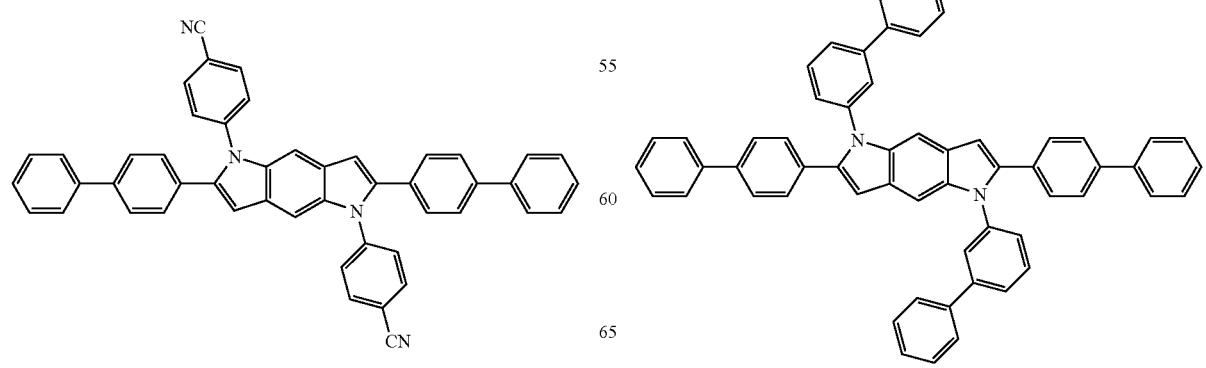
78
79
83

-continued
84
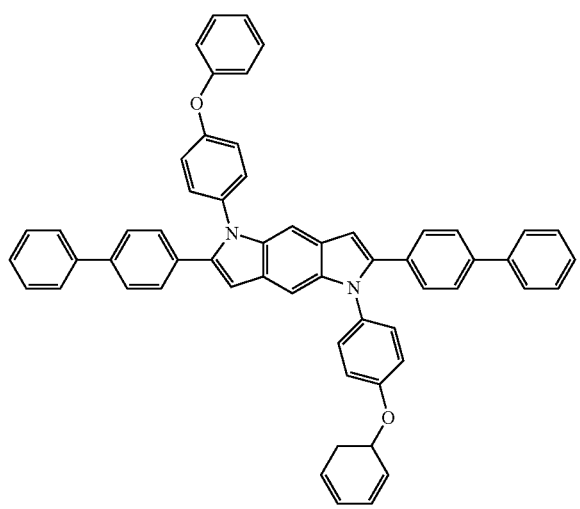
85
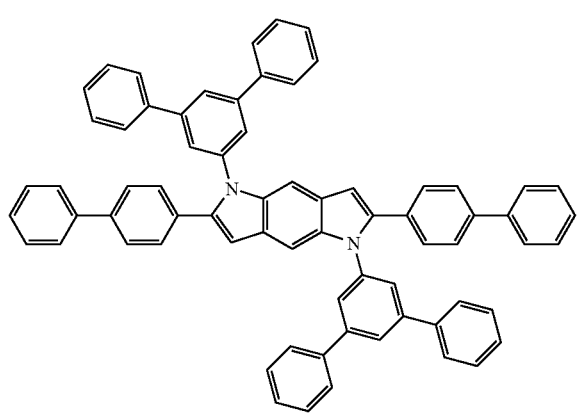
86
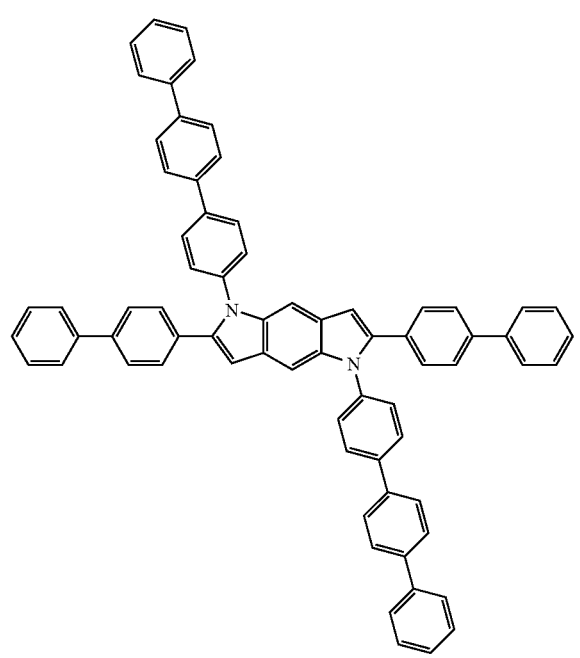
-continued
87
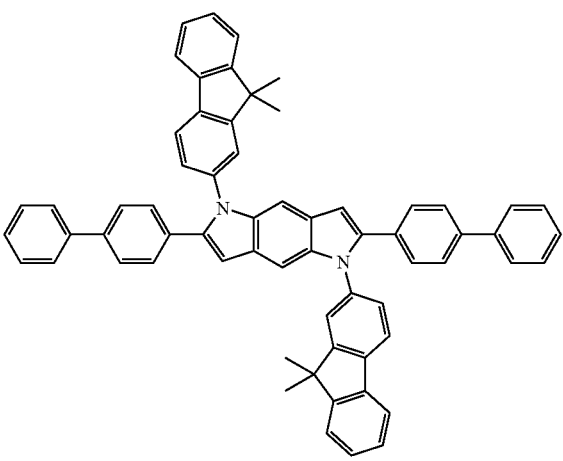
88
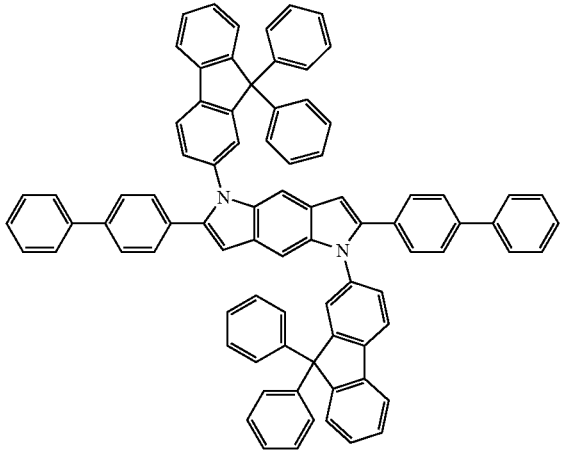
89
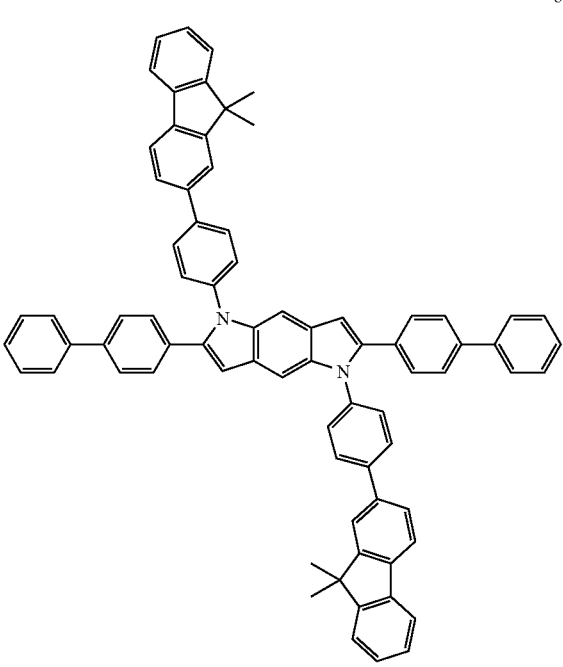

-continued
90
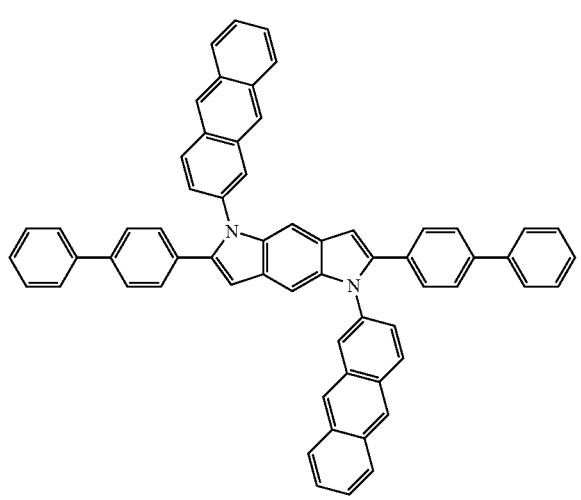
91
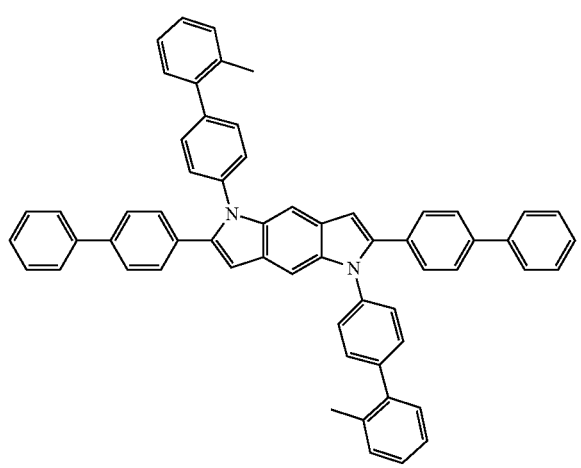
92
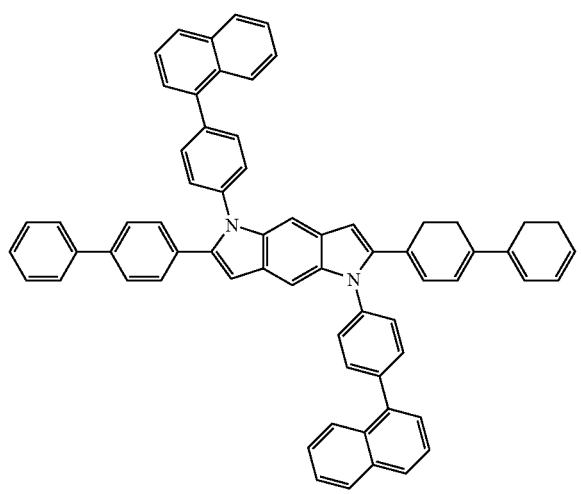
-continued
93
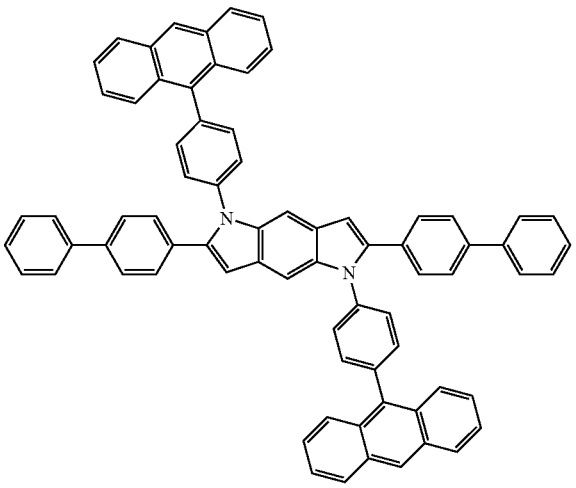
94
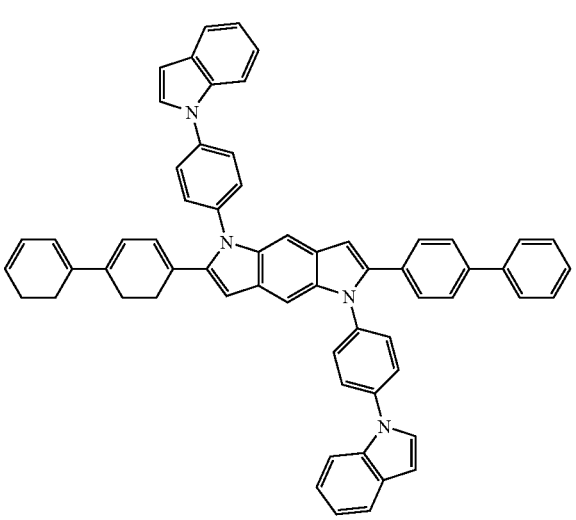
95

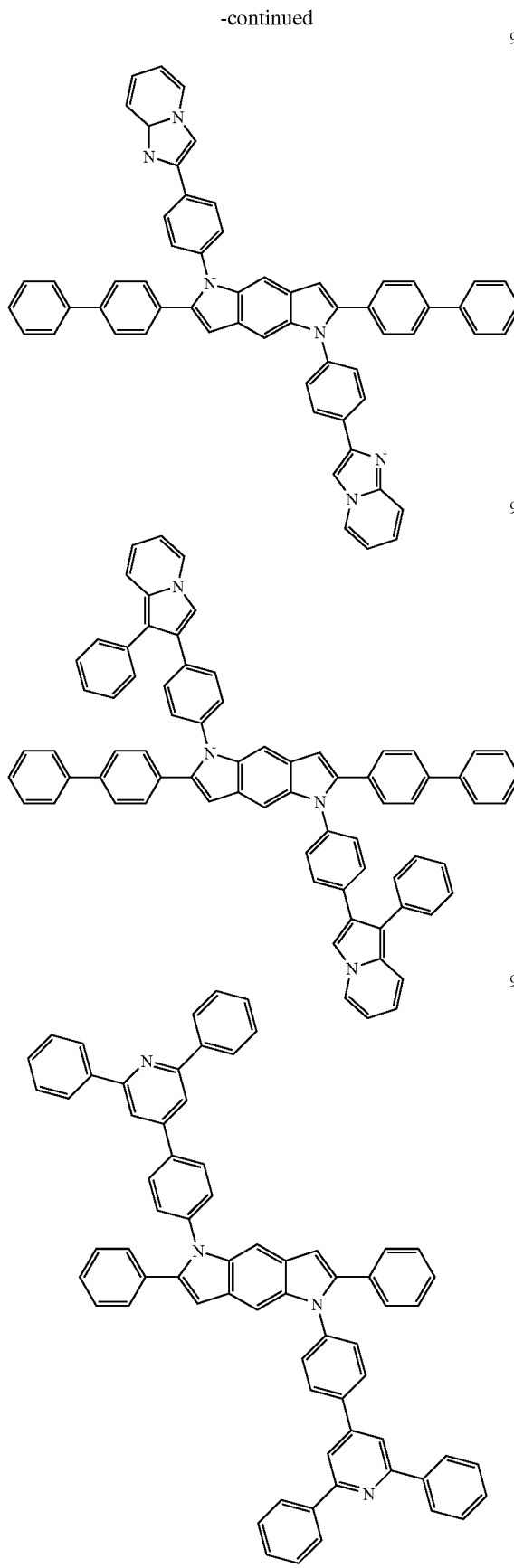
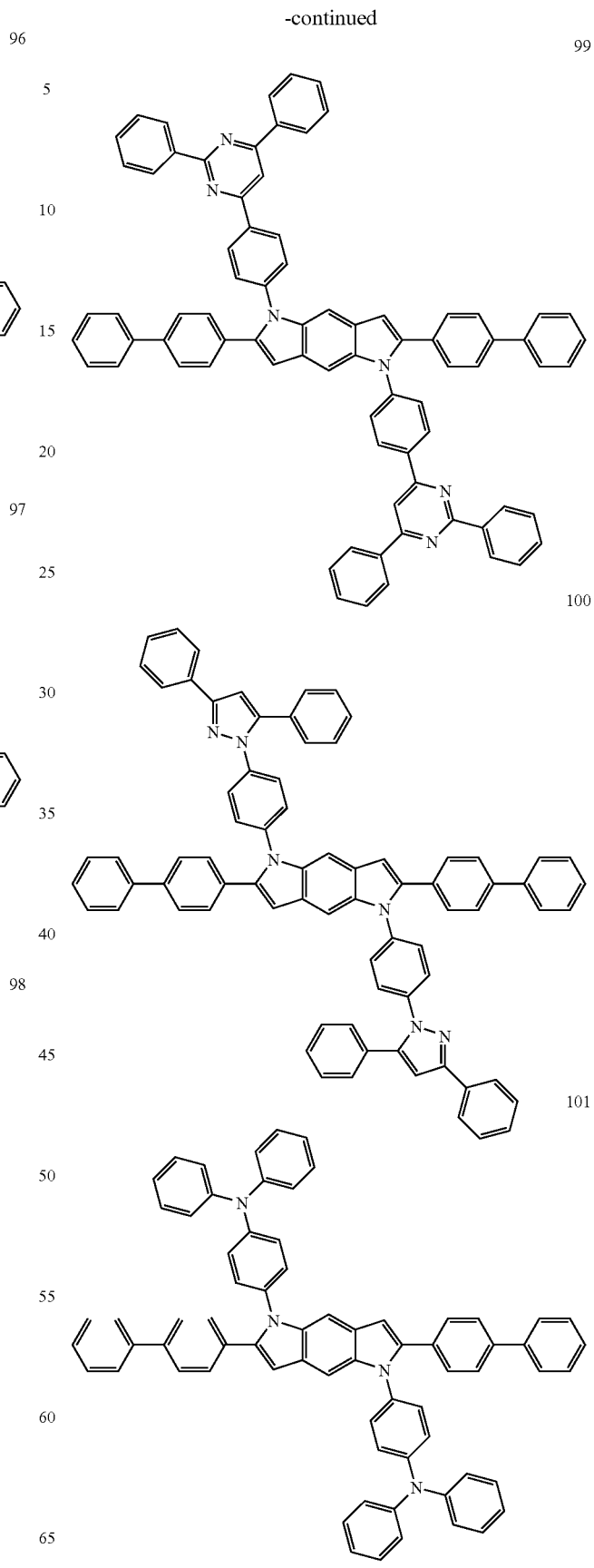

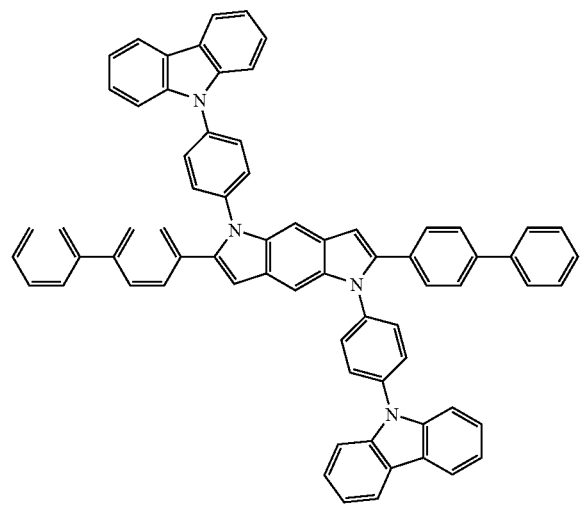
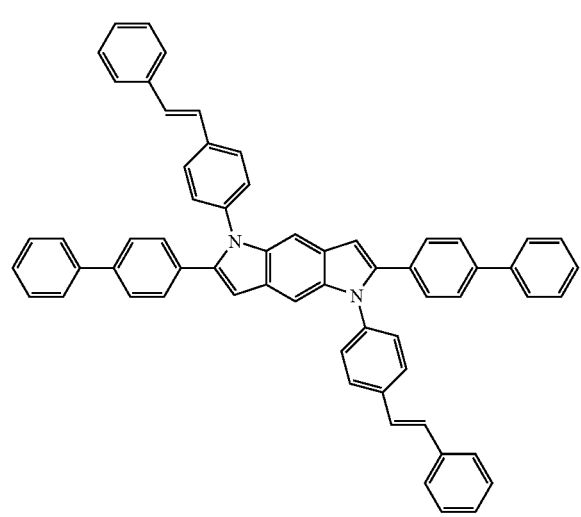
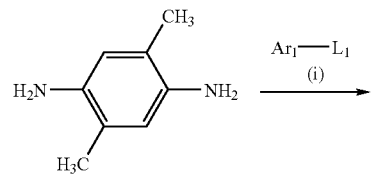
Hereinafter, a method of preparing a heterocyclic compound, according to aspects of the present invention, will be described in detail with reference to Reaction Scheme 1, below. However, Reaction Scheme 1 is for illustrative purposes only, and is not intended to limit the scope of the present invention.
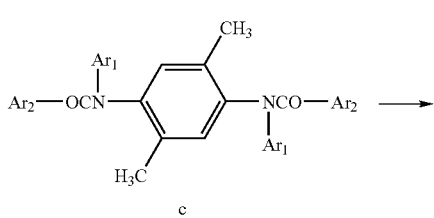

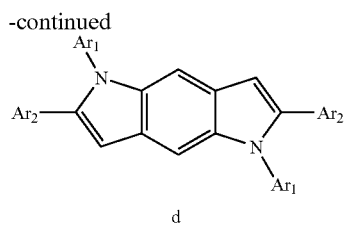

d

First, 2,5-dimethyl-1,4-phenylenediamine (a) and compound (i) were reacted in the presence of a base, to prepare intermediate (b). $L_1$ of the compound (i) was a leaving group, for example, a bromo group, or an iodo group. The prepared intermediate (b) was reacted with compound (ii), to prepare intermediate (c). In compound (ii), $L_2$ was a leaving group, selected from the group consisting of a chloro group, a bromo group, an anhydride, or a combination thereof. The prepared intermediate (c) was cyclization-reacted, at a high temperature and under a high pressure, to prepare compound (d).

An organic light emitting device, according to aspects of the present invention, includes a first electrode; a second electrode; and at least one organic layer interposed between the first electrode and the second electrode. The organic layer may include the heterocyclic compound represented by Formula 1, as described above.

The organic light emitting device can have a variety of structures. The organic layer, including the heterocyclic compound of Formula 1, may include an emission layer, a hole injection layer, a hole transport layer, or a single layer that performs both hole injecting and transporting. The emission layer includes a blue light emission layer in some aspects.

The organic light emitting device may have the structure shown in FIG. 1, including an anode, a hole injection layer (HIL), a hole transport layer (HTL), an emission layer (EML), an electron transport layer (ETL), an electron injection layer (EIL), and a cathode, in a stacked structure. The organic light emitting device can include one or more intermediate layers.

The compound of Formula 1 is particularly useful as a blue EML, due to its high color purity. An organic light emitting device including such an EML has excellent color purity and a large color gamut. The heterocyclic compound of Formula 1 has a high thermal resistance against heat generated in the organic layer, between the organic layers, and between the organic layer and the metal electrode, and is stable under such environments. Thus, the organic light emitting device has a high durability, and a long lifetime during storage and operation.

Hereinafter, a method of manufacturing an organic light emitting device, according to an exemplary embodiment of the present invention, will be described with reference to the organic light emitting device illustrated in FIG. 1. First, a first electrode (anode) is formed by depositing, by sputtering for example, a high work-function material on the substrate. The substrate, which can be any substrate that is used in conventional organic light emitting devices, and which has excellent mechanical strength, thermal stability, transparency, surface smoothness, is easily treated, and is waterproof. The substrate may be a glass substrate or a transparent plastic substrate, for example. The first electrode can be formed of ITO, IZO, $SnO_2$, ZnO, or any highly conductive transparent material.

Then, the HIL can be formed on the first electrode, by for example, vacuum deposition, spin coating, casting, langmuir blodgett (LB), or the like. Any known HIL forming material can be used. For example, 1,3,5-tricarbazolylbenzene, 4,4'-biscarbazolylbiphenyl, polyvinyl carbazole, m-biscarbazolylphenyl, 4,4'-biscarbazolyl-2,2'-dimethylbiphenyl, 4,4',4''-tri(N-carbazolyl)triphenylamine, 1,3,5-tri(2-carbazolylphenyl)benzene, 1,3,5-tris(2-carbazolyl-5-methoxyphenyl)benzene, bis(4-carbazolylphenyl)silane, N,N'-bis(3-methylphenyl)-N,N'-diphenyl-[1,1-biphenyl]-4,4'diamine (TPD), N,N'-di(naphthalene-1-yl)-N,N'-diphenyl benzydine (α-NPD), N,N'-diphenyl-N,N'-bis(1-naphthyl)-(1,1'-biphenyl)-4,4'-diamine (NPB), poly(9,9-dioctylfluorene-co-N-(4-butylphenyl)diphenylamine) (TFB), and poly(9,9-dioctylfluorene-co-bis-N,N-phenyl-1,4-phenylenediamine) (PFB) can be used.

When the HIL is formed by vacuum deposition, vacuum deposition conditions may vary, according to the compound that is used to form the HIL, the desired structure, and thermal properties of the HIL. In general, however, the vacuum deposition may be performed at a deposition temperature of 50-500° C., under a pressure of $10^{-8}$-$10^{-3}$ torr, at a deposition speed of 0.01-100 Å/sec, to a layer thickness of 10 Å-5 μm.

When the HIL is formed by spin coating, coating conditions may vary, according to a compound that is used to form the HIL, and the desired structure and thermal properties of the HIL. In general, however, the coating speed may be in the range of about 2000 to 5000 rpm. The temperature for a heat treatment, which is performed to remove a solvent after coating, may be in the range of about 80 to 200° C.

The HTL can also be formed using a known method, such as vacuum deposition, spin coating, casting, or LB. When the HTL is formed by vacuum deposition or spin coating, the conditions for deposition and coating are similar to those for the formation of the HIL, although the conditions may vary, according to the material that is used to form the HTL.

Any known material that is commonly used to form an HTL can be used to form the HTL. Examples of the material include: carbazole derivatives, such as N-phenylcarbazole and polyvinylcarbazole; and conventional amine derivatives including a condensed aromatic ring, such as N,N'-bis(3-methylphenyl)-N,N'-diphenyl-[1,1-biphenyl-4,4'-diamine (TPD), and N,N'-di(naphthalene-1-yl)-N,N'-diphenyl benzydine (α-NPD).

Red, green, and blue EMLs (EML regions) can be formed on the HIL and the HTL. Any material, selected from known host materials and known dopant materials, can be used to form the EML. For example, DCM1, DCM2, Eu(thenoyltrifluoroacetone)3 (Eu(TTA)3), and butyl-6-(1,1,7,7,-tetramethyljulolidyl-9-enyl)-4H-pyran (DCJTB) can be used to form the red EML. Alternatively, a dopant such as DCJTB can be deposited with Alq3, Alq3 and rubrene can be co-deposited, and a dopant can be deposited thereon, or dopants such as BTPIr or RD 61 can be deposited with 4,4'-N—N'-dicarbazole-biphenyl (CBP), to form the red EML, but the present invention is not limited to the above-described examples.

For example, Coumarin 6, C545T, quinacridone, and Ir(ppy)$_3$ can be used to form the green EML. Alternatively, a dopant, such as Ir(ppy)$_3$, can be deposited with CBP, or a dopant, such as a coumarin-based material, can be deposited with Alq3 as a host, to form the green EML, but the present invention is not limited to the above-described examples. Examples of the coumarin-based dopant may include C314S, C343S, C7, C7S, C6, C6S, C314T, and C545T.

The heterocyclic compound of Formula 1 can only be used to form the blue EML region. Alternatively, oxadiazole dimer dyes (Bis-DAPOXP), spiro compounds (Spiro-DPVBi, Spiro-6P), triarylamine compounds, bis(styryl) amine (DPVBi, DSA), CzTT, Anthracene, TPB, PPCP, DST, TPA, OXD-4, BBOT, AZM-Zn, and BH-013X (Idemitsu Corporation), which is an aromatic hydrocarbon compound containing a naphthalene moiety, can be used to form the blue EML. Alternatively, a dopant such IDE 105 (Idemitsu Corporation) can be deposited on IDE 140 (Idemitsu Corporation), to form the blue EML.

The thickness of the EML may be in the range of 200 to 500 Å, and in some embodiments 300 to 400 Å. The thickness of the EML of each of R, G, and B regions may be identical or different. When the thickness of the EML is less than 200 Å, the lifetime of the device may be decreased. On the other hand, when the thickness of the EML is greater than 500 Å, the driving voltage may be increased.

The EML may be formed using a known method, such as vacuum deposition, spin coating, casting, and LB. When the EML is formed by vacuum deposition or spin coating, the conditions for deposition and coating are similar to those for the formation of the HIL, although the conditions may vary, according to the material that is used to form the EML.

A hole blocking layer (HBL) (not shown) can optionally be formed on the EML, by vacuum depositing or spin coating a material that is used to form the HBL. The material should transport electrons, and have an ionization potential higher than the EML materials. Examples of the material may include bis(2-methyl-8-quinolato)-(p-phenylphenolato)-aluminum (Balq), bathocuproine (BCP), and tris(N-aryl benzimidazole) (TPBI), but are not limited thereto.

The thickness of the HBL may be in the range of 30 to 60 Å, and in some embodiments 40 to 50 Å. When the thickness of the HBL is less than 30 Å, a proper hole blocking capability may not be obtained. On the other hand, when the thickness of the HBL is greater than 60 Å, the driving voltage of the device may be increased.

The HBL can be formed using a known method, such as vacuum deposition, spin coating, casting, LB, or the like. When the HBL is formed by vacuum deposition or spin coating, conditions for deposition and coating are similar to those for formation of the HIL, although the conditions may vary, according to the material that is used to form the HBL.

An ETL can be optionally formed by vacuum depositing or spin coating a material on the EML or the HBL. The material may be Alq3, but is not limited thereto.

The thickness of the ETL may be in the range of 100 to 400 Å, and in some embodiments 250 to 350 Å. When the thickness of the ETL is less than 100 Å, a proper charge balance may not be maintained, since electrons are transported too fast. On the other hand, when the thickness of the ETL is greater than 400 Å, the driving voltage of the device may be increased.

The ETL can be formed using a known method, such as vacuum deposition, spin coating, casting, LB, or the like. When the ETL is formed by vacuum deposition or spin coating, conditions for deposition and coating are similar to those for formation of the HIL, although the conditions may vary, according to the material that is used to form the ETL.

The EIL may be formed by vacuum deposition or spin coating a material on the ETL. The material may be $BaF_2$, LiF, NaCl, CsF, $Li_2O$, BaO, Liq, or the like, but is not limited thereto.

The thickness of the EIL may be in the range of 2 to 100 Å, of in the range of 2 to 5 Å. In some embodiments the thickness is in the range of 2 to 4 Å. When the thickness of the EIL is less than 2 Å, a proper electron injecting capability may not be obtained. On the other hand, when the thickness of the EIL is greater than 10 Å, the driving voltage of the device may be increased.

The EIL can be formed using a known method, such as vacuum deposition, spin coating, casting, LB, or the like. When the EIL is formed by vacuum deposition or spin coating, conditions for deposition and coating are similar to those for formation of the HIL, although the conditions may vary, according to the material that is used to form the EIL.

Finally, a second electrode (cathode) is formed on the EIL, by deposition, thereby completing the manufacture of the organic light emitting device. The second electrode can be a transparent metal oxide with excellent conductivity, such as ITO, IZO, $SnO_2$, and ZnO. Optionally, Li, Mg, Al, Al—Li, Ca, Mg—In, Mg—Ag, and Ca—Al can be used to form a thin film on the second electrode. Thus, the second electrode can include a reflective electrode, and a semitransparent electrode, or a transparent electrode. The material used to form the second electrode is not limited to the above-described examples.

Hereinafter, aspects of the present invention will be described with reference to the following Synthesis Examples of heterocyclic compounds represented by Formula 1, and Preparation Examples of an organic light emitting device. However, the Examples are not intended to limit the scope of the present invention.

Synthesis Example 1

Preparation of Compound 2

Compound 2 was synthesized through Reaction Scheme 2 below.

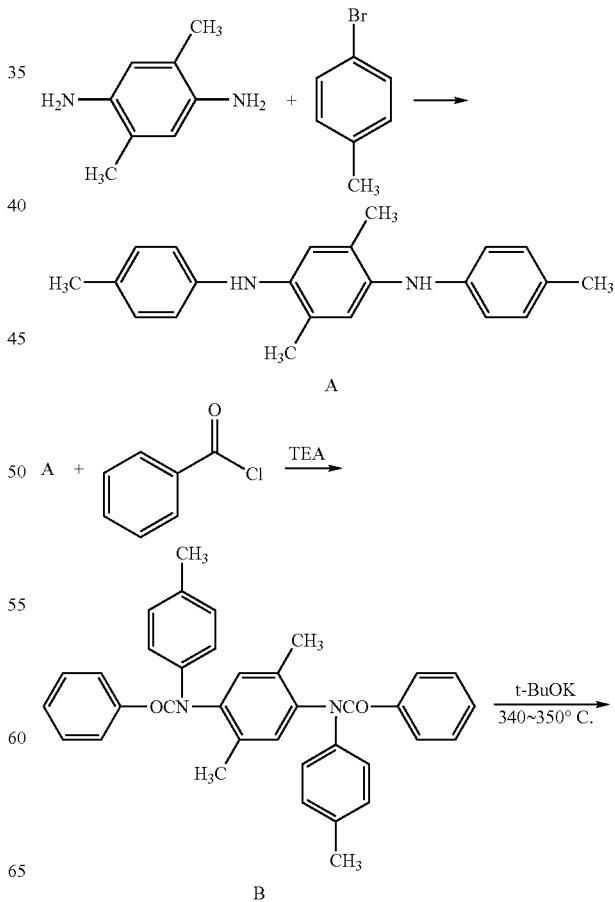

-continued

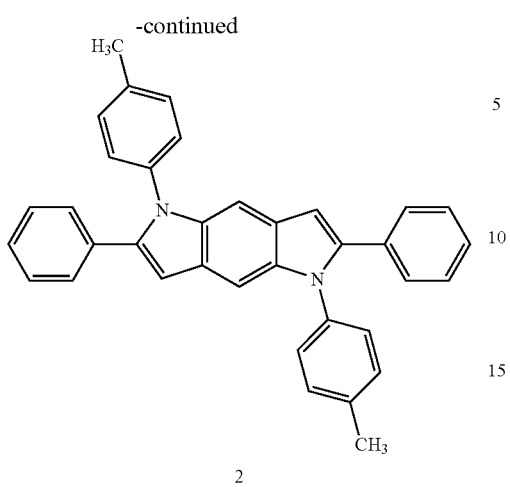

2

(1) Synthesis of Intermediate A 1.36 g (10.0 mmol) of 2,5-dimethyl-1,4-phenylenediamine and 4.10 g (24.0 mmol) of 4-bromotoluene were dissolved in 50 Ml of toluene. 2.88 g (30.0 mmol) of sodium t-butoxide, 0.388 g (0.40 mmol) of Pd(dba)$_2$ and 0.08 g (0.40 mmol) of tri-t-butylphosphine((t-Bu)$_3$P) were added to the solution, and the mixture was stirred at 80° C., for 5 hours. The resultant mixture was cooled to room temperature, and then 50 Ml of water was added thereto. The resultant mixture was subjected to extraction three times, using 20 Ml of ethyl ether. A collected organic layer was dried using magnesium sulfate, and the residue (prepared by removing the solvent) was separated and purified using a silica gel column chromatography, to obtain 2.15 g of Intermediate A (Yield: 68%).

$^1$H NMR (CDCl$_3$, 400 MHz) δ (ppm) 7.24-7.33 (m, 4H), 7.09 (s, 2H), 6.85-6.78 (m, 4H), 5.25 (bs, 2H), 2.32 (s, 6H), 2.17 (s, 6H); $^{13}$C NMR (CDCl$_3$, 100 MHz) δ (ppm) 145.8, 133.2, 128.5, 127.8, 123.8, 122.5, 116.8, 17.6, 15.7.

(2) Synthesis of Intermediate B 3.16 g (10.0 mmol) of Intermediate A was dissolved in 50 Ml of dichloromethane, and 4.0 Ml of triethylamine was the added thereto. The mixture was cooled in an ice bath, and 4.21 g (30.0 mmol) of benzoyl chloride was dropped thereto. The resultant was stirred at 30° C., for 1 hour, and 50 Ml of water was added thereto. Then, the resultant was subject to extraction three times, using 50 Ml of ethyl ether. A collected organic layer was dried using magnesium sulfate, and the residue prepared by removing the solvent was recrystallized in DMF. The resultant was filtered, while washing with acetone, to obtain 2.99 g of white solid Intermediate B (Yield: 57%).

$^1$H NMR (CDCl$_3$, 400 MHz) δ (ppm) 8.11-8.09 (d, 2H), 7.48-7.46 (m, 4H), 7.27-6.89 (m, 14H), 2.17 (s, 6H), 2.10 (s, 6H); $^{13}$C NMR (CDCl$_3$, 100 MHz) δ (ppm) 170.4, 143.3, 135.5, 133.7, 130.0, 129.3, 128.9, 128.8, 127.8, 125.5, 120.9, 118.2, 18.0, 17.3.

(3) Synthesis of Compound 2

A mixture, prepared by sufficiently pulverizing and stirring 5.24 g (10 mmol) of Intermediate B and 12.2 g (100 mmol) of potassium t-butoxide, was added to an autoclave, and reacted at 340-350° C., at 5 MPa, for 2 hours. When the reaction was completed, the resultant tar was cooled to room temperature. The tar was pulverized, neutralized, filtered using distilled water, and dried. The residue was purified in a soxhlet device, using acetone, for 2 days, to obtain 0.97 g of yellow Compound 2 (Yield: 20%).

$^1$H NMR (CDCl$_3$, 400 MHz) δ (ppm) 7.46 (s, 2H), 7.31-7.18 (m, 18H), 6.74 (s, 2H), 2.41 (s, 3H); $^{13}$C NMR (CDCl$_3$, 100 MHz) δ (ppm) 141.4, 137.3, 136.9, 136.6, 133.1, 129.9, 128.8, 128.1, 128.0, 127.0, 126.4, 103.3, 99.8, 22.1.

Synthesis Example 2

Preparation of Compound 12

Compound 12 was synthesized through Reaction Scheme 3 below.

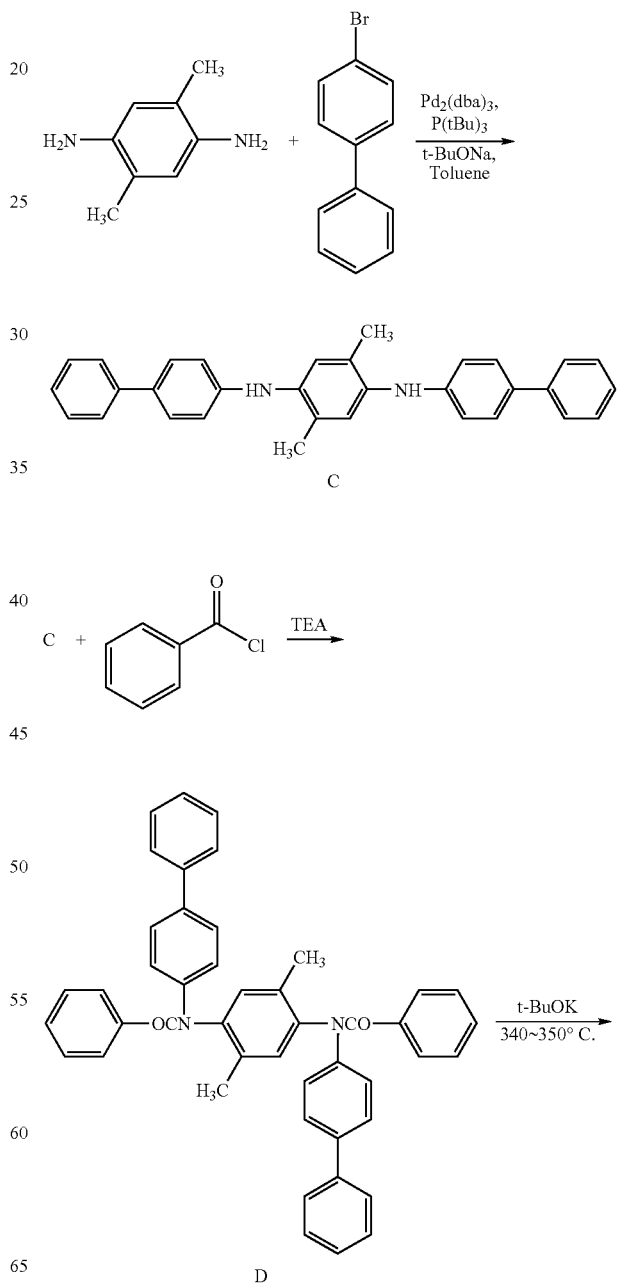

-continued

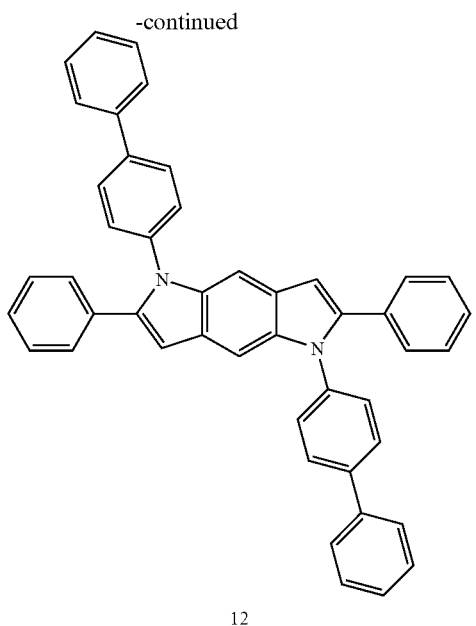

12

(1) Synthesis of Intermediate C 1.36 g (10.0 mmol) of 2,5-dimethyl-1,4-phenylenediamine and 5.13 g (22.0 mmol) of 4-bromobiphenyl was dissolved in 50 Ml of toluene. 2.88 g (30.0 mmol) of sodium t-butoxide, 0.388 g (0.40 mmol) of Pd(dba)$_2$, and 0.08 g (0.40 mmol) of tri-t-butylphosphine((t-Bu)$_3$P) were added to the solution, and the mixture was stirred at 80° C., for 5 hours. The resultant mixture was cooled to room temperature, and then 50 Ml of water was added thereto, and the resultant was subjected to extraction three times, using 20 Ml of ethyl ether. A collected organic layer was dried using magnesium sulfate, and the residue prepared by removing the solvent was separated and purified, using a silica gel column chromatography, to obtain 3.13 g of Intermediate C (Yield: 71%).

$^1$H NMR (CDCl$_3$, 400 MHz) ∂ (ppm) 7.24-7.04 (m, 14H), 6.75-6.58 (m, 4H), 5.12 (bs, 2H), 2.17 (s, 6H); $^{13}$C NMR (CDCl$_3$, 100 MHz) δ (ppm) 145.8, 133.2, 131.5, 129.7, 128.5, 127.8, 124.3, 123.8, 122.5, 119.5, 116.8, 17.6.

(2) Synthesis of Intermediate D 4.40 g (10.0 mmol) of Intermediate C was dissolved in 50 Ml of dichloromethane, and 4.0 Ml of triethylamine was added thereto. The mixture was cooled in an ice bath, and 4.21 g (30.0 mmol) of benzoyl chloride was dropped thereto. The resultant was stirred at 30° C., for 1 hour, and 50 Ml of water was added thereto. Then, the resultant was subject to extraction three times, using 50 Ml of ethyl ether. A collected organic layer was dried using magnesium sulfate, and the residue prepared by removing the solvent was recrystallized in DMF. The resultant was filtered while washing with acetone, to obtain 4.34 g of white solid Intermediate D (Yield: 67%).

1H NMR (CDCl3, 400 MHz) δ (ppm) 8.21-8.11 (d, 2H), 7.59-6.78 (m, 28H), 2.17 (s, 6H); $^{13}$C NMR (CDCl$_3$, 100 MHz) δ (ppm) 170.0, 141.3, 135.6, 135.1, 132.7, 131.3, 129.3, 129.1, 128.9, 128.8, 127.8, 125.5, 120.9, 119.8, 118.2, 18.0.

(3) Synthesis of Compound 12

A mixture prepared by sufficiently pulverizing and stirring 6.48 g (10 mmol) of Intermediate D, and 12.2 g (100 mmol) of potassium t-butoxide was added to an autoclave, and reacted at 340-350° C., at 5 MPa, for 2 hours. When the reaction was completed, the resultant tar was cooled to room temperature. The tar was pulverized, neutralized, filtered while washing distilled water, and dried. The residue was purified in a soxhlet device using acetone, for 2 days, to obtain 0.86 g of light yellow Compound 12 (Yield: 14%).

$^1$H NMR (CD$_2$Cl$_2$, 400 MHz) δ (ppm) 7.72-7.67 (m, 8H), 7.57-7.37 (m, 14H), 7.32-7.25 (m, 8H) 6.82 (s, 2H); $^{13}$C NMR (CD$_2$Cl$_2$, 100 MHz) δ (ppm) 141.2, 135.1, 134.9, 134.6, 133.1, 129.4, 128.4, 128.0, 127.4, 127.0, 126.3, 126.0, 125.1, 124.3, 121.2, 103.3, 101.8.

Synthesis Example 3

Synthesis of Compound 71

Compound 71 was synthesized through Reaction Scheme 4 below.

Reaction Scheme 4

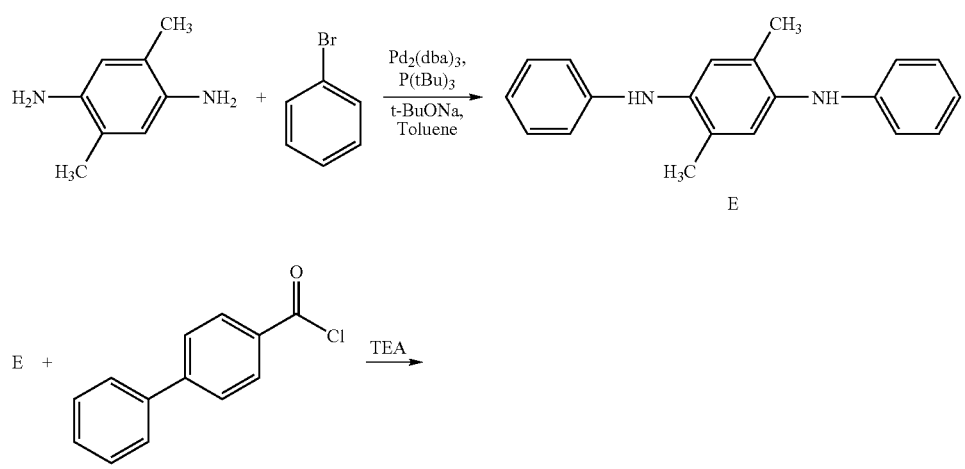

-continued

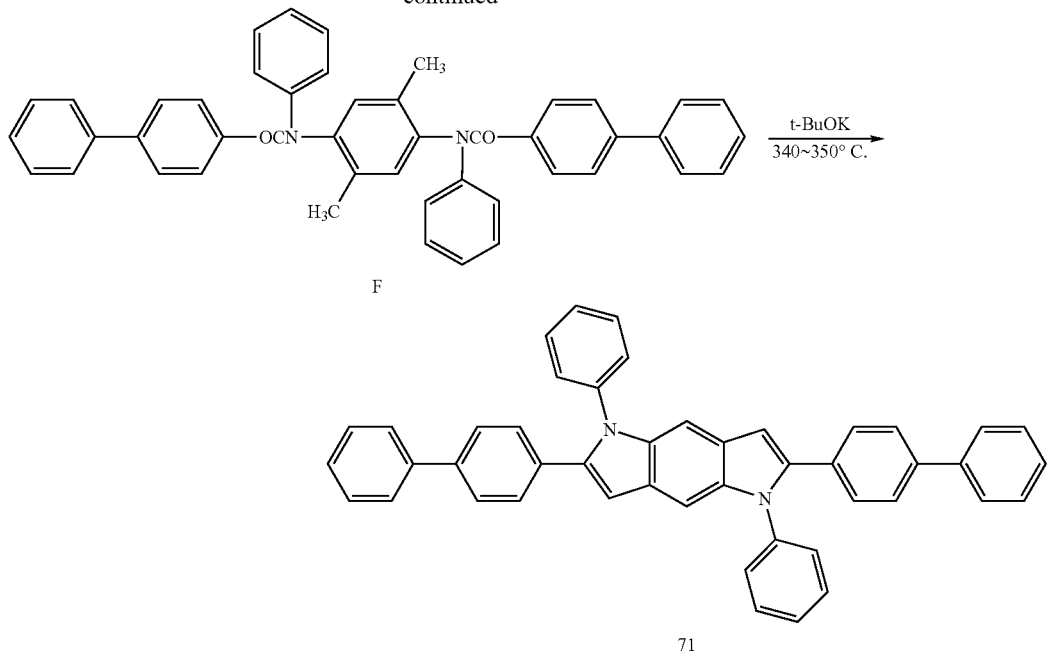

F

71

(1) Synthesis of Intermediate E 1.36 g (10.0 mmol) of 2,5-dimethyl-1,4-phenylenediamine and 3.77 g (24.0 mmol) of 4-bromobenzene were dissolved in 50 Ml of toluene. 2.88 g (30.0 mmol) of sodium t-butoxide, 0.388 g (0.40 mmol) of Pd(dba)$_2$, and 0.08 g (0.40 mmol) of tri-t-butylphosphine((t-Bu)$_3$P) were added to the solution, and the mixture was stirred at 80° C., for 5 hours. The resultant mixture was cooled to room temperature, and then 50 Ml of water was added thereto, and the resultant was subjected to extraction three times, using 20 Ml of ethyl ether. A collected organic layer was dried using magnesium sulfate, and the residue prepared by removing the solvent was separated and purified, using a silica gel column chromatography, to obtain 1.78 g of Intermediate E (Yield: 62%).

$^1$H NMR (CDCl$_3$, 400 MHz) δ (ppm) 7.28-6.89 (m, 12H), 5.43 (s, 2H), 2.15 (s, 3H); $^{13}$C NMR (CDCl$_3$, 100 MHz) δ (ppm) 147.5, 139.2, 134.9, 129.3, 121.0, 117.5, 18.2.

(2) Synthesis of Intermediate F 4.40 g (10.0 mmol) of Intermediate E was dissolved in 50 Ml of dichloromethane, and 4.0 Ml of triethylamine was added thereto. The mixture was cooled in an ice bath, and 6.50 g (30.0 mmol) 4-biphenylcarbonyl chloride was dropped thereto. The resultant was stirred at 30° C., for 1 hour, and 50 Ml of water was added thereto. Then, the resultant was subject to extraction three times, using 50 Ml of ethyl ether. A collected organic layer was dried using magnesium sulfate, and the residue prepared by removing the solvent was recrystallized in DMF. The resultant was filtered while washing with acetone, to obtain 4.21 g of light yellow solid Intermediate F (Yield: 65%).

$^1$H NMR (CDCl$_3$, 400 MHz) δ (ppm) 7.44-6.89 (m, 30H), 2.14 (s, 6H); $^{13}$C NMR (CDCl$_3$, 100 MHz) δ (ppm) 160.9, 143.2, 142.3, 141.2, 136.7, 135.8, 134.9, 134.2, 130.3, 129.4, 128.9, 127.8, 126.8, 126.4, 125.8, 124.5, 17.8.

(3) Synthesis of Compound 71

A mixture prepared by sufficiently pulverizing and stirring 6.48 g (10 mmol) of Intermediate F and 12.2 g (100 mmol) of potassium t-butoxide was added to an autoclave, and reacted at 340-350° C., at 5 MPa, for 2 hours. When the reaction was completed, the resultant tar was cooled to room temperature. The tar was pulverized, neutralized, filtered while washing with distilled water, and dried. The residue was purified in a soxhlet device using acetone, for 2 days, to obtain 1.12 g of light yellow Compound 12 (Yield: 18%).

$^1$H NMR (CD$_2$Cl$_2$, 400 MHz) δ (ppm) 7.98-7.65 (m, 8H), 7.48-7.32 (m, 14H), 7.22-7.12 (m, 8H) 6.80 (s, 2H); $^{13}$C NMR (CD$_2$Cl$_2$, 100 MHz) δ (ppm) 145.2, 136.1, 134.5, 134.1, 133.2, 128.4, 127.4, 126.0, 125.8, 125.0, 123.2, 122.3, 121.1, 121.0, 119.2, 102.3, 101.9.

Example 1

Preparation of Organic Light Emitting Device

A Corning 15 Ω/cm$^2$ (1200 Å) ITO glass substrate was cut into pieces measuring 50 mm×50 mm×0.7 mm in size, then the pieces were cleaned by sonification in isopropyl alcohol and deionized water, for 5 minutes. Then the pieces were UV/ozone cleaned for 30 minutes. The glass substrate was installed in a vacuum deposition device.

4,4',4''-tris[2-naphthyl(phenyl)aminotriphenylamine (2-TNATA), represented by the formula, below was vacuum deposited to a thickness of 600 Å on the substrate, to form a HIL. Then, 4,4'-bis[N-(1-naphthyl)-N-phenylaminobiphenyl (NPB), represented by the formula below, as a hole transporting compound was vacuum deposited to a thickness of 300° C., on the HIL, to form a HTL.

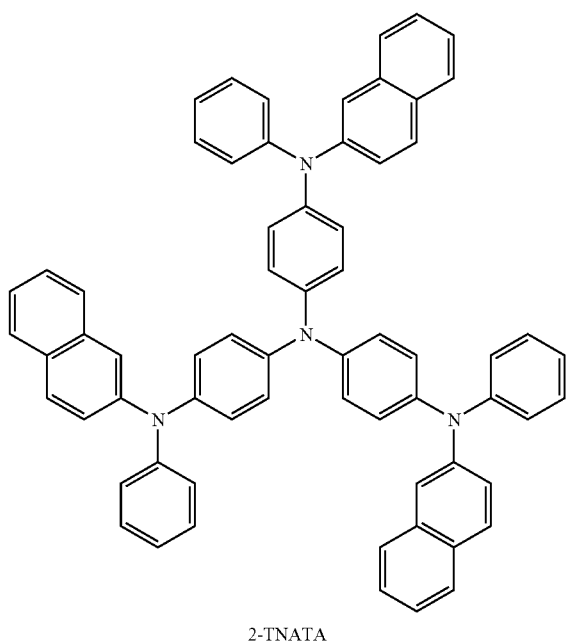

2-TNATA

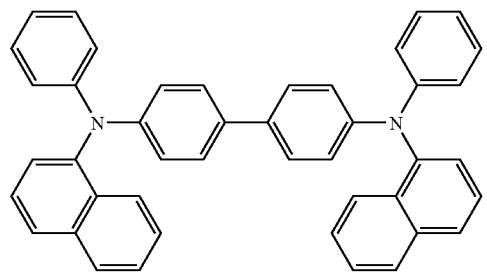

NPB

CBP represented by the formula below (as a known blue phosphorescent host) and Compound 2 were deposited at the same time, in a weight ratio of 98:2, on the HTL, to form an EML having a thickness of 300 Å.

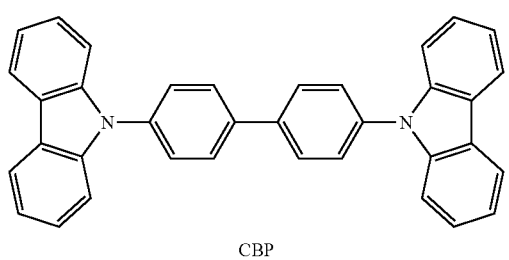

CBP

Then, Alq$_3$ was deposited on the EML to a thickness of 300 Å, to form an ETL. LiF as a halogenated alkali metal was deposited on the ETL to a thickness of 10 Å, to form an EIL, and Al was vacuum deposited to a thickness of 3000 Å, to form a LiF/Al electrode (cathode), to prepare an organic light emitting device.

Figure 2:
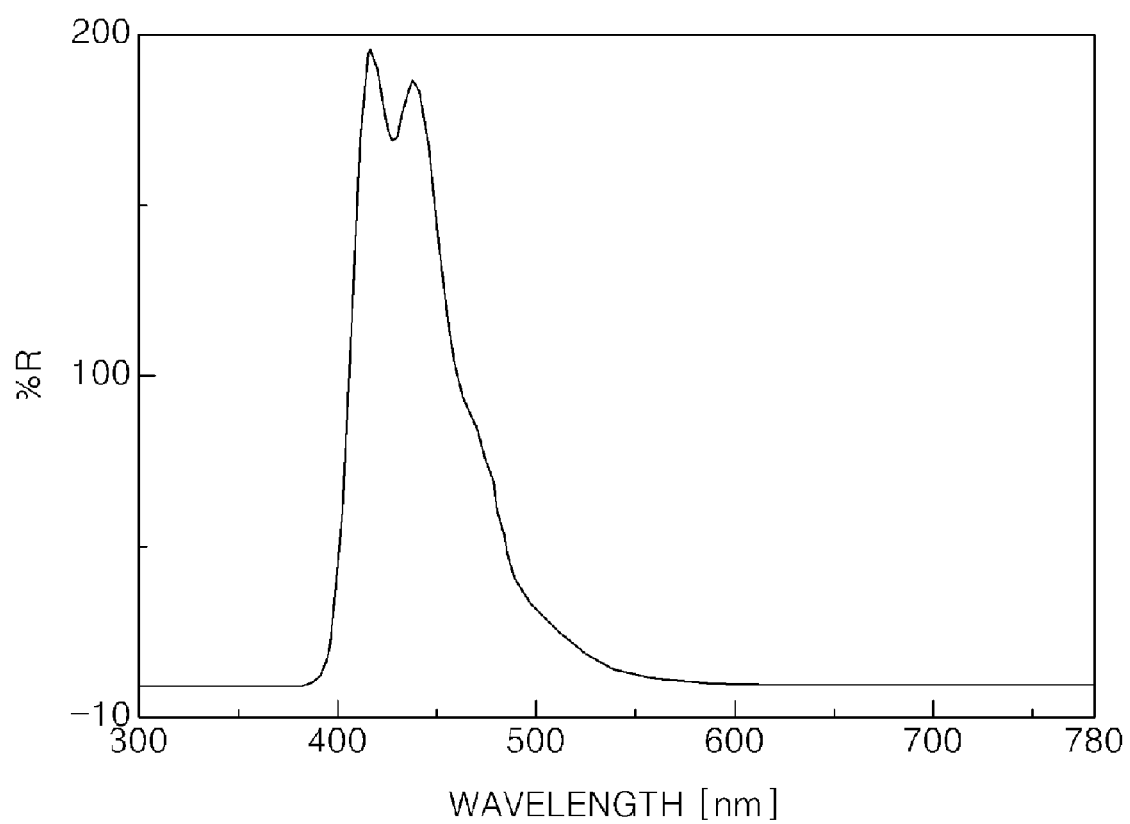
FIG. 2 is a graph illustrating an emission spectrum of an organic light emitting device, according to an exemplary embodiment of the present invention.

An emission spectrum of the prepared organic light emitting device was shown in FIG. 2. Referring to FIG. 2, the heterocyclic compound emits a blue color showing a main peak in the range of 400 to 450 nm in an emission spectrum.

At a current density of 100 mA/cm$^2$, the organic light emitting device emitted a blue color with a high color purity, and the driving voltage of the organic light emitting device was 8.4 V, the brightness was 1,452 cd/m$^2$, the color coordinates were (0.149, 0.102), and the light emitting efficiency was 1.45 cd/A.

Example 2

Preparation of Organic Light Emitting Device

An organic light emitting device was manufactured in the same manner as in Example 1, except that a compound represented by the formula below, was used instead of CBP as a host in the formation of the EML.

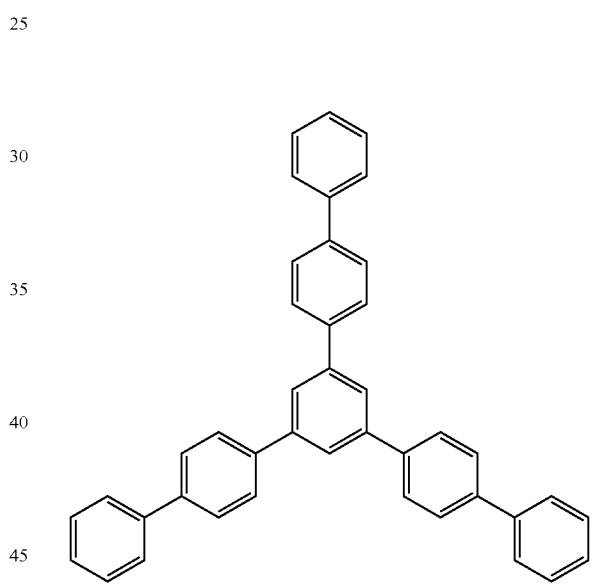

At a current density of 100 mA/cm$^2$, the organic light emitting device emitted a blue color with high color purity, and the driving voltage of the organic light emitting device was 8.33 V, the brightness was 1,763 cd/m$^2$, the color coordinates were (0.147, 0.084), and the light emitting efficiency was 1.76 cd/A.

Example 3

Preparation of Organic Light Emitting Device

An organic light emitting device was manufactured in the same manner as in Example 1 except that a compound represented by the formula below was used instead of CBP as a host in the formation of the EML.

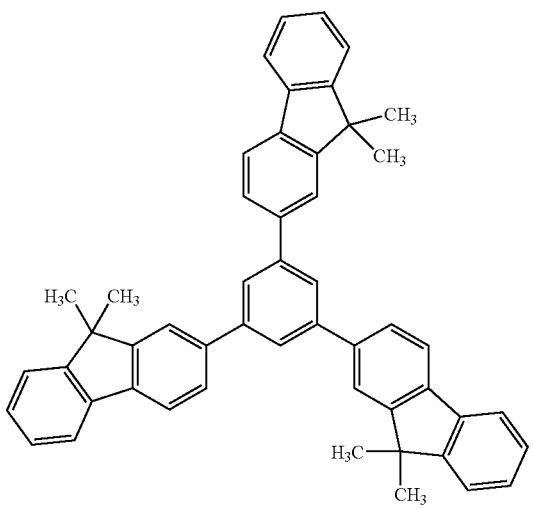

At a current density of 100 mA/cm², the organic light emitting device emitted a blue color with high color purity, and the driving voltage of the organic light emitting device was 8.25 V, the brightness was 1,526 cd/m², the color coordinates were (0.147, 0.071), and the light emitting efficiency was 1.53 cd/A.

Example 4

Preparation of Organic Light Emitting Device

An organic light emitting device was manufactured in the same manner as in Example 1, except that a compound represented by the formula below and Compound 12 were deposited at the same time, in a weight ratio of 98:2, to a thickness of 300 Å, for the formation of the EML.

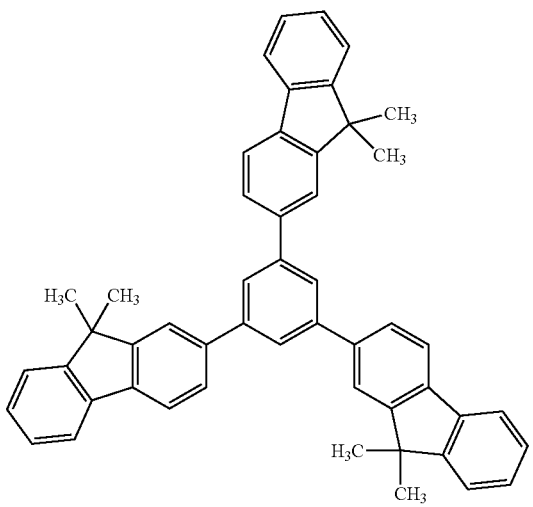

At a current density of 100 mA/cm², the organic light emitting device emitted a blue color with high color purity, and the driving voltage of the organic light emitting device was 8.12 V, the brightness was 1,847 cd/m², the color coordinates were (0.147, 0.071), and the light emitting efficiency was 1.85 cd/A.

The results of the organic light emitting devices according to Examples 1 to 4 were shown in Table 1.

TABLE 1

| Example | Driving voltage (V) | Current density (mA/cm²) | Brightness (cd/m²) | Light emitting efficiency (cd/A) | Color coordinates (x, y) |
|---|---|---|---|---|---|
| Example 1 | 8.40 | 100 | 1,452 | 1.45 | (0.149, 0.102) |
| Example 2 | 8.33 | 100 | 1,763 | 1.76 | (0.147, 0.084) |
| Example 3 | 8.25 | 100 | 1,526 | 1.53 | (0.147, 0.071) |
| Example 4 | 8.12 | 100 | 1,847 | 1.85 | (0.147, 0.071) |

As shown in Table 1, the CIE color coordinates, of the organic light emitting device prepared according to Example 1, were (0.14, 0.07), which are nearly identical to the color coordinates of the blue color specified by the NCST. Therefore, the organic light emitting device according to aspects of the present invention, has excellent color reproduction range.

As described above, as a result of using the compound represented by Formula 1 to form an emission layer, an organic light emitting device emitting a blue color with a high color purity, can be prepared. Since the heterocyclic compound emits a blue color with high electrical stability and a high color purity, an organic light emitting device having an excellent color gamut, particularly a large-scale bottom emission type organic light emitting device, can be prepared.

Although a few exemplary embodiments of the present invention have been shown and described, it would be appreciated by those skilled in the art that changes may be made in these exemplary embodiments, without departing from the principles and spirit of the invention, the scope of which is defined in the claims and their equivalents.

What is claimed is:
1. A heterocyclic compound represented by Formula 1:

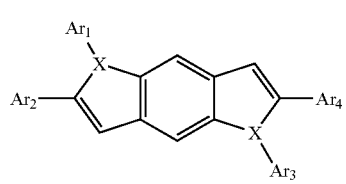

Formula 1 wherein X is selected from the group consisting of nitrogen, boron, and phosphorous; and
the $Ar_1$, $Ar_2$, $Ar_3$, and $Ar_4$ are each independently selected from the group consisting of a C6-C30 substituted or unsubstituted aryl group, a C6-C30 substituted or unsubstituted aryloxy group, a C4-C20 substituted or unsubstituted heterocyclic group, and a C6-C20 fused polycyclic group.

2. The heterocyclic compound of claim 1, wherein:
the $Ar_1$, $Ar_2$, $Ar_3$, and $Ar_4$ are each independently selected from the group consisting of a phenyl group, a naphthyl group, a biphenyl group, a terphenyl group, a fluorenyl group, a carbazolyl group, a pyridyl group, a quinolyl group, and derivatives thereof, in which at least one of the hydrogen atoms is substituted with a C1-C5 short-chain alkyl group, a C1-C5 short-chain alkoxy group, a cyano group, an amine group, a phenoxy group, a phenyl group, or a halogen group.

3. The heterocyclic compound of claim 1, wherein the $Ar_1$ and $Ar_3$ are identical, and the $Ar_2$ and $Ar_4$ are identical.

4. The heterocyclic compound of claim 1, wherein X is nitrogen.
5. The heterocyclic compound of claim 1, wherein the compound represented by Formula 1 is selected from the group consisting of the compounds represented by the formulae below:
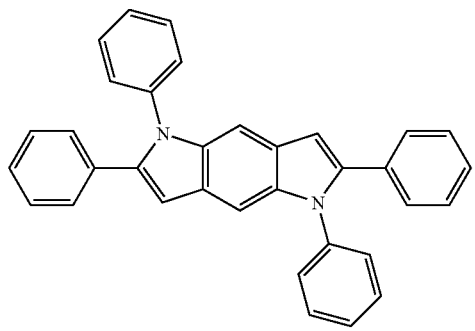
1
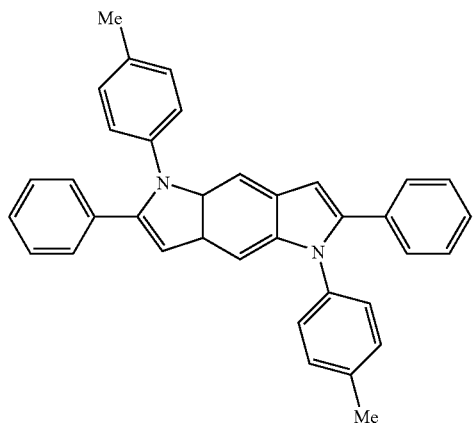
2
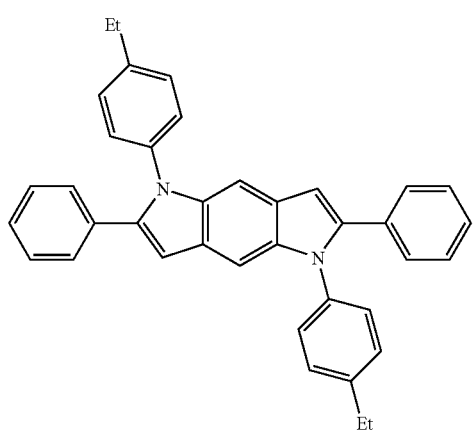
3
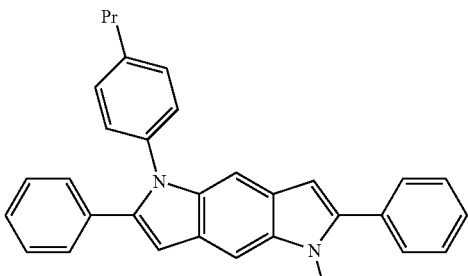
4
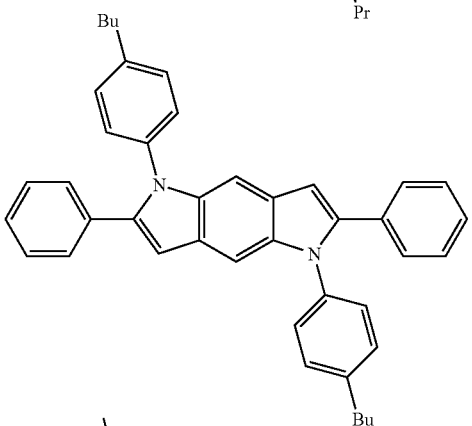
5
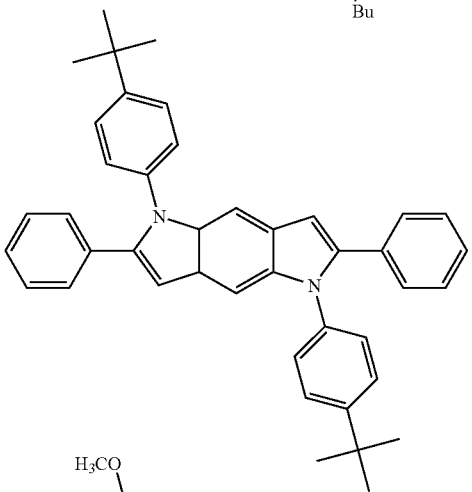
6
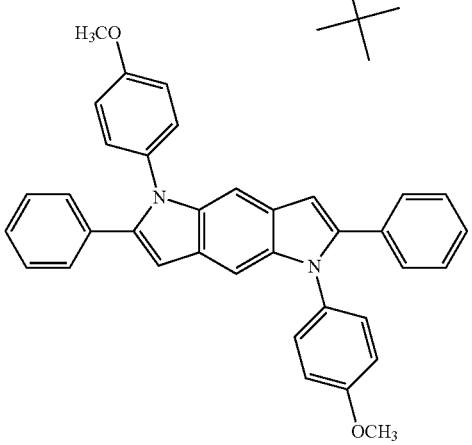
7

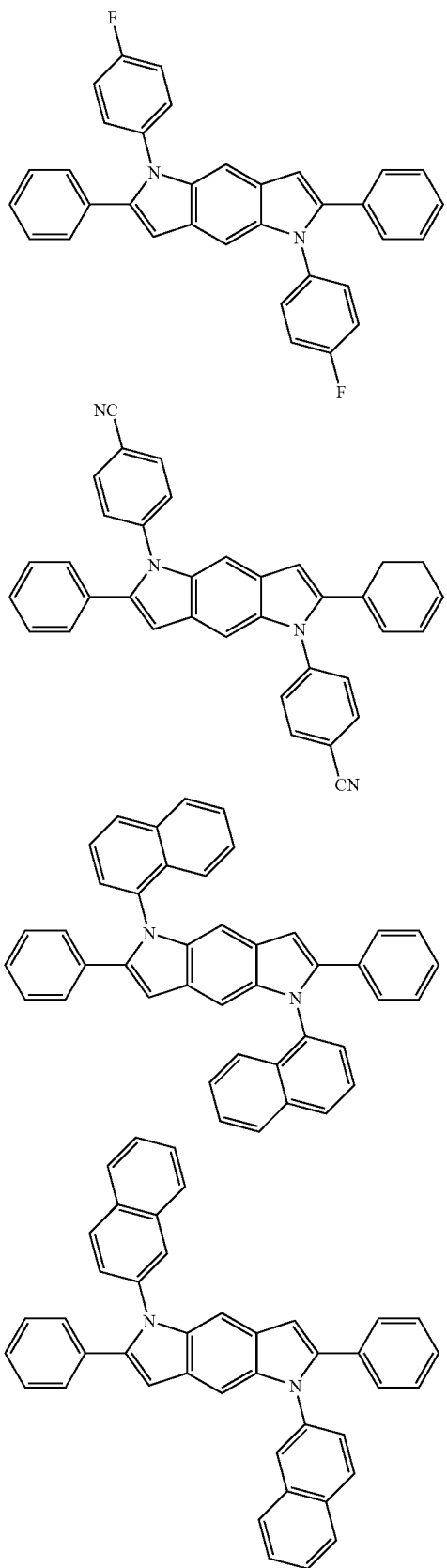
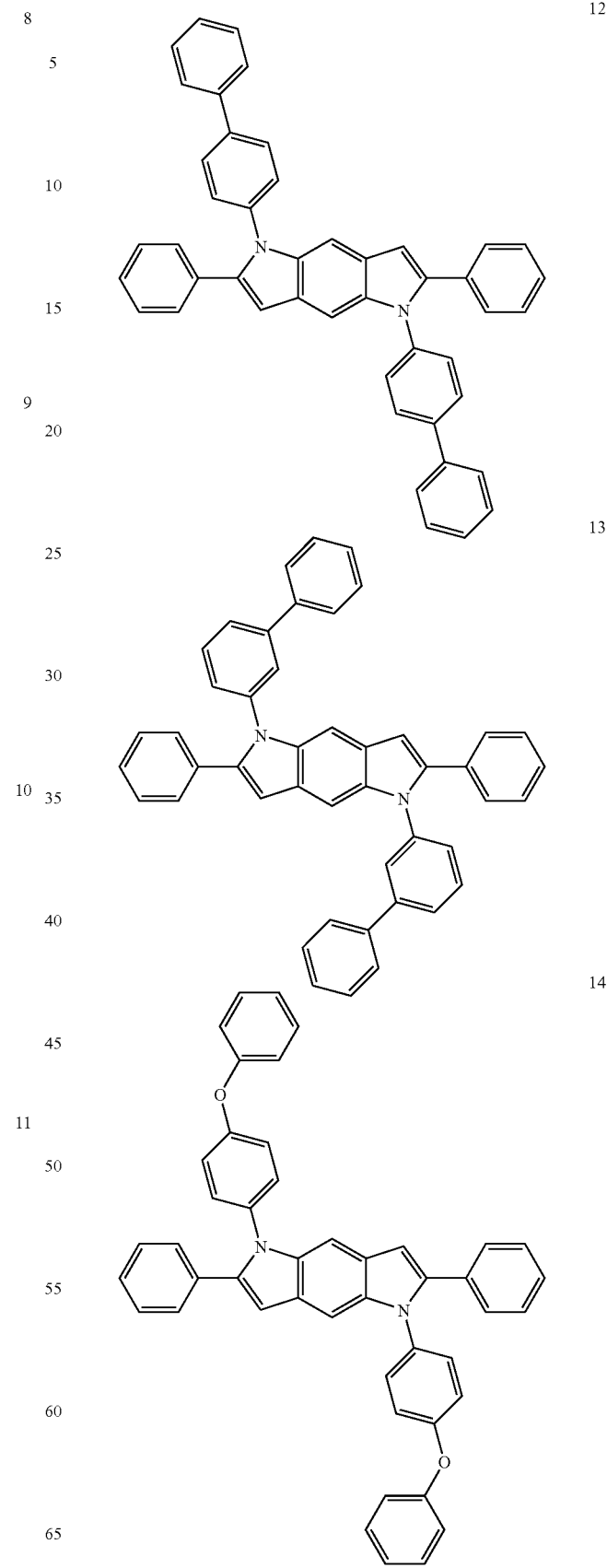

-continued
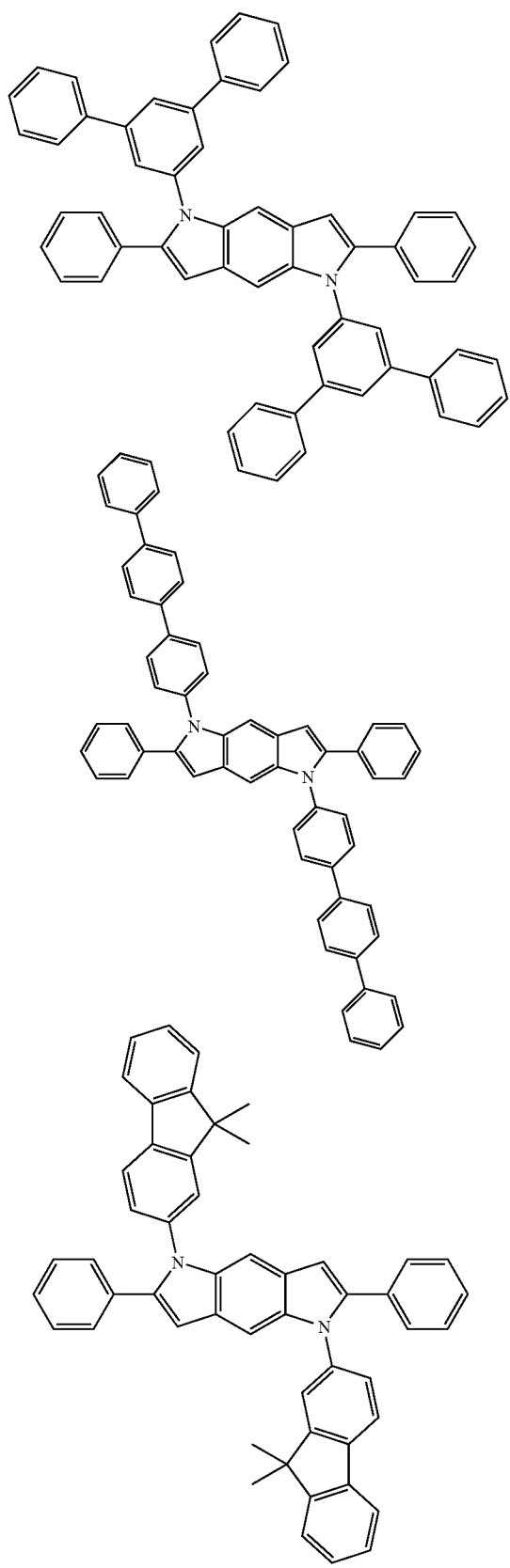
-continued
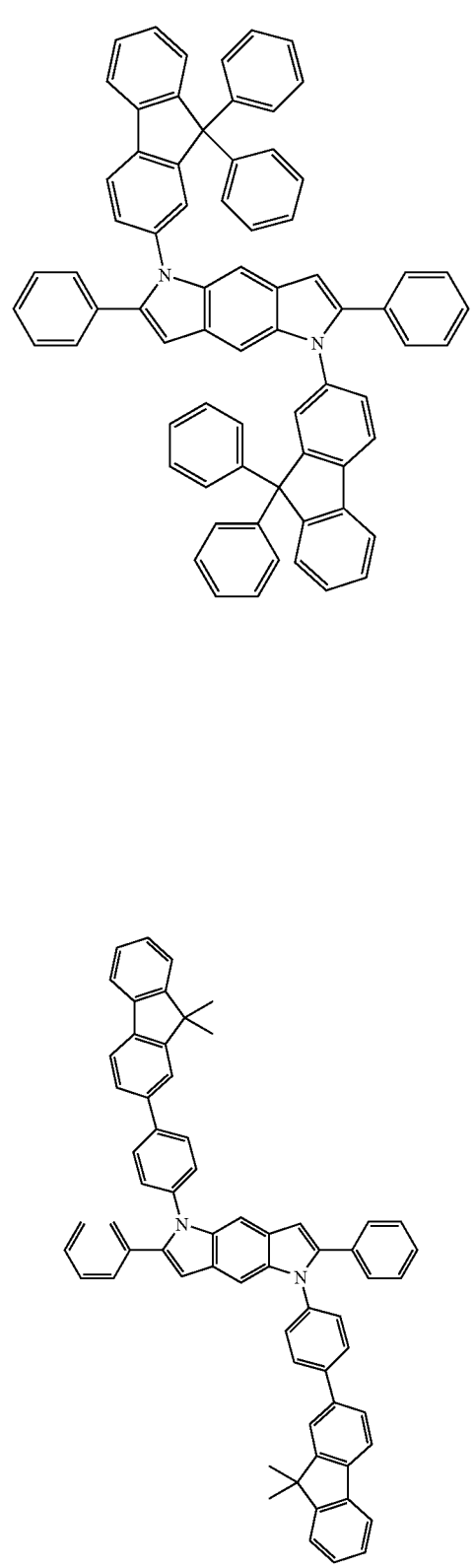

5
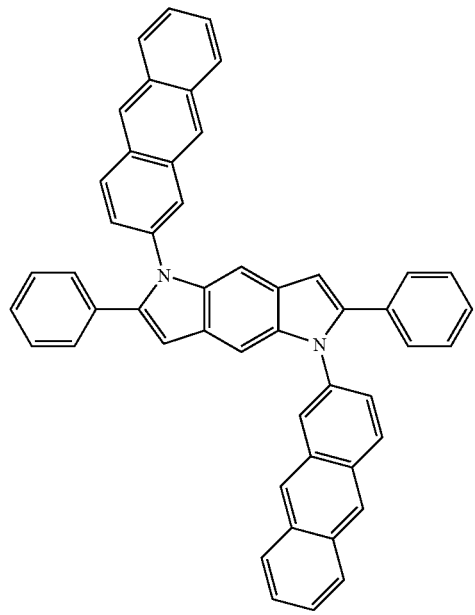
20
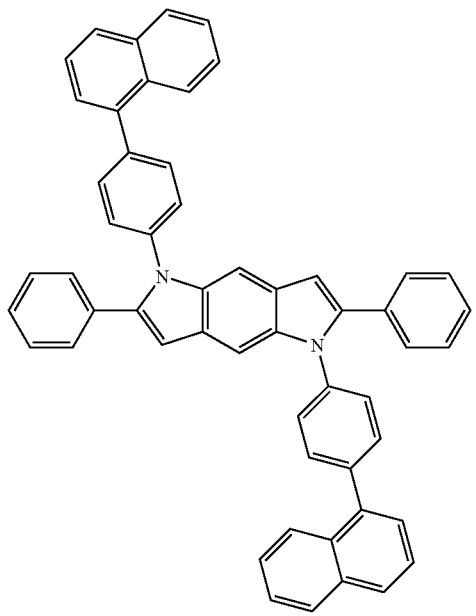
21
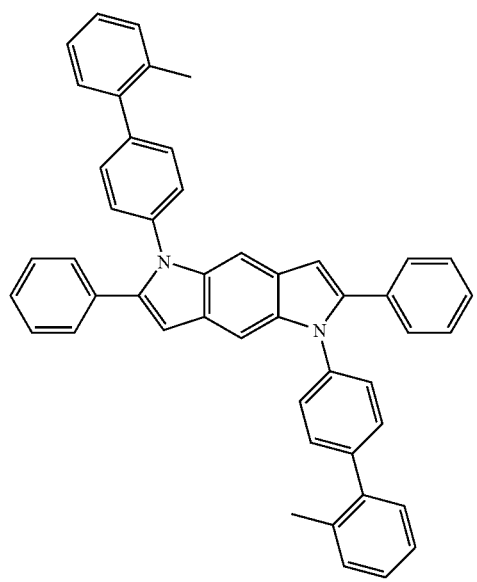
23
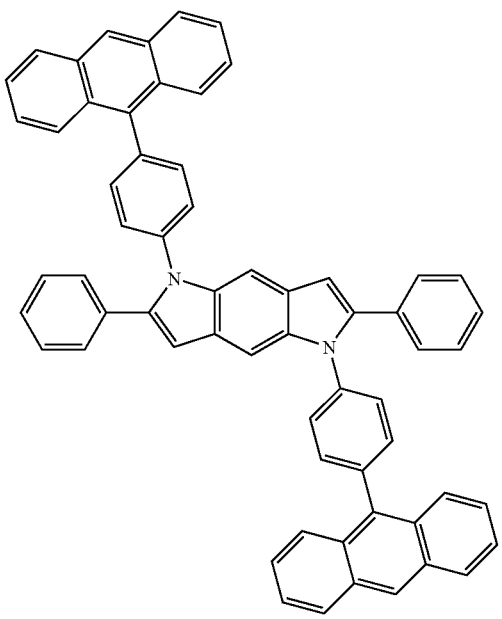

24
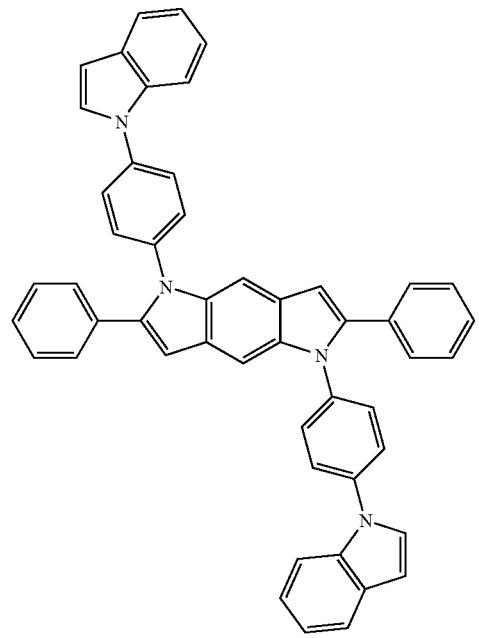
25
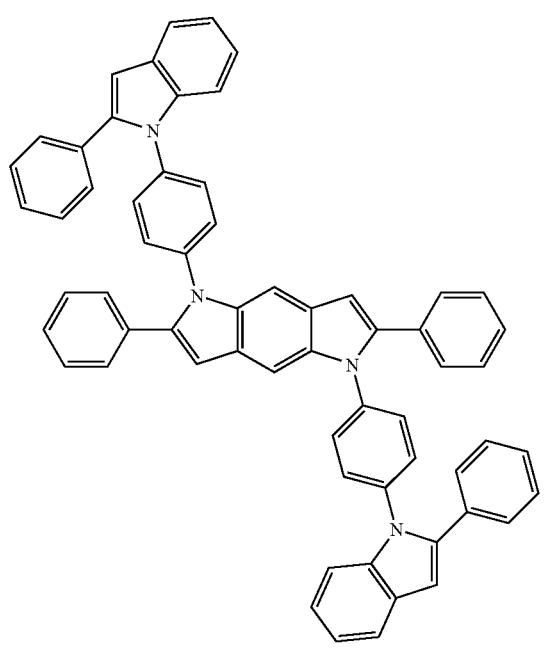
26
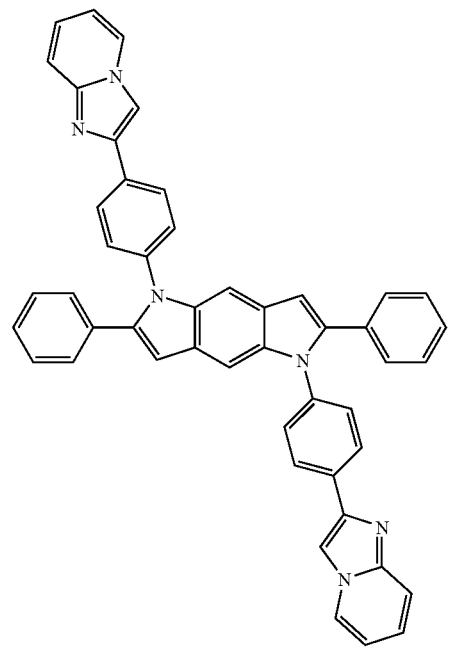
27
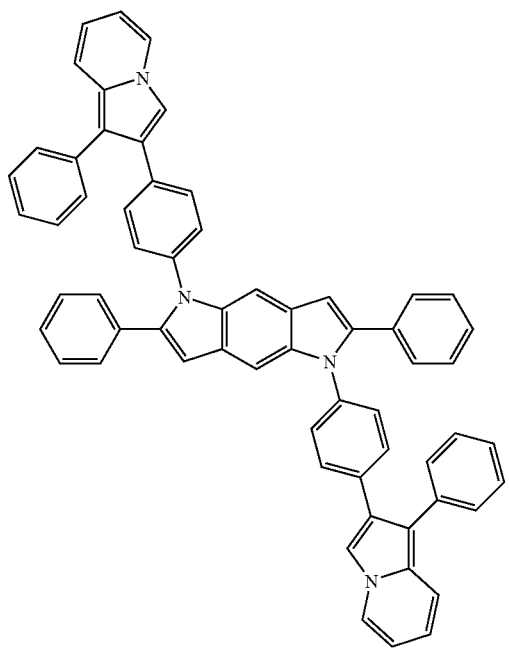

28
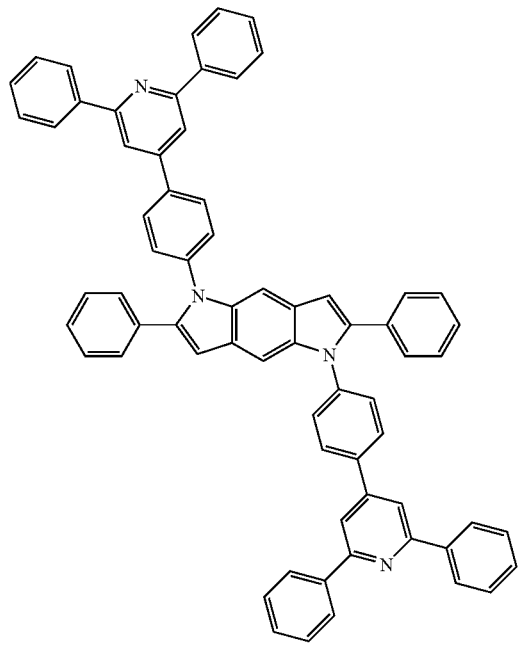
29
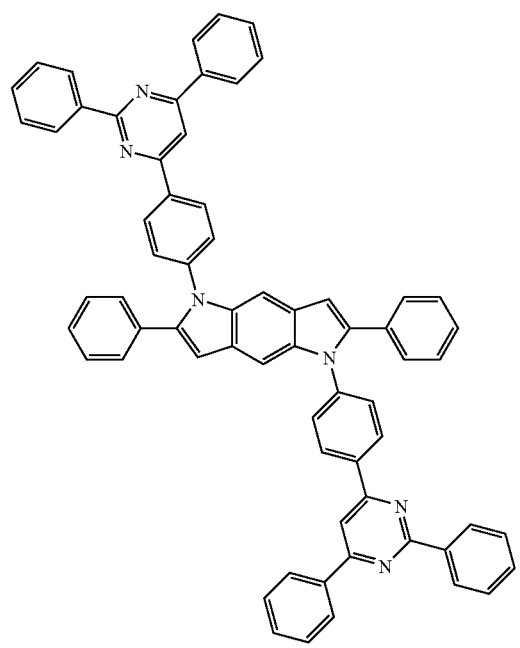
30
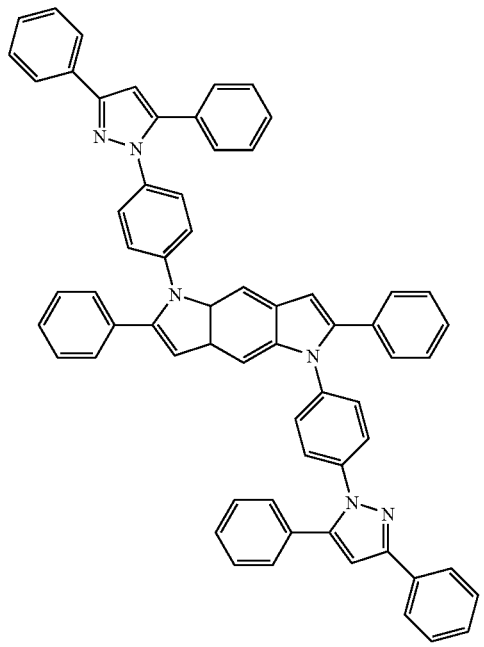
31
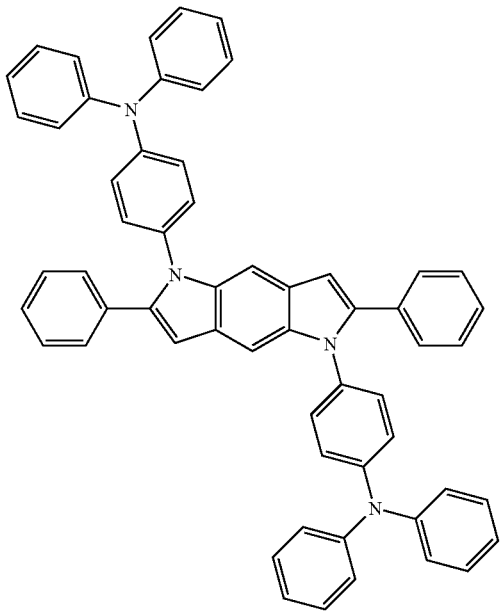

32
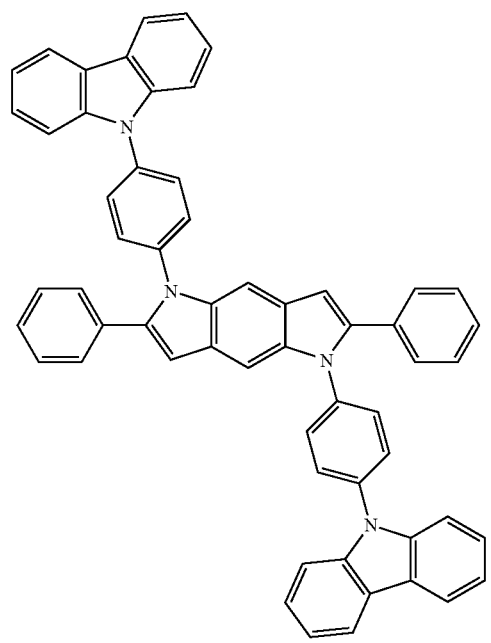
33
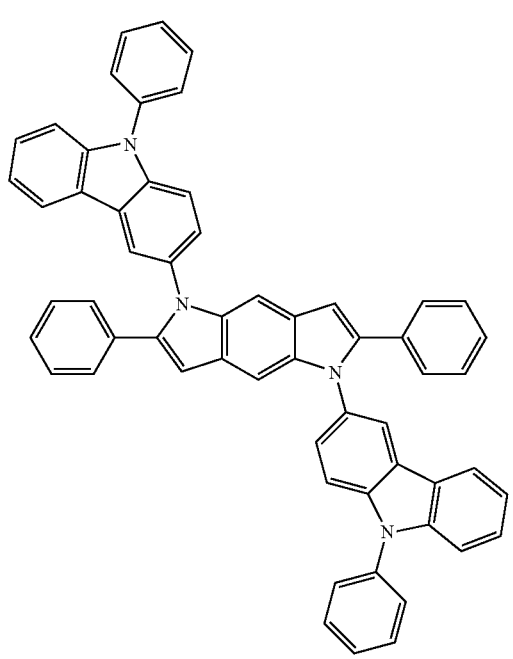
34
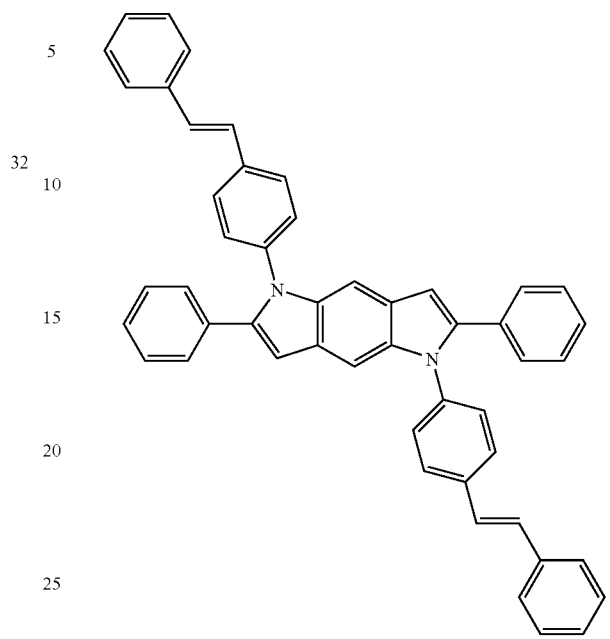
35
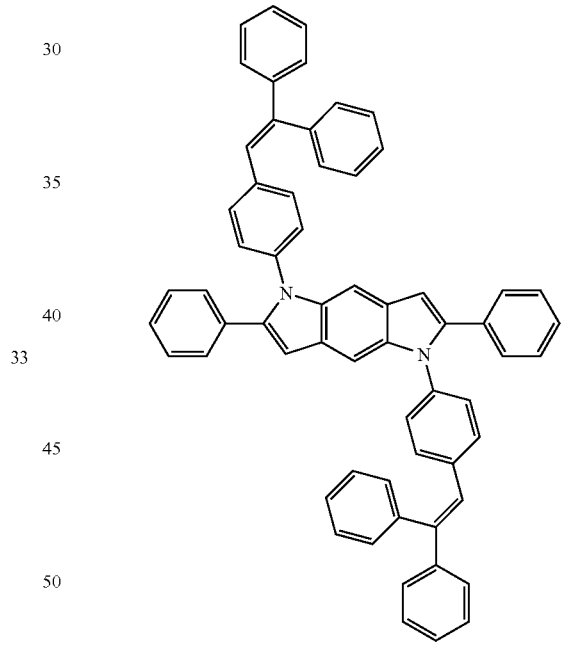
36
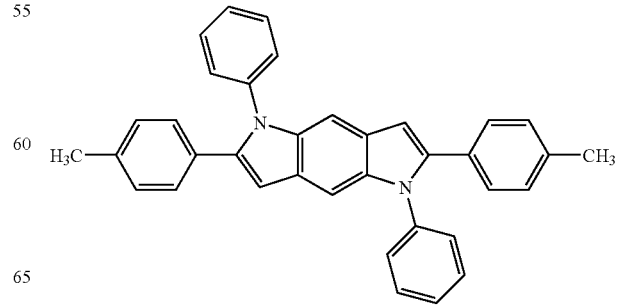

-continued
37
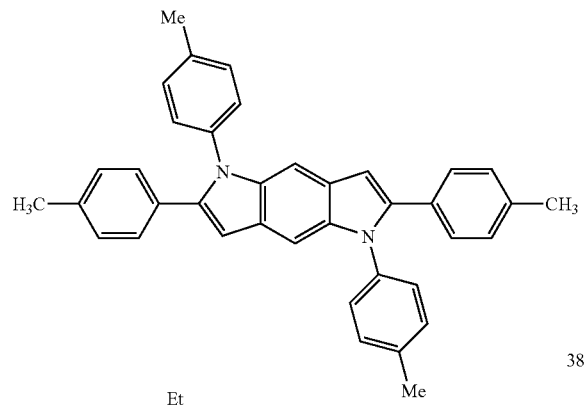
38
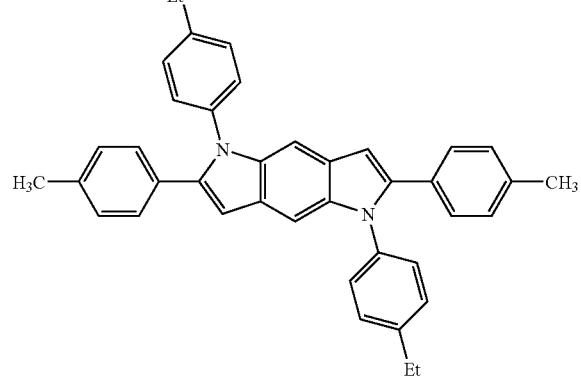
39
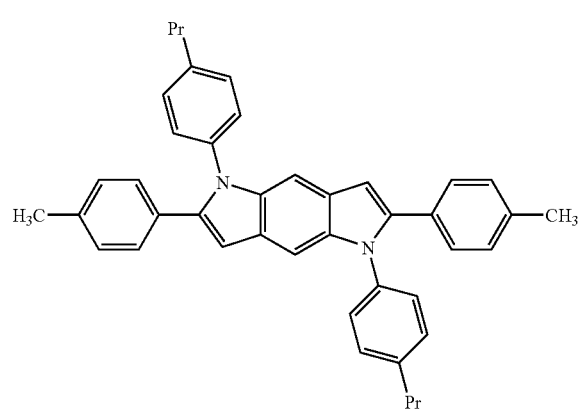
40
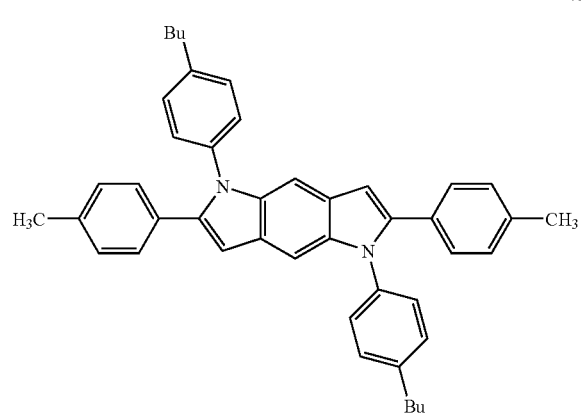
-continued
41
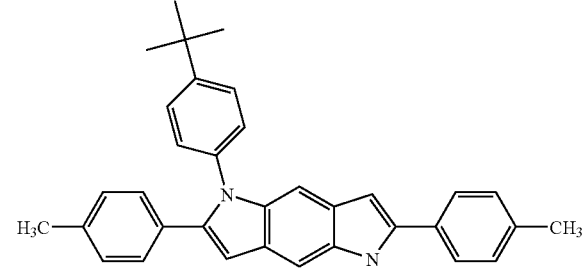
42
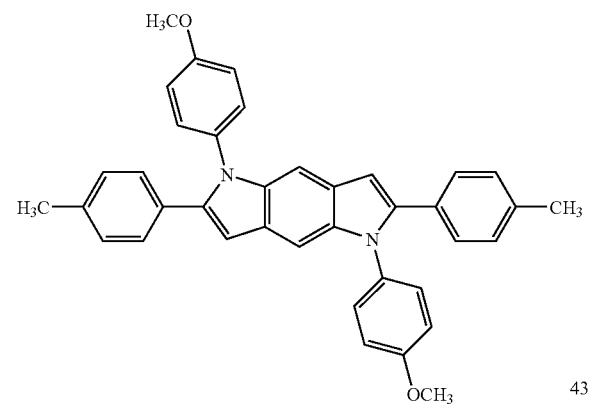
43
44
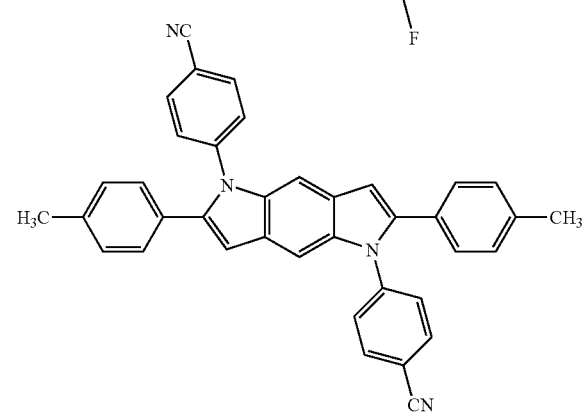

-continued
45
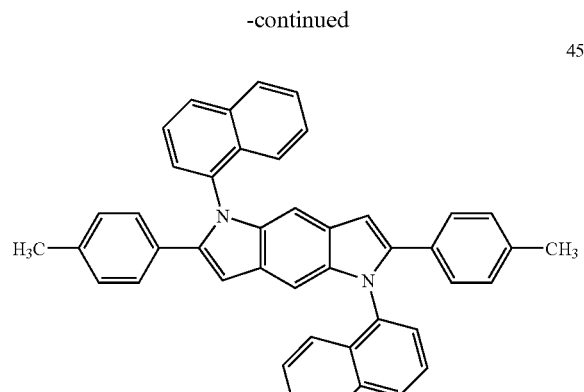
46
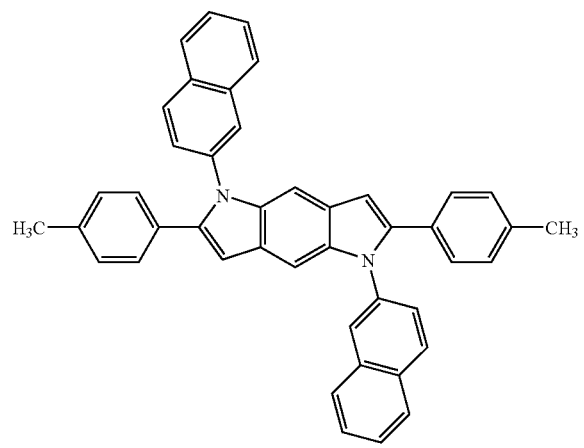
47
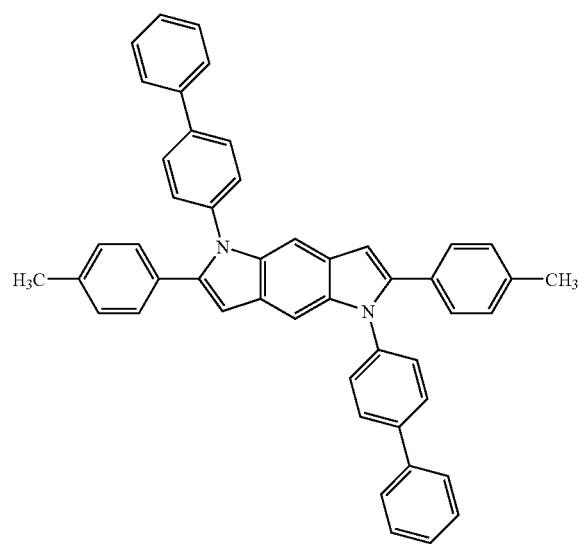
-continued
48
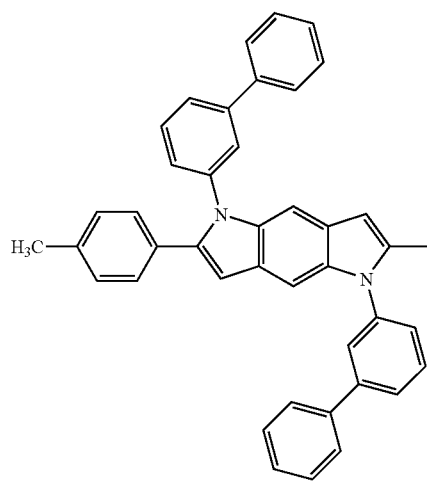
49
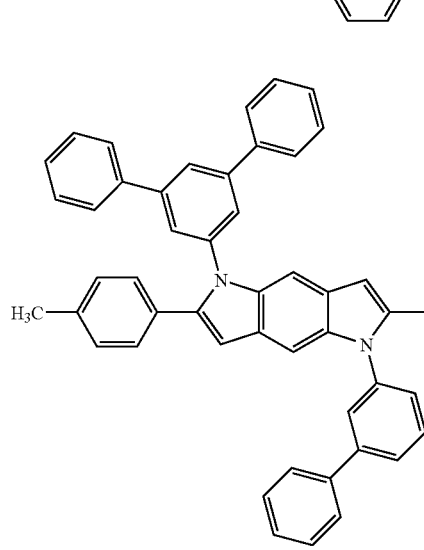
50

-continued
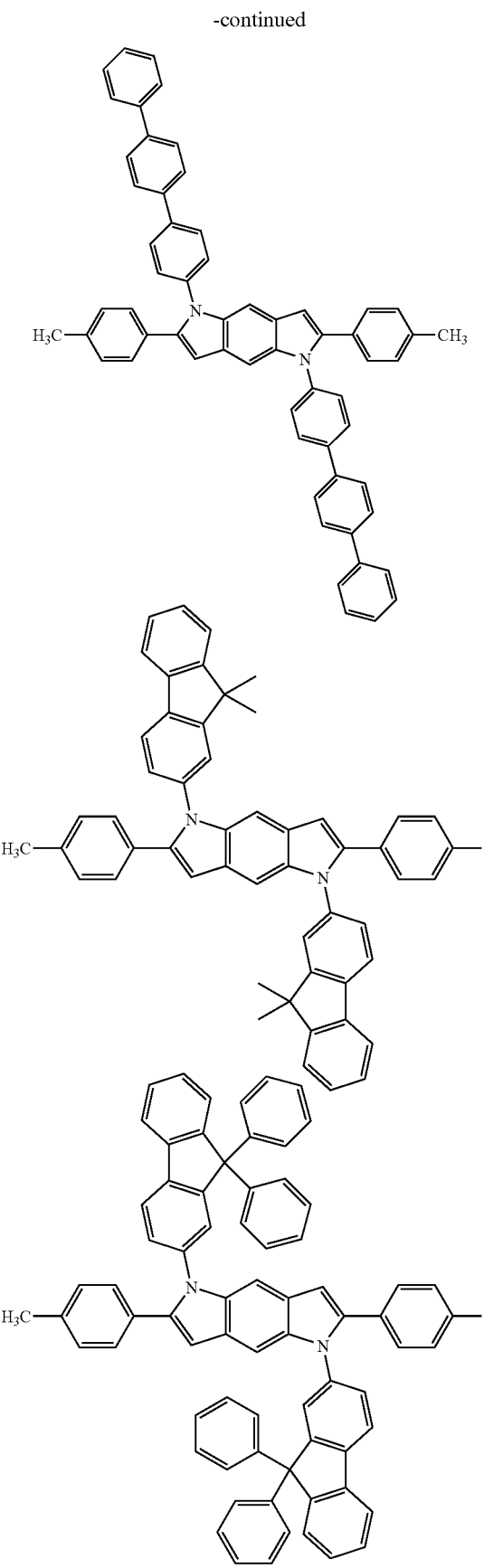
-continued
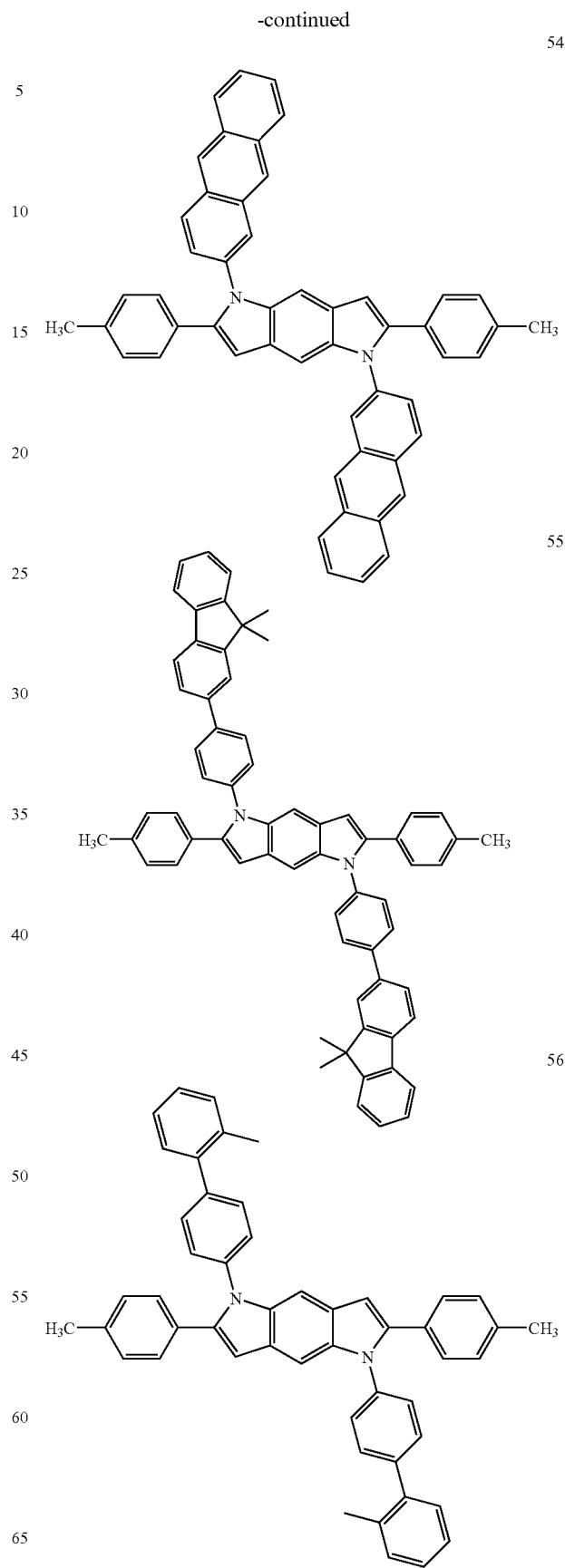

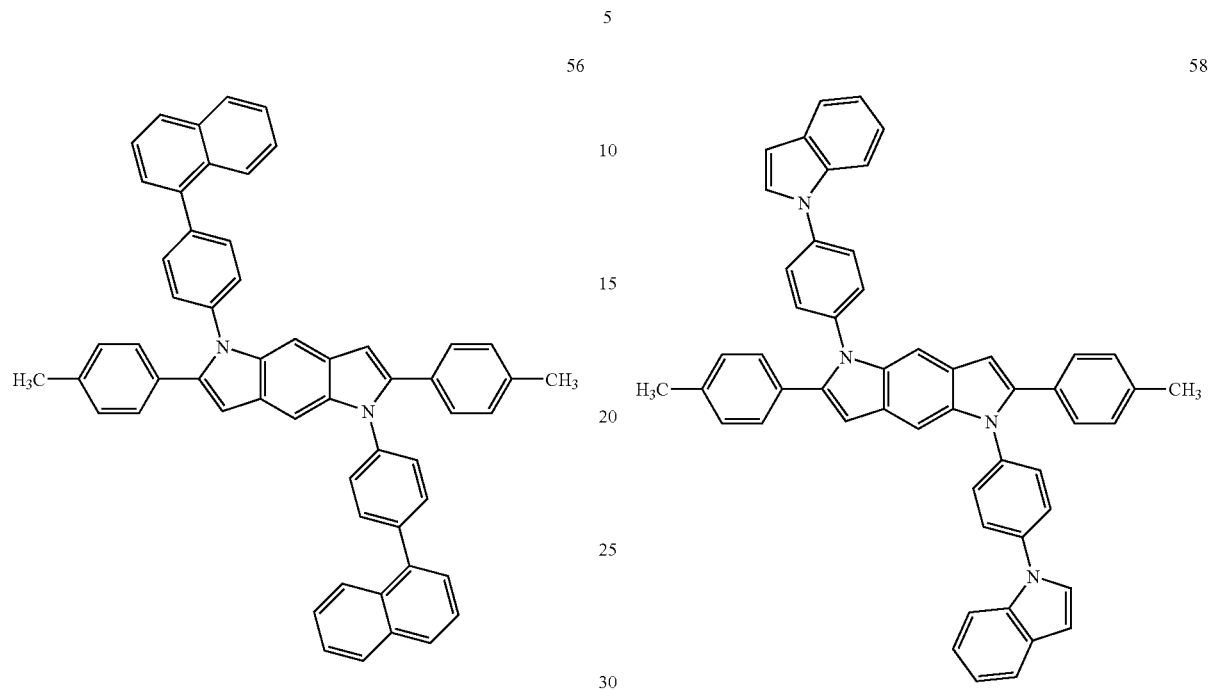
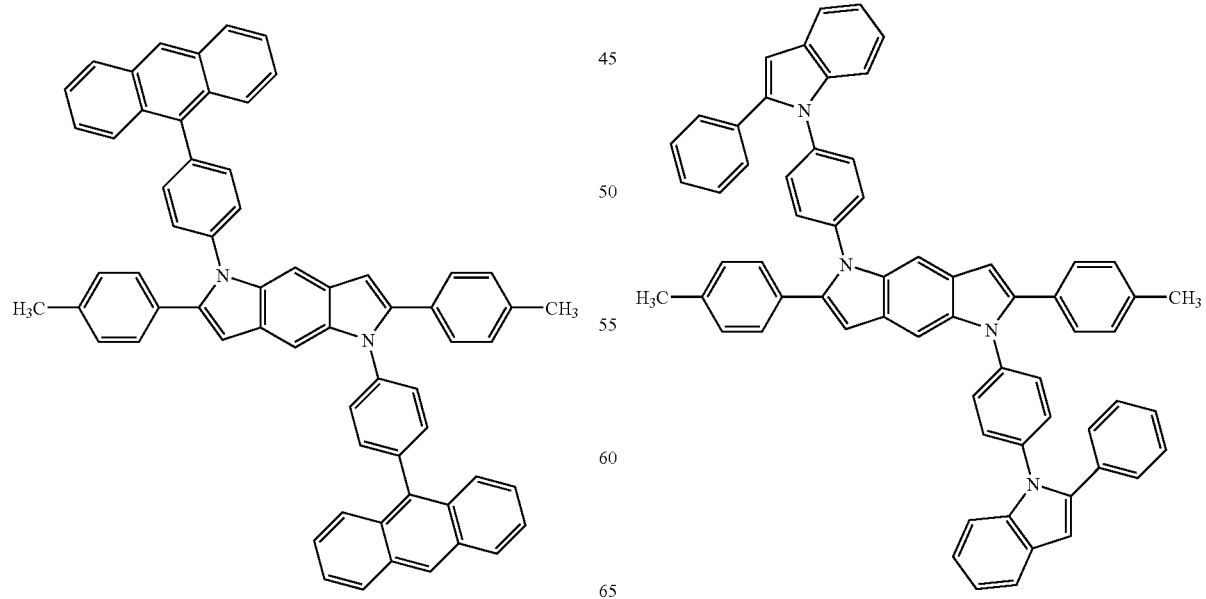

-continued
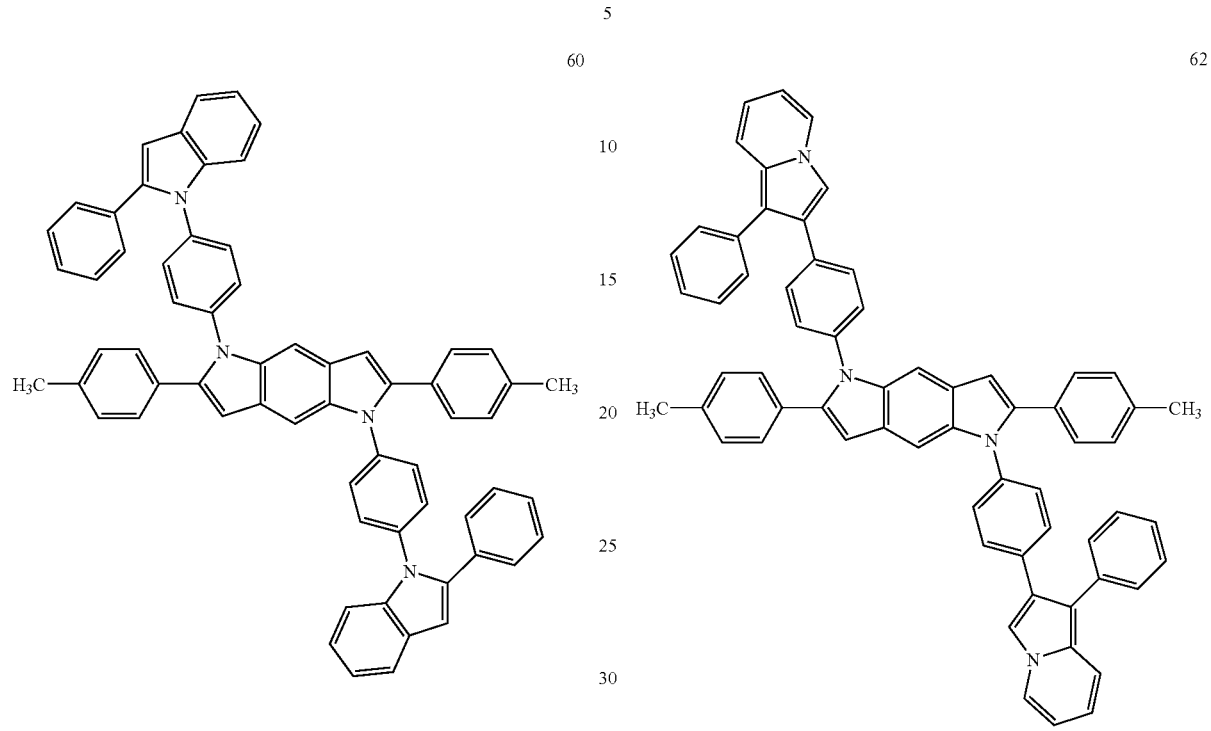
-continued
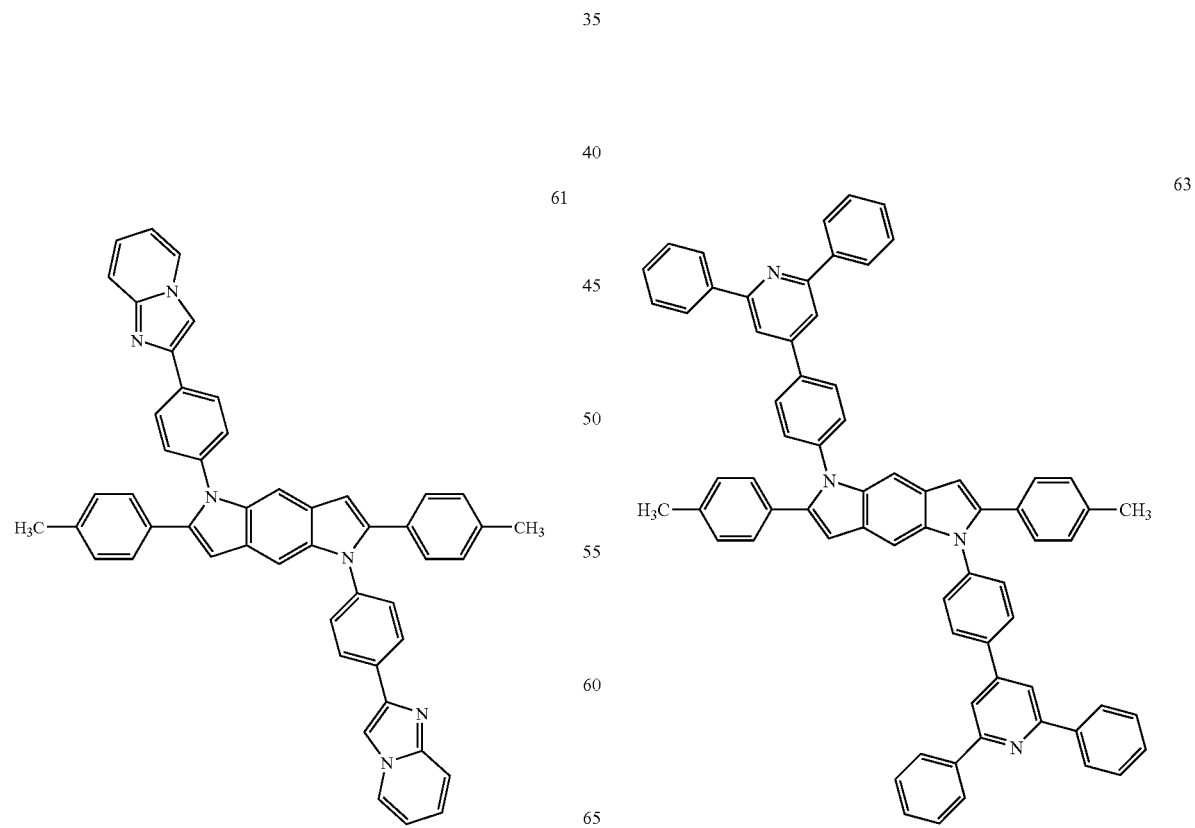

64
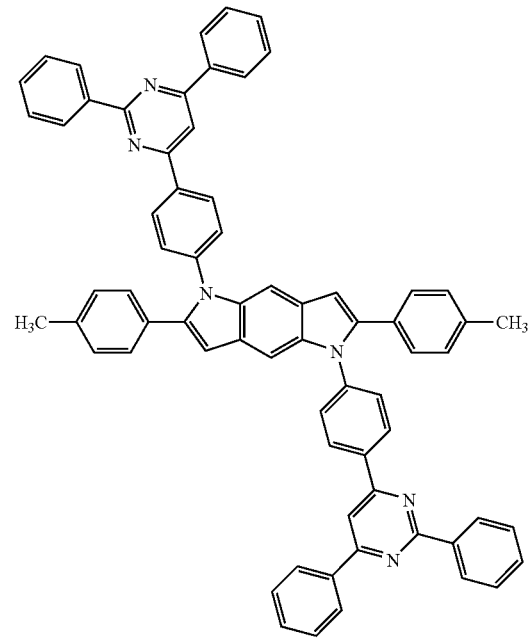
66
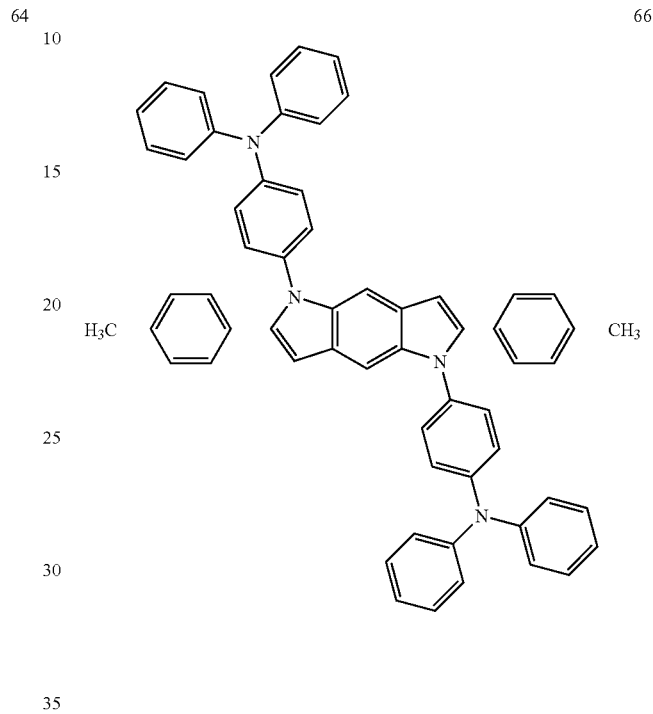
65
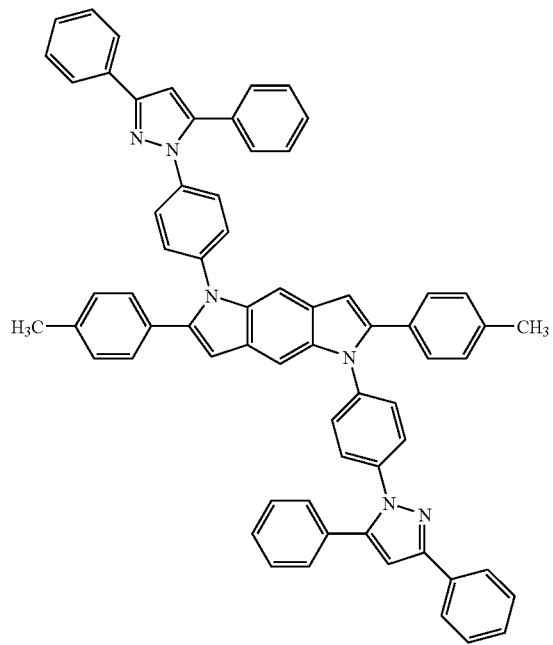
67
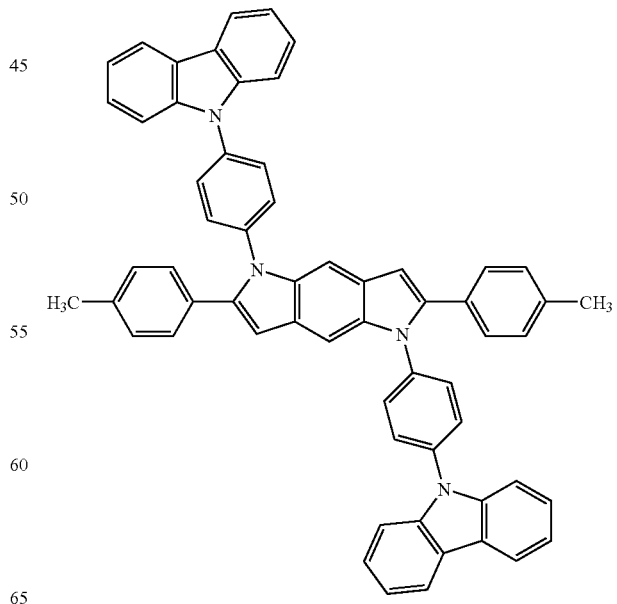

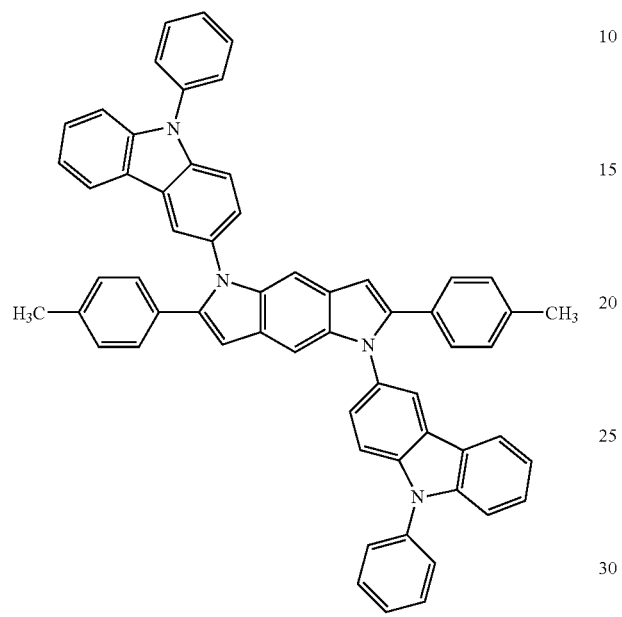
68
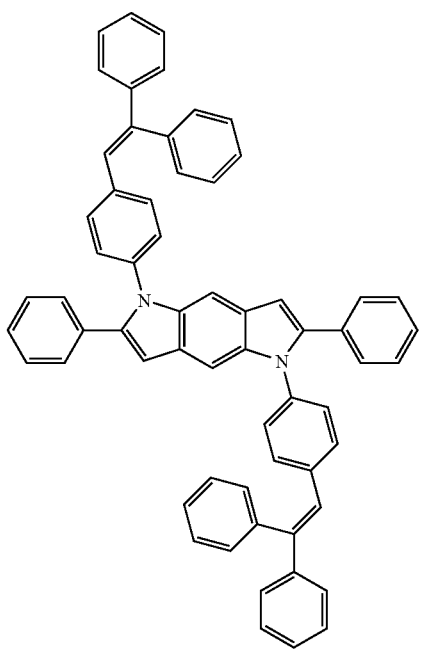
70
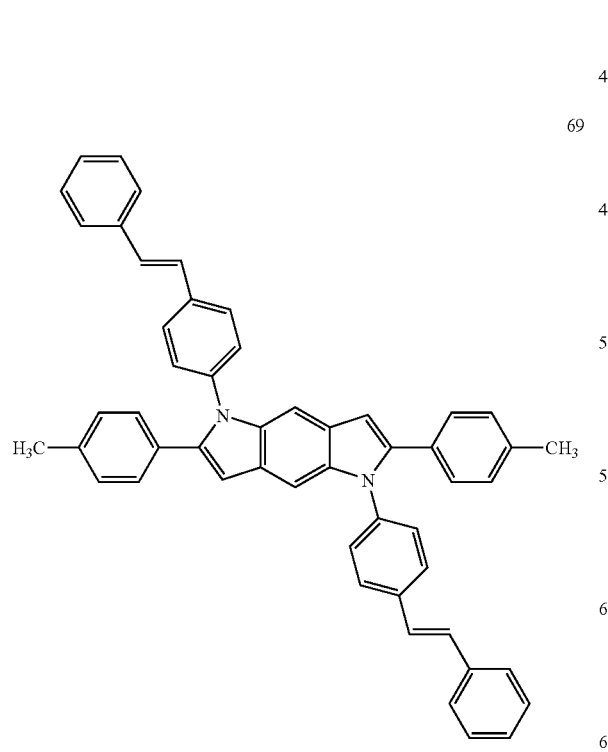
69
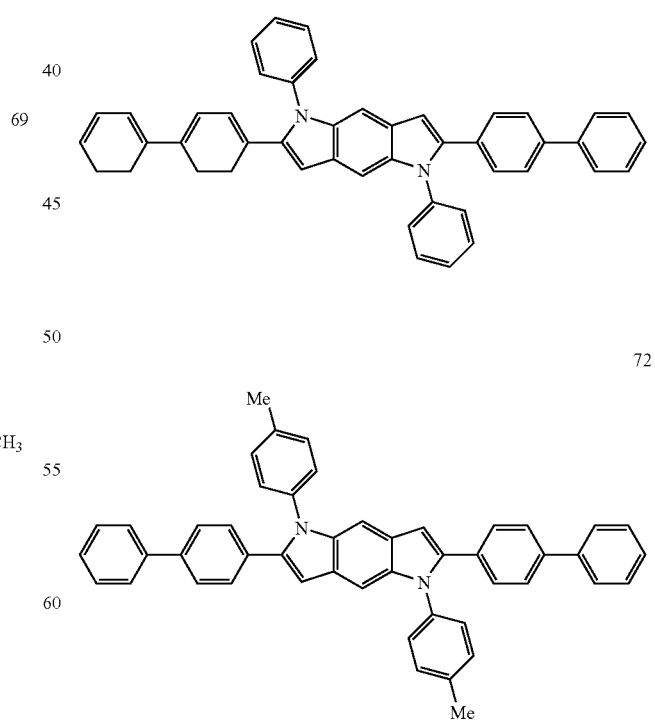
71
72

-continued

81
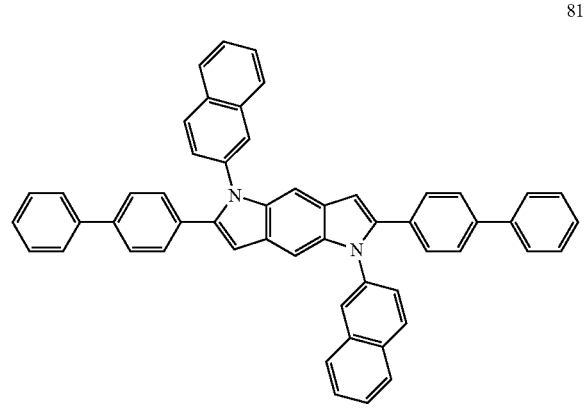
82
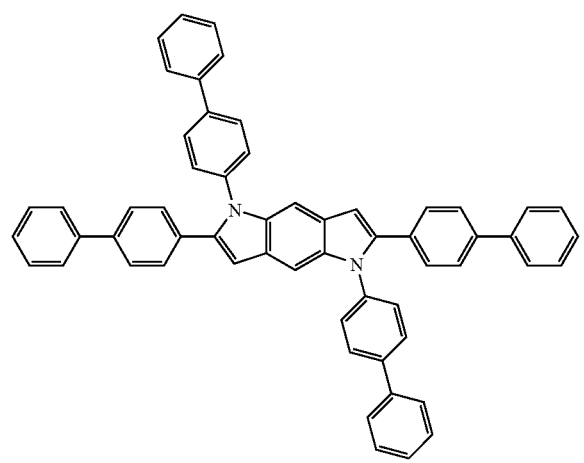
83
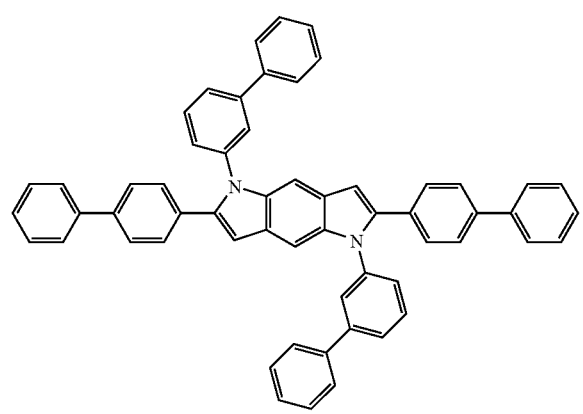
84
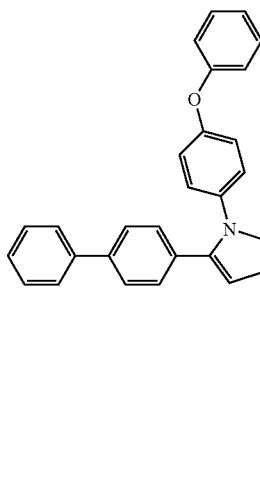
85
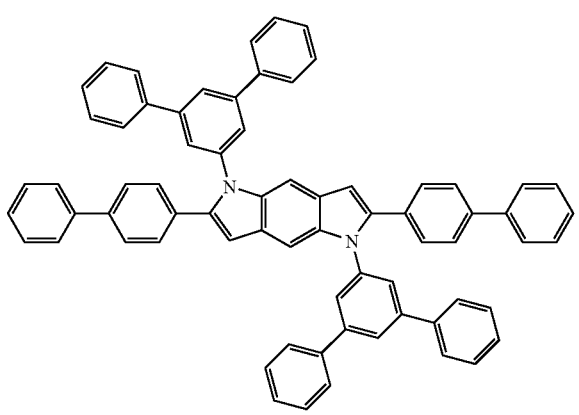
86
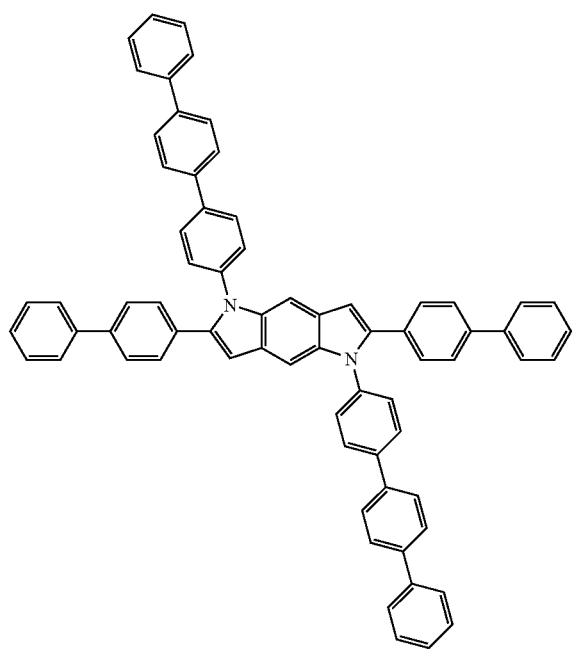

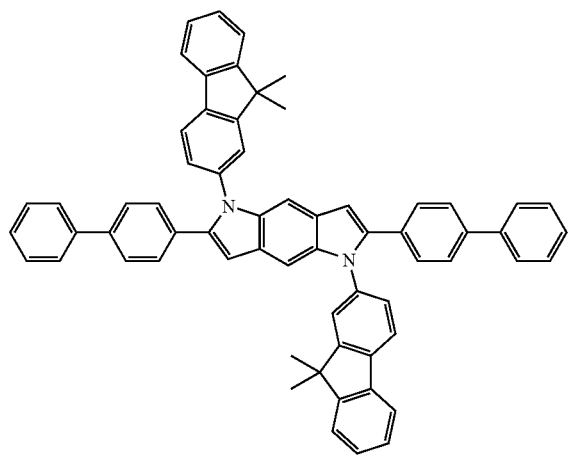
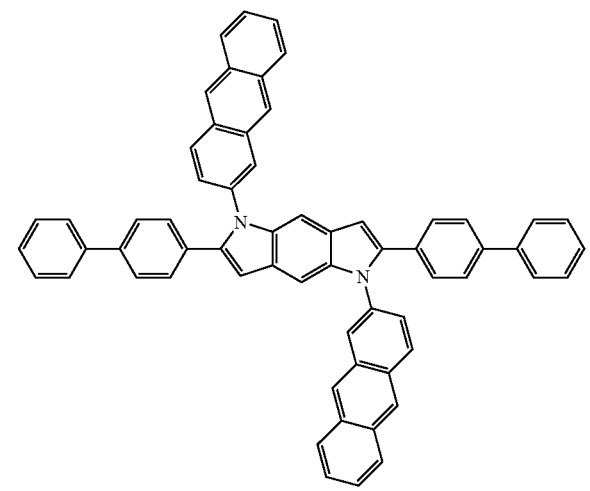

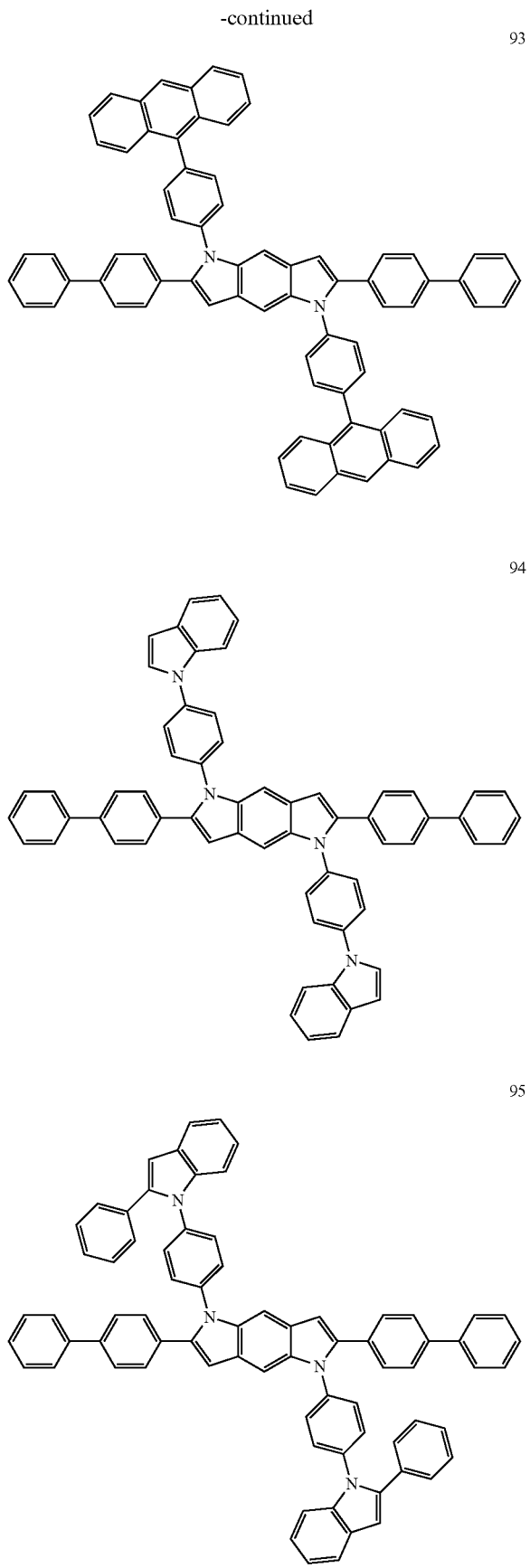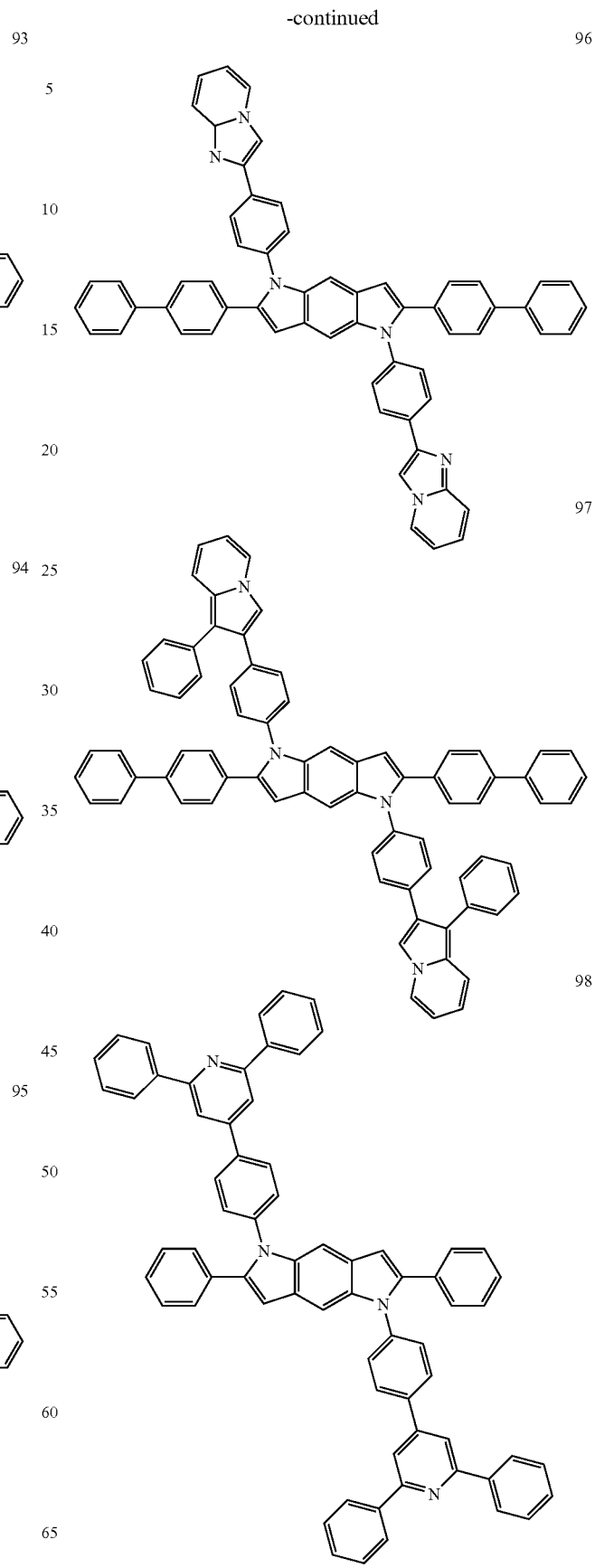

-continued
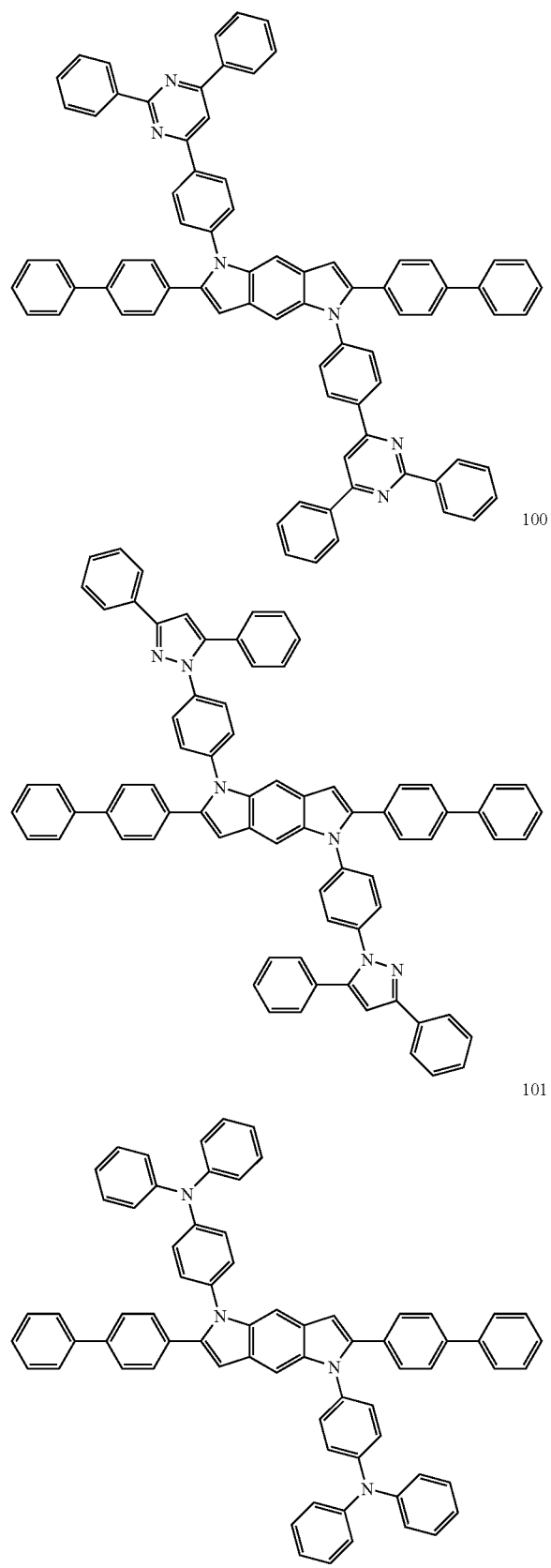
-continued
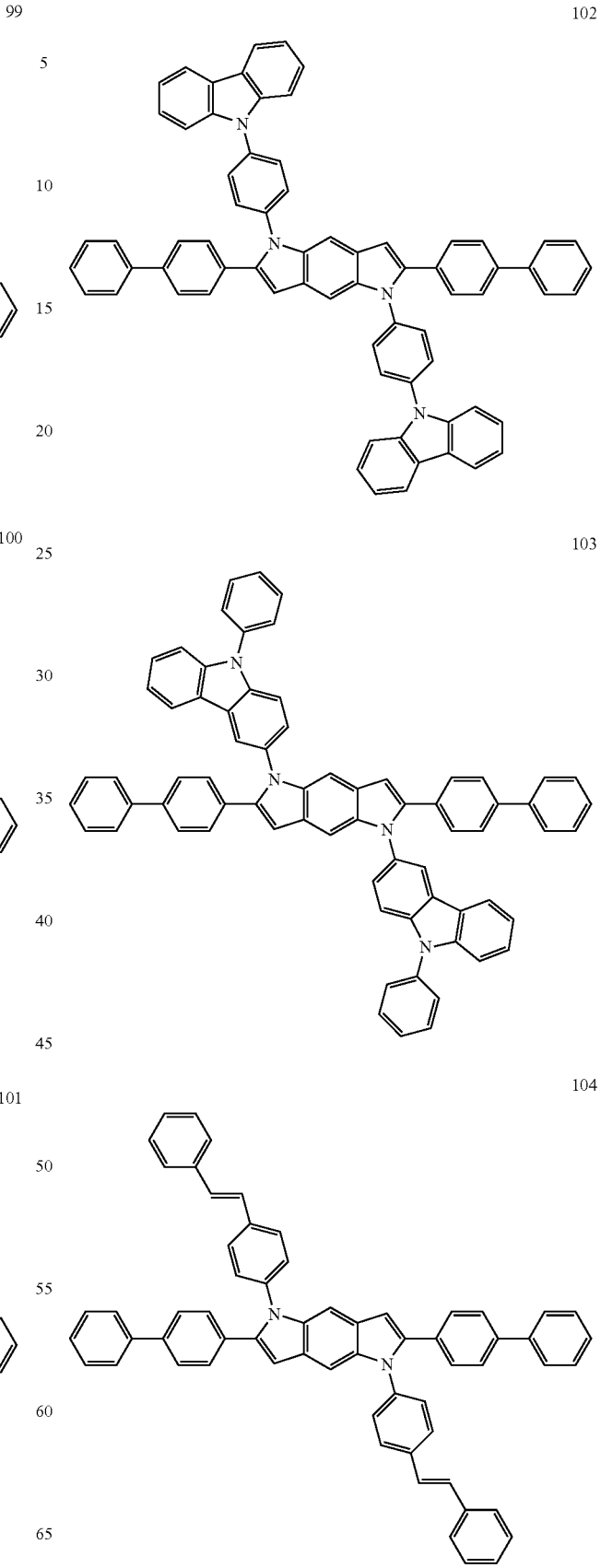

-continued

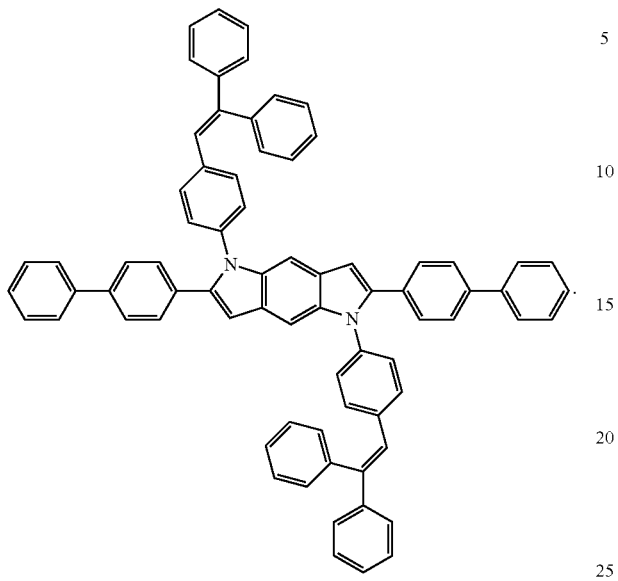
105

6. An organic light emitting device comprising:
a first electrode;
a second electrode; and
an organic layer interposed between the first electrode and the second electrode,
wherein the organic layer comprises a heterocyclic compound according to claim 1.

7. The organic light emitting device of claim 6, wherein the organic layer is a blue light emission layer.

8. An organic light emitting device comprising:
a first electrode;
a second electrode; and
an organic layer interposed between the first electrode and the second electrode,
wherein the organic layer comprises a heterocyclic compound according to claim 2.

9. An organic light emitting device comprising:
a first electrode;
a second electrode; and
an organic layer interposed between the first electrode and the second electrode,
wherein the organic layer comprises a heterocyclic compound according to claim 3.

10. An organic light emitting device comprising:
a first electrode;
a second electrode; and
an organic layer interposed between the first electrode and the second electrode,
wherein the organic layer comprises a heterocyclic compound according to claim 4.

11. An organic light emitting device comprising:
a first electrode;
a second electrode; and
an organic layer interposed between the first electrode and the second electrode,
wherein the organic layer comprises a heterocyclic compound according to claim 5.

12. A method of preparing a heterocyclic compound represented by the following Formula 3, comprising subjecting a compound represented by the following Formula 4 to a cyclization reaction:

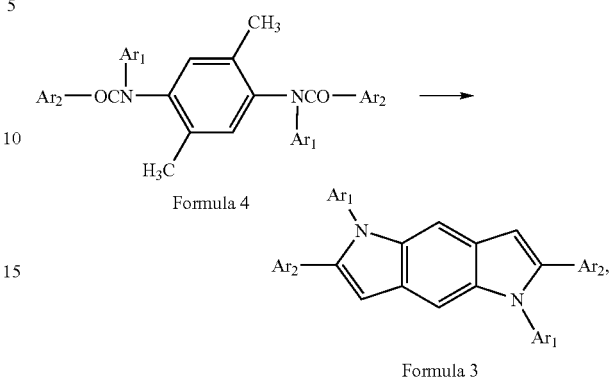

wherein the $Ar_1$ and $Ar_2$ are each independently selected from the group consisting of a phenyl group, a naphthyl group, a biphenyl group, a terphenyl group, a fluorenyl group, a carbazolyl group, a pyridyl group, and a quinolyl group, and derivatives thereof, in which at least one of the hydrogen atoms is substituted with a C1-C5 short-chain alkyl group, a C1-C5 short-chain alkoxy group, a cyano group, an amine group, a phenoxy group, a phenyl group, or a halogen group.

13. The method of claim 12, wherein the compound represented by Formula 4 is prepared by subjecting 2,5-dimethyl-1,4-phenylenediamine (a) to i) N-arylaton and ii) N-acylation:

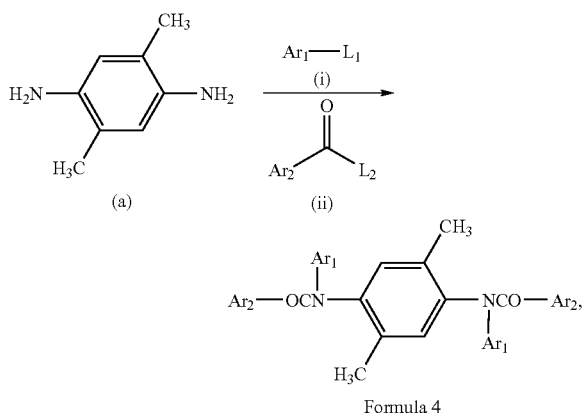

wherein,
the $Ar_1$ and $Ar_2$ are each independently selected from the group consisting of a phenyl group, a naphthyl group, a biphenyl group, a terphenyl group, a fluorenyl group, a carbazolyl group, a pyridyl group, and a quinolyl group, and derivatives thereof, in which at least one of the hydrogen atoms is substituted with a C1-C5 short-chain alkyl group, a C1-C5 short-chain alkoxy group, a cyano group, an amine group, a phenoxy group, a phenyl group, or a halogen group,
the $L_1$ is a leaving group selected from a bromo group, or an iodo group, and
the $L_2$ is a leaving group selected from a chloro group, a bromo group or an anhydride group.

* * * * *